US010087234B2

(12) United States Patent
Vuilleumier et al.

(10) Patent No.: US 10,087,234 B2
(45) Date of Patent: Oct. 2, 2018

(54) MIMETIC PEPTIDES

(71) Applicants: LES HOPITAUX UNIVERSITAIRES DE GENEVE, Geneva (CH); UNIVERSITE DE GENEVE, Geneva (CH); F. HOFFMANN-LA ROCHE AG, Basel (CH)

(72) Inventors: Nicolas Vuilleumier, Geneva (CH); Sabrina Pagano, Genève (CH); Oliver Hartley, Carouge (CH); Hubert Gaertner, Archamps (FR); Priscila Camillo Teixeira, Basel (CH); Paul Cutler, Basel (CH); Philippe Ferber, Willer (FR)

(73) Assignees: LES HOPITAUX UNIVERSITAIRES DE GENEVE, Geneva (CH); UNIVERSITE DE GENEVE, Geneva (CH); HOFFMAN-LA ROCHE INC., Little Falls, NJ (US)

( * ) Notice: Subject to any disclaimer, the term of this patent is extended or adjusted under 35 U.S.C. 154(b) by 65 days.

(21) Appl. No.: 14/440,790

(22) PCT Filed: Nov. 6, 2013

(86) PCT No.: PCT/IB2013/059948
§ 371 (c)(1),
(2) Date: May 5, 2015

(87) PCT Pub. No.: WO2014/072916
PCT Pub. Date: May 15, 2014

(65) Prior Publication Data
US 2015/0291682 A1    Oct. 15, 2015

(30) Foreign Application Priority Data
Nov. 6, 2012   (EP) .................................... 12191474

(51) Int. Cl.
*A61K 38/10*    (2006.01)
*C07K 14/775*   (2006.01)
*G01N 33/543*   (2006.01)
*A61K 38/00*    (2006.01)

(52) U.S. Cl.
CPC ..... *C07K 14/775* (2013.01); *G01N 33/54306* (2013.01); *A61K 38/00* (2013.01); *G01N 2333/775* (2013.01); *G01N 2800/32* (2013.01)

(58) Field of Classification Search
None
See application file for complete search history.

(56) References Cited

U.S. PATENT DOCUMENTS 8,957,026 B2 *   2/2015  Verdine .................. C07K 14/47
                                                         514/19.3
2009/0208921 A1 *  8/2009  Tempst ............ G01N 33/57484
                                                         435/4

FOREIGN PATENT DOCUMENTS

| CA | 2420222 A1 | 2/2002 |
| CA | 2443223 A1 | 10/2002 |
| EA | 009528 | 2/2008 |
| JP | 2004529143 A | 9/2004 |
| WO | WO-2005/058938 A2 | 6/2005 |
| WO | WO-2008/156873 A2 | 12/2008 |
| WO | WO-2012/149563 A1 | 11/2012 |

OTHER PUBLICATIONS

Sviridov, Biochemical and Biophysical Research Communications 410 (2011) 446-451 (Year: 2011).*
Vuilleumier et al., (2008) "Anti-(apolipoprotein A-1) IgGs are associated with high levels of oxidized low-density lipoprotein in acute coronary syndrome" Clinical Science, 115: 25-33.
Batuca, J., et al., (2009), "Anti-atherogenic and anti-inflammatory properties of high-density lipoprotein are affected by specific antibodies in systemic lupus erythematosus", *Rheumatology*, 48: 26-31.
Chapman, R., et al. (2004), "A Highly Stable Short α-Helix Constrained by a Main-Chain Hydrogen-Bond Surrogate", *J. Am. Chem. Soc.*, 126: 12252-12253.
Database Geneseq [online] (2005), "Human apolipoprotein A-I helices 6 and 7 peptide", EBI accession No. GSP: AEB09677; Database accession No. AEB09677.
Dinu, AR, et al. (1998) "Frequency of antibodies to the cholesterol transport protein apolipoprotein A1 in patients with SLE", *Lupus*, 7: 355-360.
Finckh, A., et al. (2012), "Evaluation of Cardiovascular Risk in Patients With Rheumatoid Arthritis: Do Cardiovascular Biomarkers Offer Added Predictive Ability Over Established Clinical Risk Scores?", *Arthritis Care & Research*, 64(6): 817-825.
International Search Report and Written Opinion dated Mar. 21, 2014 issued in PCT Patent Application No. PCT/IB2013/059948.
Keller, P., et al. (2011), "Autoantibodies against apolipoprotein A-1 and phosphorylcholine for diagnosis of non-ST-segment elevation myocardinal infarction", *Journal of Internal Medicine*, 271: 451-462.
Montecucco, F., et al. (2011), "Anti-Apolipoprotein A-1 autoantibodies are active mediators of atherosclerotic plaque vulnerability", *European Heart Journal*, 32: 412-421.
Pagano, S. et al. (2012), "Anti-apolipoprotein A-1 IgG in patients with myocardial infarction promotes inflammation through TLR2/CD14 complex", *Journal of Internal Medicine*, 272: 344-357.
Rossier, M., et al. (2012), "Antiapolipoprotein A-1 IgG Chronotropic Effects Require Nongenomic Action of Aldosterone on L-Type Calcium Channels", *Endocrinology*, 153(3): 1269-1278.
Sviridov, DO, et al. (2011), "Helix stabilization of amphipathic peptides by hydrocarbon stapling increases cholesterol efflux by the ABCA1 transporter", *Biochem Biophys Res Commun*, 410(3): 446-451.
Vuilleumier, N., et al. (2010), "Anti-apolipoprotein A-1 IgG as an independent cardiovascular prognostic marker affecting basal heart rate in myocardial infarction", *European Heart Journal*, 31: 815-823.

(Continued)

*Primary Examiner* — Satyanarayana R Gudibande
(74) *Attorney, Agent, or Firm* — Harness, Dickey and Pierce, P.L.C.

(57) ABSTRACT

The invention relates to mimetic peptides of epitope(s) of Apolipoprotein A-I, diagnostic immunoassays comprising such mimetic peptides, as well as methods for diagnosing and methods for preventing and/or treating a cardiovascular disease.

22 Claims, 14 Drawing Sheets
Specification includes a Sequence Listing.

(56) References Cited

OTHER PUBLICATIONS

Vuilleumier, N., et al. (2010), "Anti-Apolipoprotein A-1 IgG Predicts Major Cardiovascular Events in Patients with Rheumatoid Arthritis", *Arthritis & Rheumatism*, 62(9): 2640-2650.

Vuilleumier, N., et al. (2011), "Head-to-Head Comparison of Auto-Antibodies for Cardiovascular Outcome Prediction after Myocardial Infarction: a Prospective Study", *Clinical & Experimental Cardiology*, 2(11): 1-4.

Pagano S. et al., "The Human Autoantibody Response to Apolipoprotein A-I is Focused on the C-Terminal Helix: A New Rationale for Diagnosis and Treatment of Cardiovascular Disease?" PLOS ONE (2015).

\* cited by examiner (A)

(B)

(A)

k = 3 or 6
R = any amino acid side chain (B)

For n and n+4 cross-linking, k=3, n=1, *= (S)-2-(4'-pentenyl)-Alanine
For n and n+7 cross-linking, k=6, n=4, *= (R)-2-(7'-octenyl)-Alanine
R = any amino acid side chain (C)

when X = -CO-NH-, n=2, p=4, k=3
when X = -NH-CO-, n=4, p=2, k=3
R = any amino acid side chain (A)

(C)

(+)

(−)

US 10,087,234 B2

MIMETIC PEPTIDES

PRIORITY STATEMENT

This application is a national stage application under 35 U.S.C. § 371 of PCT International Application No. PCT/IB2013/059948, which has an International filing date of 6 Nov. 2013 and which claims priority under 35 U.S.C. § 119 to European Application No. 12191474.1 filed 6 Nov. 2012. The contents of each application recited above are incorporated herein by reference in their entirety.

REFERENCE TO A SEQUENCE LISTING

This application contains references to amino acid sequences and/or nucleic acid sequences which have been submitted concurrently herewith as the sequence listing text file "61478091_1.TXT", file size 17 KiloBytes (KB), created on 15 May 2014. The aforementioned sequence listing is hereby incorporated by reference in its entirety pursuant to 37 C.F.R. § 1.52(e)(5).

FIELD OF THE INVENTION

The present invention relates to peptides useful for the prognosis, diagnosis or treatment of a cardiovascular disease.

BACKGROUND OF THE INVENTION

Apolipoprotein A-I (ApoA-I) is the most abundant protein (70%) of high-density lipoprotein (HDL), whose concentration is known to be inversely correlated with cardiovascular risk. HDL-associated ApoA-I plays a crucial role in cholesterol homeostasis by regulating reverse cholesterol transport and delivering it to the liver (Yancey et al; 2003, *Arterioscler. Thromb. Vasc. Biol.* 23:712-719). HDL-associated ApoA-I also has anti-inflammatory properties and has anti-oxidant properties.

High levels of auto-antibodies to ApoA-I of IgG subclass (anti-ApoA-I IgG) have been described in patients suffering from systemic lupus erythematosus (SLE), an autoimmune condition associated with a high cardiovascular disease (CV) risk (Dinu et al, 1998, *Lupus* 7:355-360). Anti-ApoA-I IgG auto-antibodies have also been described in other high CV risk populations including myocardial infarction (MI) patients (Vuilleumier et al, 2010a, *Eur. Heart J.* 31:815-823), patients with rheumatoid arthritis (RA) (Vuilleumier et al, 2010b, *Arthritis Rheum.* 62:2640-2650), patients with acute chest pain (Keller et al, 2012, *J. Intern. Med.* 271: 451-462), and patients with severe carotid stenosis (Montecucco et al, 2011, *Eur. Heart J.* 32:412-421). In MI and RA patients, anti-ApoA-I IgG auto-antibodies were shown to be independently associated with increased risk of CV disease in high CV risk populations (Vuilleumier et al, 2010a and b, supra; Keller et al, 2012, supra), and in patients with severe carotid stenosis they were associated with increased atherosclerotic plaque vulnerability (Montecucco et al, 2011, *Eur. Heart J.* 32:412-421). Finally, in a recent head-to-head comparison study, anti-ApoA-I IgG auto-antibodies were shown to be the best humoral autoimmune marker for CV prognosis after MI (Vuilleumier, 2011, *J. Clinic. Experiment. Cardiology.* 2:69), and the only biomarker providing incremental prognostic information to traditional cardiovascular risk factors for CV risk stratification in RA patients (Finckh et al, 2012, *Arthritis Care Res (Hoboken)* 64:817-825).

From a pathophysiological point of view, anti-ApoA-I IgG auto-antibodies have been shown to be potential mediators of atherogenesis and related complications by increasing atherosclerotic lesions size and vulnerability when administered to ApoE-deficient mice (Montecucco et al, 2011, supra). While these pro-atherogenic effects are not completely understood, there is evidence that they act synergistically at several different levels. Anti-ApoA-I IgG auto-antibodies have been shown (i) to dampen the athero-protective effects of High Density Lipoprotein (Batuca et al, 2009, *Rheumatology (Oxford)* 48:26-31), (ii) to promote sterile inflammation through the Toll-like receptor2/CD14 complex (Pagano et al, 2012, *J Intern Med.* 1365-2796), (iii) to act as a pro-arrythmogenic factors through the mineralocorticoid receptor downstream activation of L-type calcium channels (Rossier et al, 2012, *Endocrinology* 153:1269-1278), and (iv) to promote neutrophil chemotaxis (Montecucco et al, 2011, supra).

Methods for the prognosis/diagnosis of cardiovascular disorders have been developed, which are based on assessing the presence of anti-ApoA-I auto-antibodies in a subject.

However, these methods are generally based on the immunologic reaction between said antibodies and full-length ApoA-I (Dinu et al, 1998, supra; Vuilleumier et al, 2010a, supra; Keller et al, 2012, supra, Montecucco et al, 2011, supra; Batuca et al, 2009, supra). Major limitations of the use of full length ApoA-I in such diagnostic immuno-assays concern the costs to produce large quantities and the instability of the protein which jeopardizes the efficiency of the assay. To solve the problem of the prognostic/diagnostic methods of the prior art, the present invention provides a novel diagnostic immunoassay based on peptides which are less costly to produce, more stable, and which specifically bind to anti-ApoA-I auto-antibodies from patients suffering from cardiovascular diseases. The methods of the invention are particularly useful for electing the therapy appropriate to the patient's specific needs, as well as for taking measures for preventing development of cardiovascular disorders, avoiding first or recurrent cardiovascular events in sub-populations of patients at high cardiovascular risk.

SUMMARY OF THE INVENTION

In a first aspect, the present invention is directed towards a mimetic peptide of an epitope of Apolipoprotein A-I (ApoA-I), wherein said mimetic peptide has:
  (a) an amino acid sequence of 15 to 80 amino acids in length,
  (b) an amino acid sequence comprising any one of:
    (i) SEQ ID NO: 2, SEQ ID NO: 3, SEQ ID NO: 4, SEQ ID NO: 5, SEQ ID NO: 21, SEQ ID NO: 23, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 22, SEQ ID NO: 24; or a variant thereof, or
    (ii) an amino acid sequence identical to any one of the sequences under (i) except that 1, 2, 3, 4, 5, or 6 amino acids of said sequence under (i) are substituted, deleted, inserted, and/or chemically modified, without aborting the capacity of said mimetic peptide to specifically bind to an anti-ApoA-I antibody, or
    (iii) any combination of two of the amino acid sequences under (i), and/or under (ii); and (c) an internal cross-linking between at least two non-contiguous amino acids of the amino acid sequence under b);
wherein said mimetic peptide is capable of specifically binding to an anti-ApoA-I antibody.

In a second aspect, the present invention is directed towards a mimetic peptide of an epitope of Apolipoprotein A-I (ApoA-I), wherein said mimetic peptide has:
(a) an amino acid sequence of 15 to 80 amino acids in length,
(b) an amino acid sequence comprising any one of:
  (i) SEQ ID NO: 5, SEQ ID NO: 21, SEQ ID NO: 23; or a variant thereof, or
  (ii) SEQ ID NO: 8, SEQ ID NO: 9, or SEQ ID NO: 25; or a variant thereof, or
  (iii) an amino acid sequence identical to any one of the sequences under (i) and/or (ii) except that 1, 2, 3, 4, 5, or 6 amino acids of said sequence under (iii) are substituted, deleted, inserted, and/or chemically modified, without aborting the capacity of said mimetic peptide to specifically bind to an anti-ApoA-I antibody, or
  (iv) any combination of two of the amino acid sequences under (i), (ii) and/or under (iii);
wherein said mimetic peptide is capable of specifically binding to an anti-ApoA-I antibody.

A third aspect of the invention concerns an isolated polynucleotide encoding said mimetic peptide, a recombinant vector comprising said polynucleotide, a host cell comprising said recombinant vector, as well as a method for preparing said mimetic peptide comprising the steps of cultivating said host cell in a culture medium and separating said peptide from the culture medium or from the host cell lysate after host cell lysis, and optionally cross-linking two non-contiguous amino acid residues of the peptide obtained via a disulphide bridge, a lactam bridge or a hydrocarbon staple.

A fourth aspect of the invention relates to a diagnostic composition, immunoassay preparation or immunoassay plate, comprising at least one mimetic peptide according to the invention.

In a fifth aspect, the invention provides a pharmaceutical composition comprising at least one mimetic peptide according to the invention.

In a sixth aspect, the invention concerns a kit for detecting anti-ApoA-I antibodies as biomarkers for a cardiovascular disease in a biological fluid sample, comprising at least one mimetic peptide according to the invention, or a combination thereof.

A seventh aspect of the invention relates to a method for detecting endogenous anti-ApoA-I antibodies in a biological fluid sample of a mammalian subject comprising the steps of:
(a) providing a biological fluid sample from a mammalian subject;
(b) bringing said biological fluid sample into contact with a solid matrix where at least one mimetic peptide according to the invention is coupled to, wherein the contacting is under conditions sufficient for binding an anti-ApoA-I antibody present in the said biological fluid sample to said at least one mimetic peptide through antigen-antibody interactions;
(c) Removing any unbound antibody from the surface of said solid matrix;
(d) Detecting the presence of an antigen-antibody complex bound to said solid matrix;
wherein the presence of said complex is indicative that the biological fluid sample contains endogenous anti-ApoA-I antibodies.

An eighth aspect concerns a method for detecting a cardiovascular disease or risk profile from a biological fluid sample of a mammalian subject comprising the steps of:
(a) providing a biological fluid sample from a mammalian subject;
(b) bringing said biological fluid sample into contact with a solid matrix where at least one mimetic peptide according to the invention is coupled to, wherein the contacting is under conditions sufficient for binding an anti-ApoA-I antibody present in said biological fluid sample to said at least one mimetic peptide through antigen-antibody interactions;
(c) Removing any unbound antibody from the surface of said solid matrix;
(d) Detecting the presence of an antigen-antibody complex bound to said solid matrix;
wherein the presence of said complex is indicative that the biological fluid sample contains one or more cardiovascular disease associated anti-ApoA-I auto-antibodies.

An ninth aspect relates to a method for preventing and/or treating a cardiovascular disease in a subject in need thereof comprising administering said mimetic peptide, a pharmaceutical formulation thereof, or a 3-dimensional structural analogue of said mimetic peptide, to said subject.

A tenth aspect concerns a method for preventing and/or treating a cardiovascular disease in a subject suffering from acute chest pain, acute coronary syndrome, rheumatoid arthritis, systemic lupus erythematosus, severe carotid stenosis, end-stage renal disease or periodontitis, comprising the steps of:
(a) detecting endogenous anti-ApoA-I antibodies in a biological fluid sample of a mammalian subject according to the method of the invention; and
(b) administering at least one agent selected from: (i) a mimetic peptide according to the invention, or a pharmaceutical formulation thereof, (ii) a 3-dimensional structural analogue of a mimetic peptide according to any one of claims 1 to 5, (iii) a pharmaceutical composition comprising ApoA-I, and (iv) an agent suitable for preventing and/or treating a cardiovascular disease.

Other features and advantages of the invention will be apparent from the following detailed description.

Alanine; for a cross-linking between residues at n and n+7 positions, k is 6, n is 4, * is (R)-2-(7'-octenyl)-Alanine; R is any amino acid side chain; in (C): when X is —CO—NH—, n is 2, p is 4, k is 3; when X is —NH—CO—, n is 4, p is 2, k is 3; R is any amino acid side chain. Next to the brackets, m, k, and l refer to the positions of the amino acids on the peptide sequence.

Figure 3:
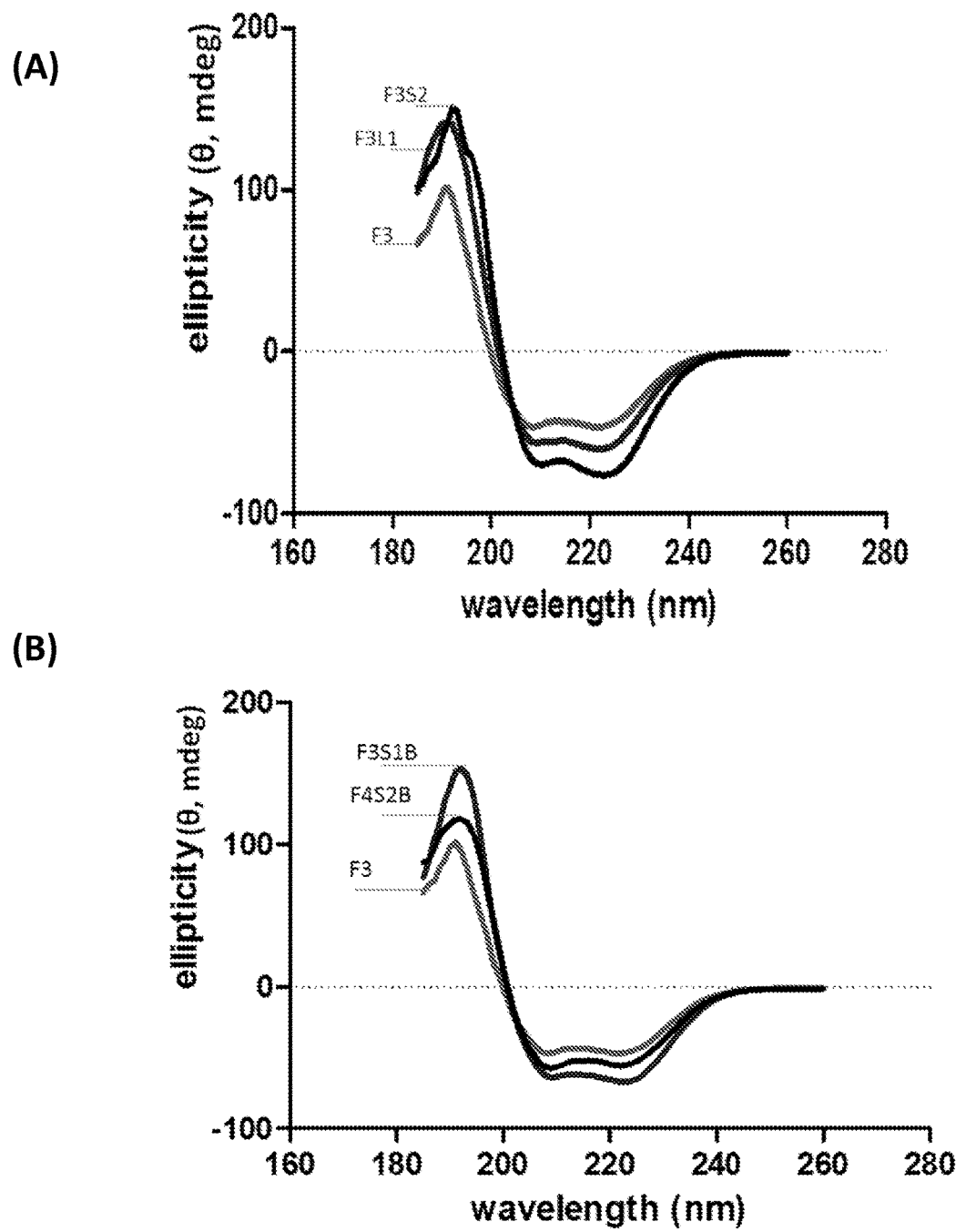
Figure 3:
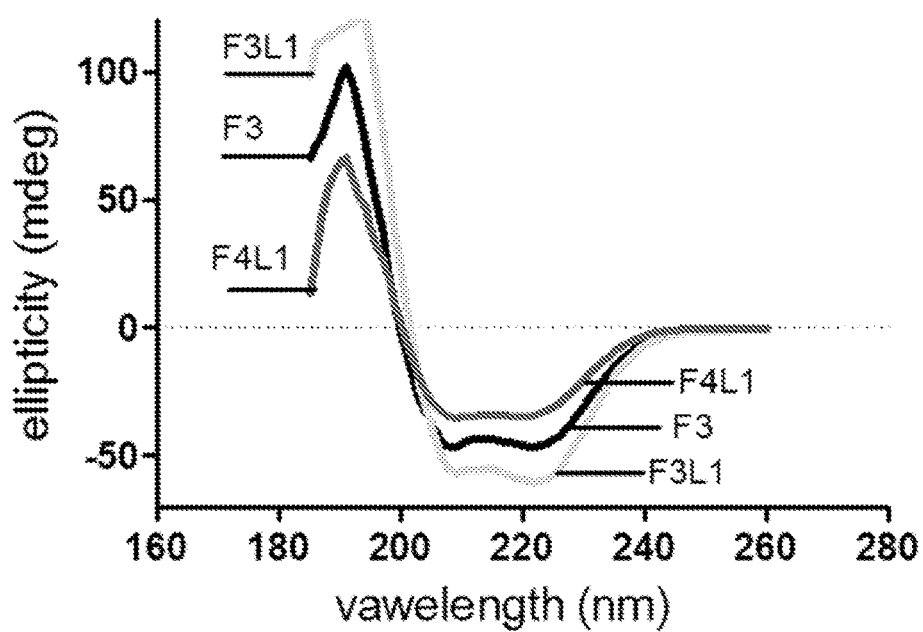

FIG. 3. CD spectroscopy of the mimetic peptides F3L1 and F3S2A (F3S2A=F3S2) (A), F3S1B and F4S2B (B), F3L1 and F4L1 (C) shows increased alpha-helical content in comparison to the non-stapled control F3 peptide.

Figure 4:
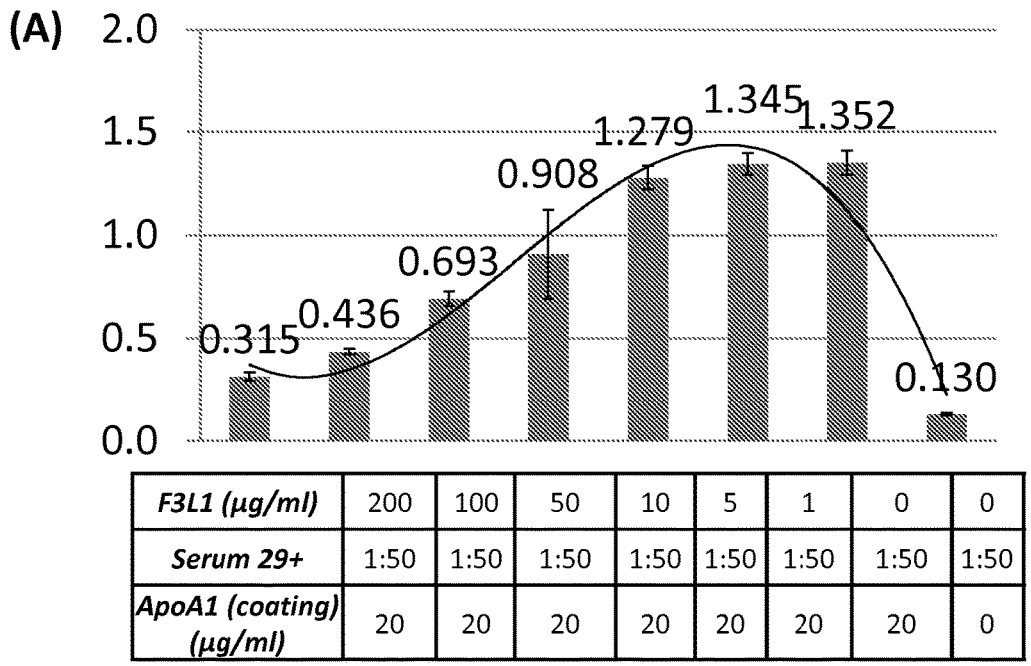
Figure 4:
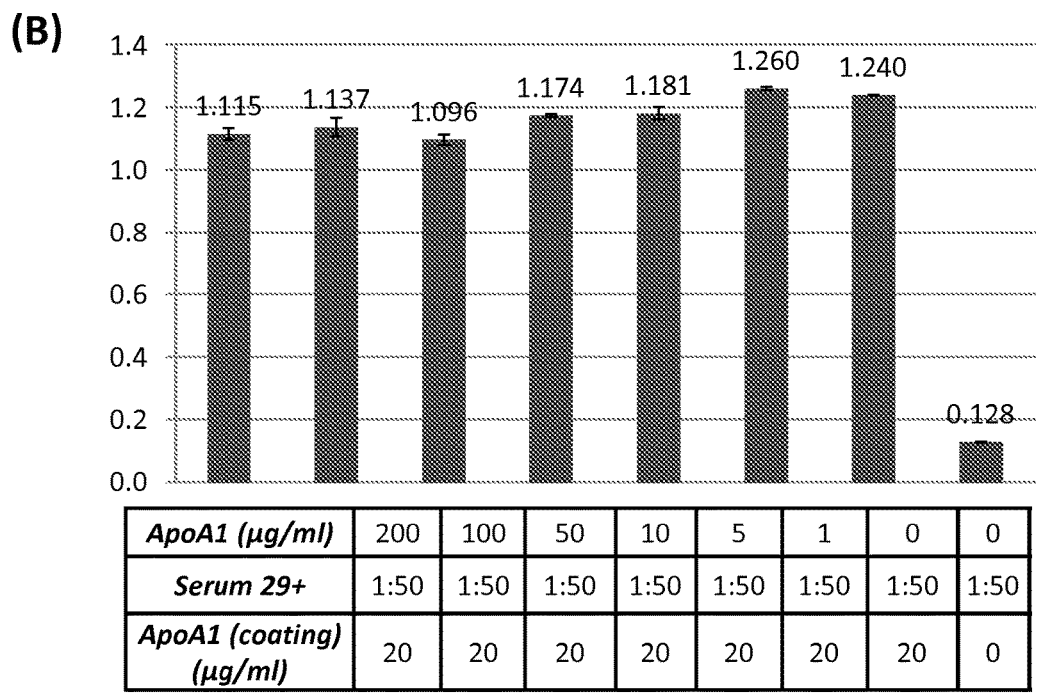

FIG. 4. Competition ELISA shows that mimetic peptide F3L1 competes effectively with intact ApoA-I for binding to anti-ApoA-I antibodies. Serum from a patient known to be positive for anti-ApoA-I antibodies was preincubated with mimetic peptide F3L1 at the indicated concentrations and then added to ELISA plates coated with intact ApoA-I, with the subsequent assay steps carried out according to the standard protocol (A). Comparative results of competition ELISA assays carried out with ApoA-I as competitor (B).

Figure 5:
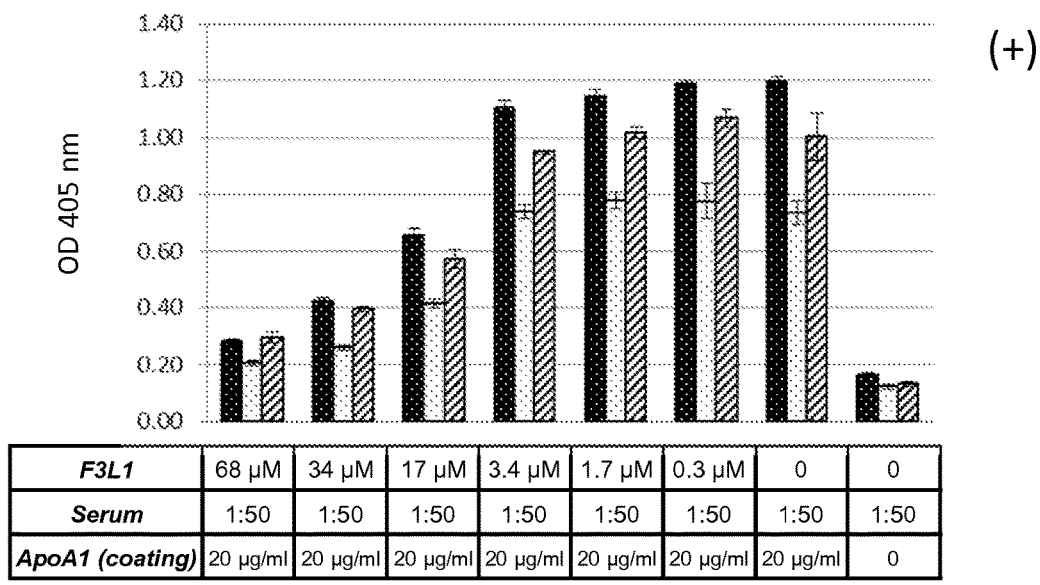
Figure 5:
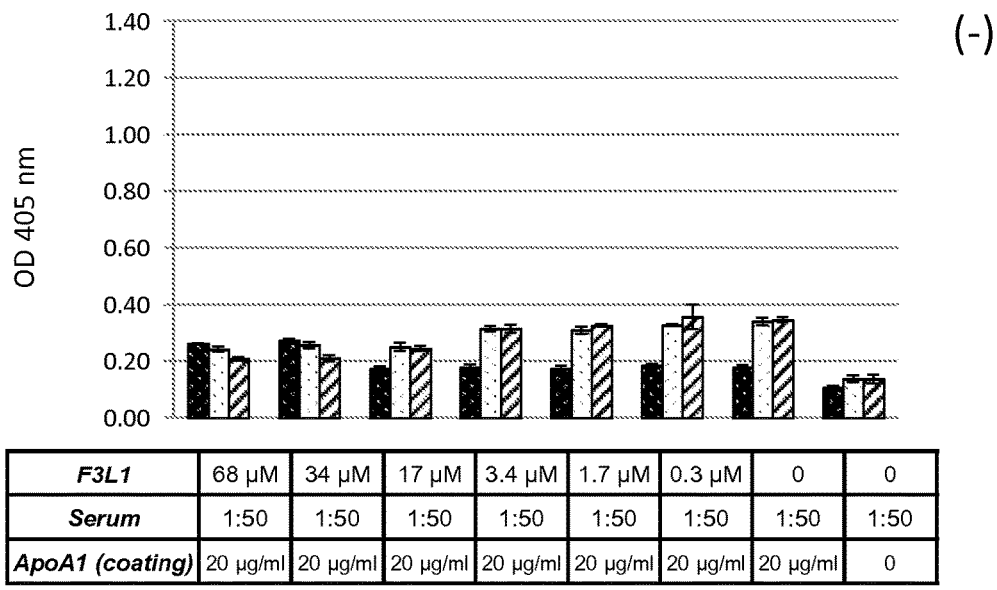
Figure 5:
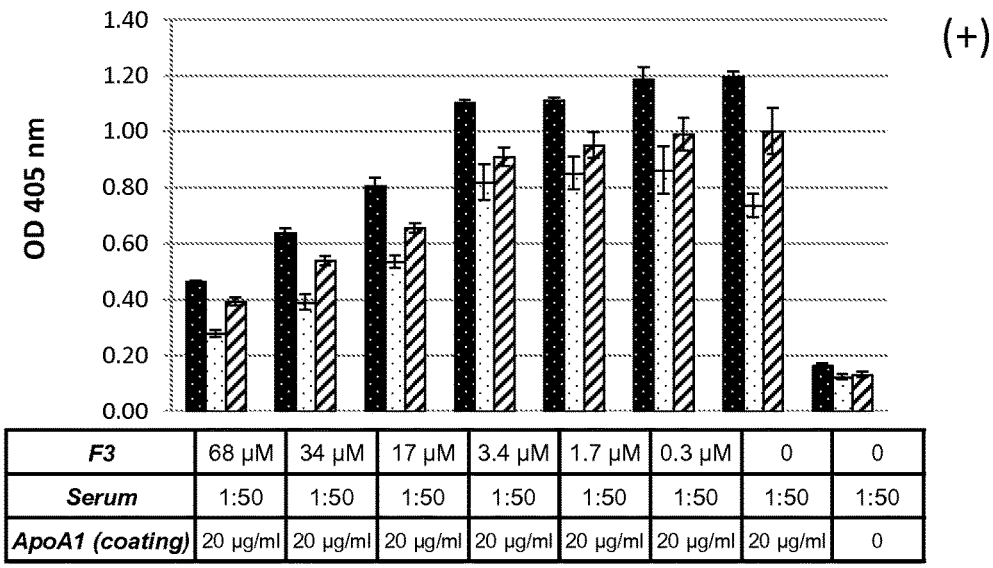
Figure 5:
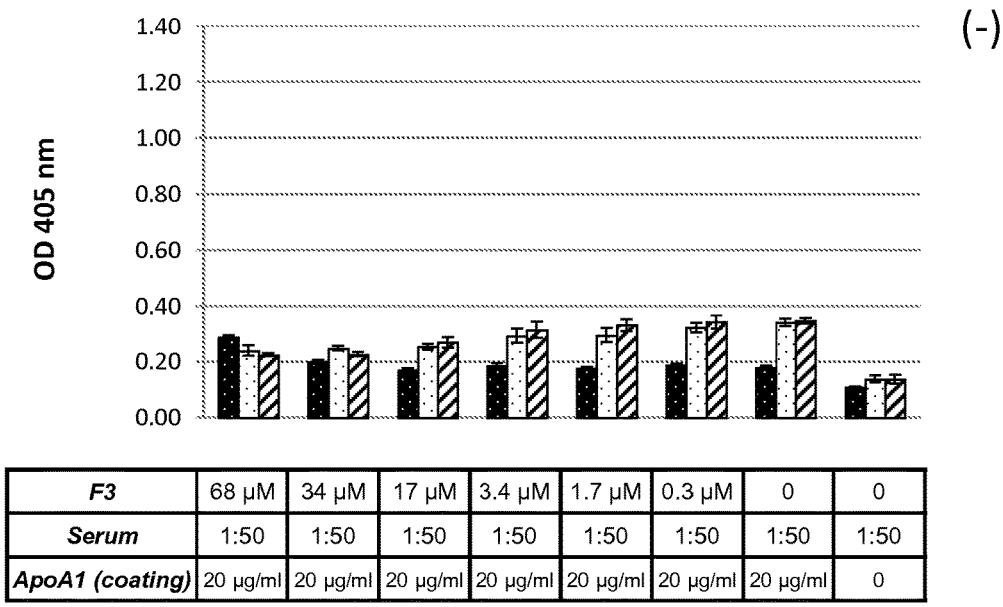
Figure 5:
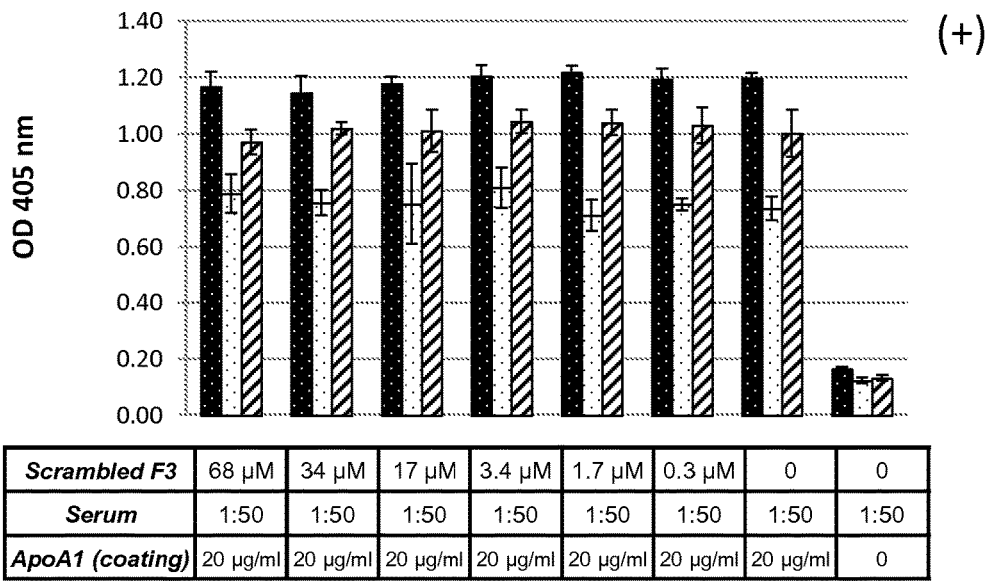
Figure 5:
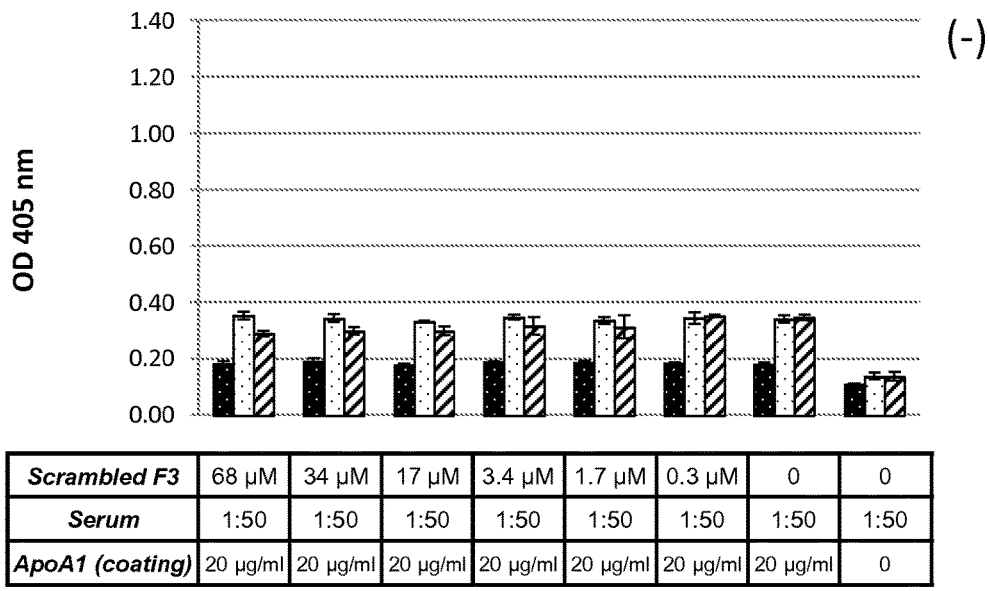

FIG. 5. Competition ELISA shows that mimetic peptide F3L1 competes effectively with intact ApoA-I for binding to anti-ApoA-I antibodies. Serum from 3 patients known to be positive (+) for anti-ApoA-I antibodies was preincubated with mimetic peptide F3L1 (A), F3 (B), or scrambled F3 (C), at the indicated concentrations and then added to ELISA plates coated with intact ApoA-I, with the subsequent assay steps carried out according to the standard protocol. Controls with serum from 3 patients known to be negative (−) for anti-ApoA-I antibodies.

Figure 6:
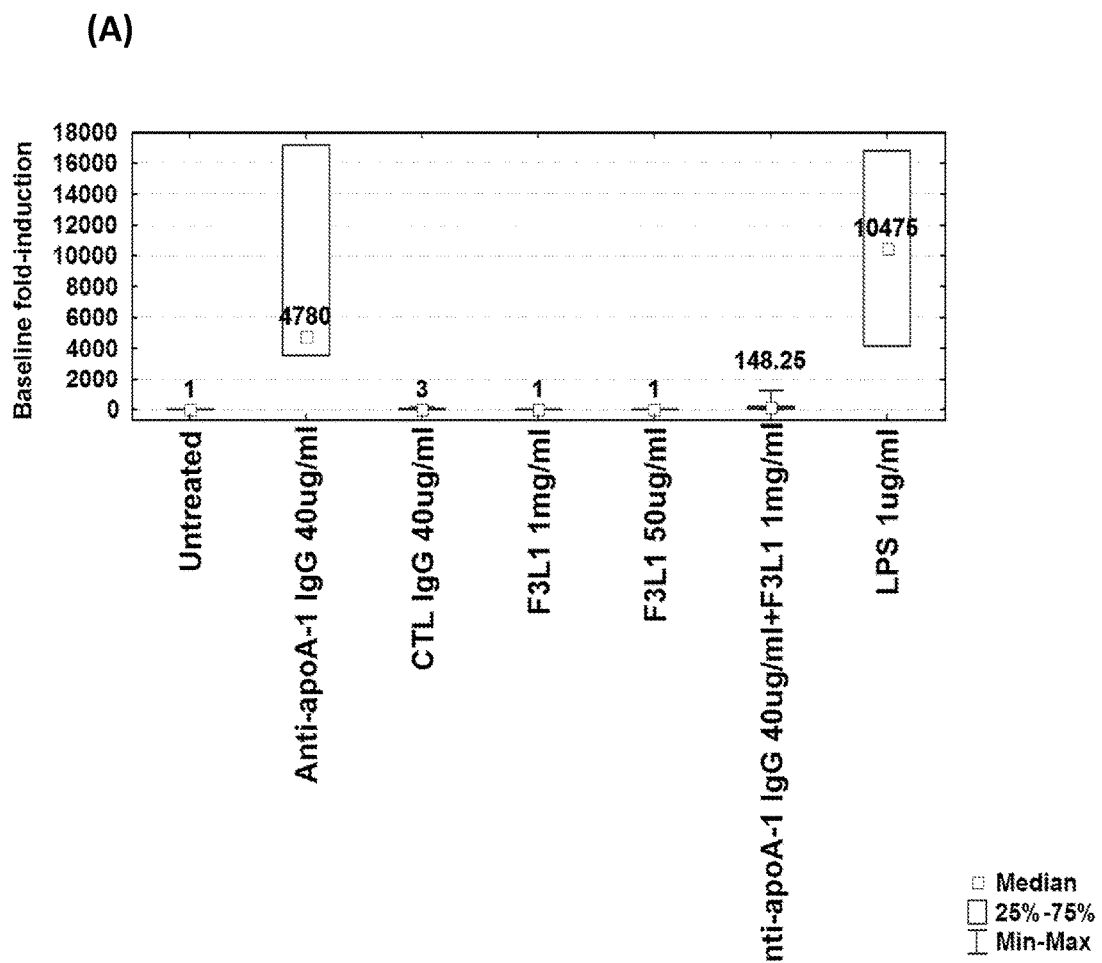
Figure 6:
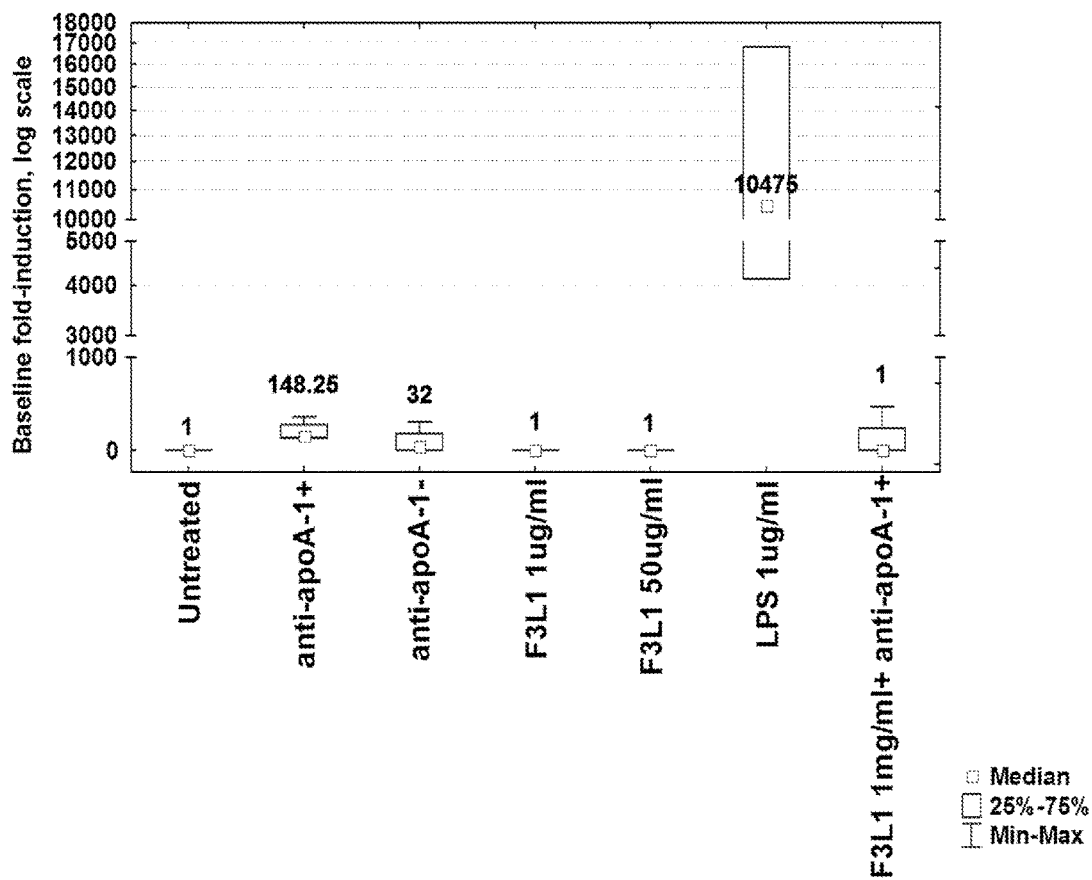

FIG. 6. Mimetic peptide F3L1 inhibits the anti-ApoA-I IgG related pro-inflammatory response. Effect on TNF-alpha production by macrophages induced by anti-ApoA-I IgG (A) or by a pool of IgG from patients positive for anti-ApoA-I antibodies (B).

Figure 7:
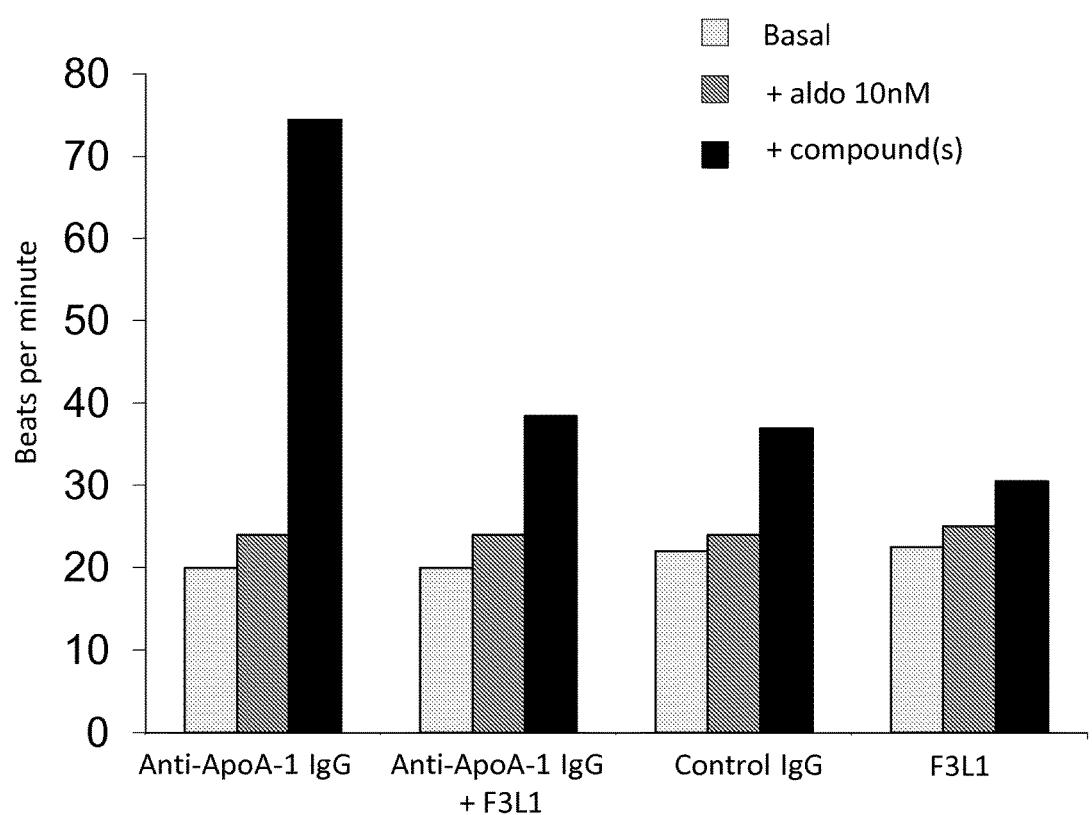

FIG. 7. Mimetic peptide F3L1 inhibits the anti-ApoA-I IgG related chronotropic response.

Figure 8:
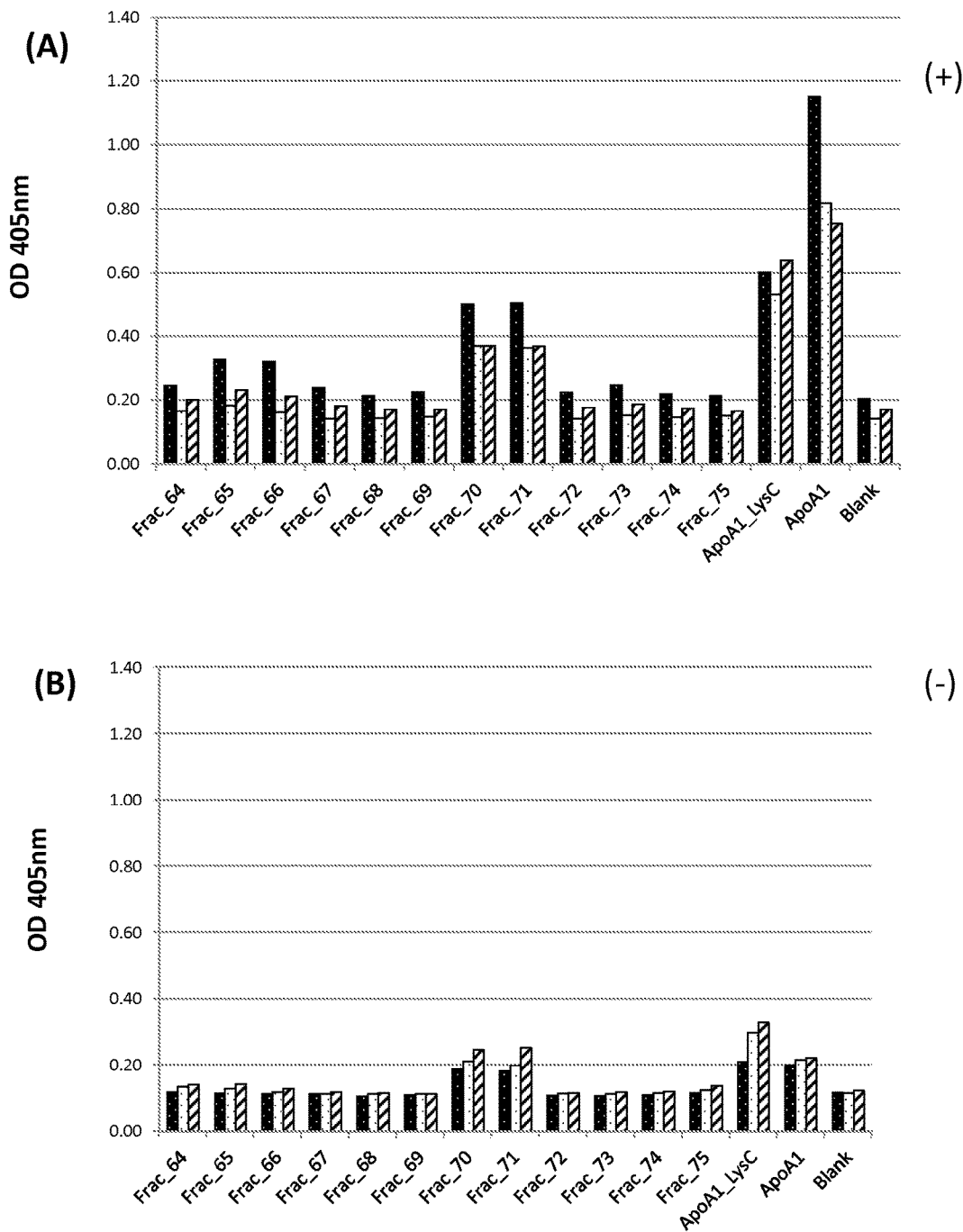

FIG. 8. ApoA-I epitope identification using digestion at lysine (K) residues. Immunoreactivity of autoantibodies from positive (A) and negative (B) patient sera against peptides present in each collected fraction.

Figure 9:
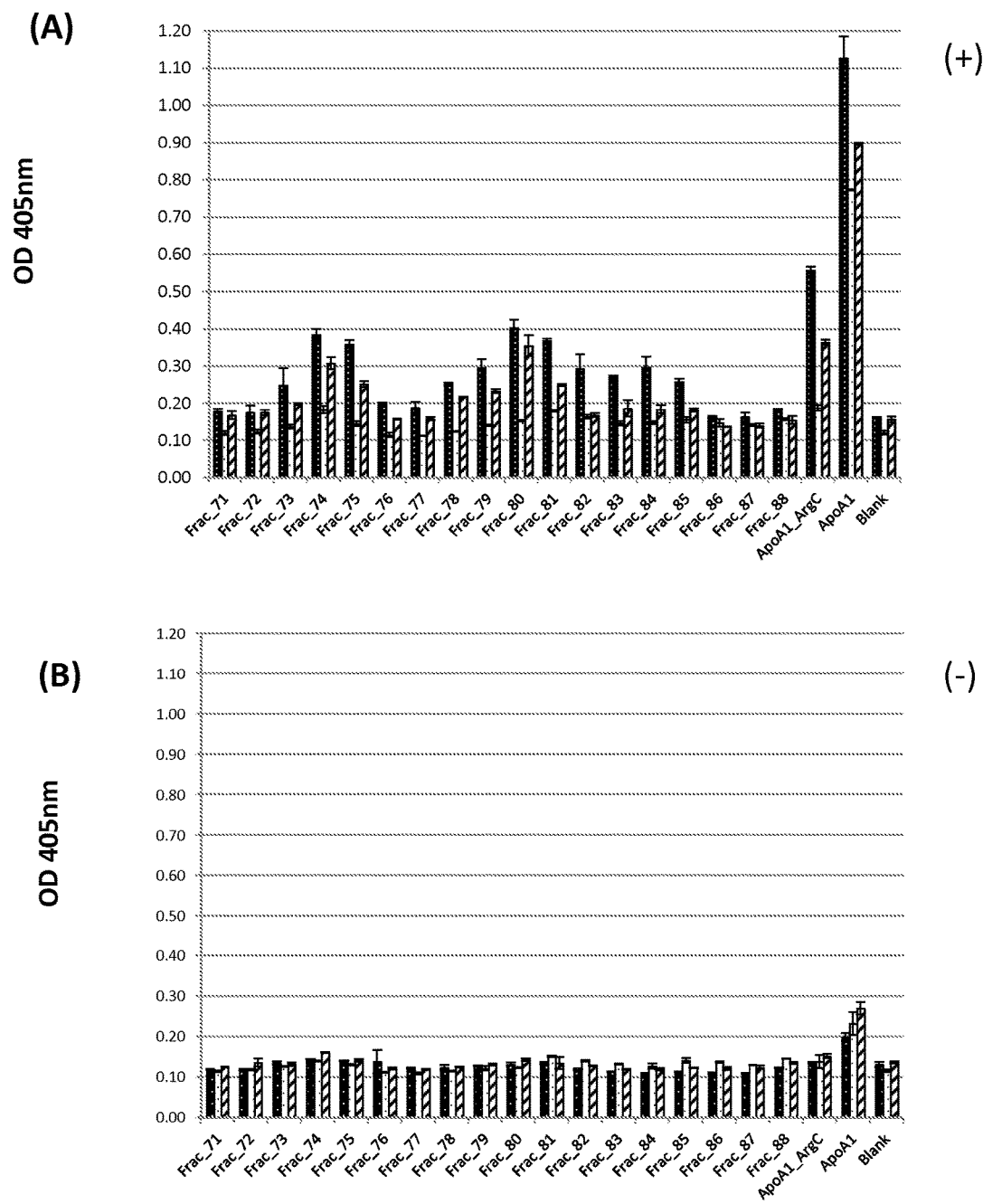

FIG. 9. ApoA-I epitope identification using digestion at arginine (R) residues. Immunoreactivity of autoantibodies from positive (A) and negative (B) patient sera against peptides present in each collected fraction.

DETAILED DESCRIPTION OF THE INVENTION

"Apolipoprotein A-1", also referred herewith as "ApoA-I" and "ApoA-1", is a protein that is encoded, in humans, by the APOA1 gene. In humans, ApoA-I is a 28 kDa protein (Uniprot accession number P02647). Mature human APO-A1 comprises 243 amino acids (SEQ ID NO: 1). ApoA-I protein has a specific role in lipid metabolism. Apolipoprotein A-I is the major protein component of high density lipoprotein (HDL) in plasma. The protein promotes cholesterol efflux from tissues to the liver for excretion. It is a cofactor for lecithin cholesterolacyltransferase (LCAT) which is responsible for the formation of most plasma cholesteryl esters. ApoA-I was also isolated as a prostacyclin (PGI2) stabilizing factor, and thus may have an anti-clotting effect. Defects in the gene encoding it are associated with HDL deficiencies, including Tangier disease, and with systemic non-neuropathic amyloidosis. ApoA-I is a conformationally flexible and dynamic protein, capable of switching between at least two strikingly different conformations: lipid-free, and lipid-associated conformations. Structural studies of the intact, lipid-free form of Apolipoprotein A-1 indicate the presence of six alpha helices as follows: Helix A from Arginine at position 10 to Glycine at position 39 of SEQ ID NO: 1; Helix B from Asparagine at position 48 to Glutamine at position 84 of SEQ ID NO: 1; Helix C from Lysine at position 94 to Glutamic acid at position 136 of SEQ ID NO: 1; Helix D from Glutamic acid at position 146 to Alanine at position 187 of SEQ ID NO: 1; Helix E from Alanine at position 196 to Glutamic acid at position 212 of SEQ ID NO: 1; Helix F from Proline at position 220 to Glutamine at position 243 of SEQ ID NO: 1.

The terms "mimetic peptide of an epitope" also called "mimotope", as used herein refers to a peptide that mimics an epitope of a target protein. Said mimetic peptide is sufficiently similar to a native epitope of the target protein that it can be recognized by an antibody specific to the native epitope (and, thus, possesses antigenic properties) and, possibly, also induce an immunologic response specific for the native epitope (and, thus, possesses immunogenic properties). More specifically, the terms "mimetic peptide of an epitope of ApoA-I" refers to a peptide that mimics an antigenic determinant of the Apolipoprotein A-I and which is, therefore, recognized by an antibody which specifically binds to Apolipoprotein A-I, also called an ApoA-I antibody.

The term "epitope", also called herewith "epitope" or "antigenic determinant", is the part of an antigen that is recognized by the immune system, specifically by antibodies, B cells, or T cells.

"Antigenicity" refers to the antigenic properties of an epitope and corresponds to the ability of the epitope to combine with the final products of the immune response such as the secreted antibodies and/or surface receptors on T-cells. "Immunogenicity" refers to the immunogenic properties of an epitope and corresponds to the ability of the epitope to induce a humoral and/or cell-mediated immune response. Although all epitopes that have the property of immunogenicity also have the property of antigenicity, the reverse is not true.

The expression "two non-contiguous amino acids", applied to an amino acid sequence, designates herewith two amino acids which are not contiguous, i.e. not adjacent to each other, in the primary structure of the peptide having said amino acid sequence.

The term "ApoA-I antibody" or "anti-ApoA-I antibody" as used herein refers to any antibody or variant form thereof, including but not limited to, antibody fragment, domain antibody or single chain antibody capable of selectively binding to ApoA-I protein, for instance the lipid free form of ApoA-I, or fragment thereof. In particular, ApoA-I antibodies include an ApoA-I antibody able to bind to the epitopes of mammalian, notably human, ApoA-I, in particular ApoA-I of amino acid sequence SEQ ID NO: 1, or in particular any epitope localized within a region consisting of any one of the amino acid sequences SEQ ID NO: 2 to SEQ ID NO: 9 or SEQ ID NO: 23. An ApoA-I antibody includes murine, chimeric, humanized, or fully human antibodies, genetically engineered or bispecific or multispecific antibodies as well as fragments thereof such as single chain antibodies (scFv) or domain antibodies against ApoA-I protein or fragment thereof and the like. Anti-ApoA-I antibodies may be monoclonal or polyclonal antibodies, or fragments or derivatives thereof having substantially the same antigen specificity. In particular, the anti-ApoA-I antibodies can be auto-antibodies (also called endogenous antibodies) produced in patients at high cardiovascular risk, in particular in patients populations such as those suffering from acute chest pain, acute coronary syndrome, rheumatoid arthritis, systemic lupus erythematosus, severe carotid stenosis, end-stage renal disease and periodontitis. The term "selectively" indicates that the antibodies preferentially recognize and/or bind the target polypeptide or epitope, i.e. with a higher affinity than to any other antigen or epitope, i.e. the binding to the target polypeptide can be discriminated from non-specific binding to other antigens. The binding affinity of an antibody can be readily determined by one of ordinary skill in the art, for example, by Scatchard analysis (Scatchard et al., 1949, *Ann. N.Y. Acad.* 1949. 51, 660-672).

The term "pharmaceutically acceptable" refers to a carrier comprised of a material that is not biologically or otherwise undesirable.

The term "carrier" refers to any components present in a pharmaceutical formulation other than the active agent and thus includes diluents, binders, lubricants, disintegrants, fillers, coloring agents, wetting or emulsifying agents, pH buffering agents, preservatives and the like.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it for example based on familial history; (b) inhibiting the disease, i.e., arresting its development; or relieving the disease, i.e., causing regression of the disease and/or its symptoms or conditions such as improvement or remediation of damage.

In particular, treatment of cardiovascular diseases comprises preventing, decreasing or even eradicating the symptoms of the diseases or disorders for instance by decreasing the prevalence and incidence of myocardial infarction stroke or peripheral artery disease in the general population (primary prevention) or in patients who already suffered from such events (secondary prevention).

The terms "cardiovascular diseases" are defined herewith as diseases or disorders affecting heart or blood vessels. Non-limiting examples of cardiovascular diseases or disorders include mostly the acute and chronic manifestation of arteriosclerosis such as acute coronary syndromes, stroke, transient ischemic attacks, arrhythmia, heart failure, and peripheral artery disease.

The terms "cardiovascular disease risk" or "cardiovascular risk" are defined herewith as the probability of developing a cardiovascular disease for subjects who have not already developed major atherosclerotic disease. This probability is typically evaluated based on the observation of different traditional cardiovascular risk factors, such as gender, age, family history, tobacco use, diabetes, high blood pressure (hypertension), high cholesterol (dyslipidemia), obesity, physical inactivity, and unhealthy diets, also known as risk score tables such as the Framingham risk score (D'Agostino et al, 2008, *Circulation* 117:743-53). A subject is qualified as having a "high cardiovascular risk" when the 10-year risk of developing a cardiovascular disease is higher than 10% based on the 10-year global Framingham risk score (D'Agostino, et al, 2008, *Circulation* 117:743-53).

The term "subject" as used herein refers to mammals. For example, mammals contemplated by the present invention include human, primates, domesticated animals such as cattle, sheep, pigs, horses, laboratory rodents and the like.

The expression "biological fluid sample" refers to a clinical fluid sample for testing which is taken from a body fluid from a mammal such as saliva, blood and urine. For example, a biological fluid sample is a serum sample from a human subject.

The expression "control sample" refers to a positive control or a negative control sample. A negative control sample includes a body fluid sample taken from a subject that is of the same or homologous species as the subject to be assayed for anti-ApoA-I auto-antibodies and is known to have normal biological state, e.g. without detectable auto-antibodies against ApoA-I or a solution which does not contain antibodies that are immunoreactive with ApoA-I. A positive control sample includes a body fluid sample taken from a subject that is of the same or homologous species as the subject to be assayed for auto-antibodies and is known to have detectable auto-antibodies against ApoA-I or a solution which does contain antibodies that are immunoreactive with ApoA-I.

The term "variant", applied to a peptide or polypeptide, as referred to herein means a peptide or polypeptide substantially homologous to the referenced peptide sequence, but which has an amino acid sequence different from that of the referenced sequence because of one or more amino acid deletion, insertion and/or substitution. Substantially homologous means a variant amino acid sequence which is identical to the referenced peptide sequence except for the deletion, insertion and/or substitution of 1, 2, 3, 4, 5 or 6 amino acid residues. The identity of two amino acid sequences can be determined by visual inspection and/or mathematical calculation, or more easily by comparing sequence information using known computer program used for sequence comparison such as Clustal package version 1.83. A variant may comprise a sequence having at least one conservatively substituted amino acid, meaning that a given amino acid residue is replaced by a residue having similar physiochemical characteristics. Generally, substitutions for one or more amino acids present in the original polypeptide should be made conservatively. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known (Kyte, et al, 1982, *J. Mol. Biol.*, 157: 105-131). For example, a "conservative amino acid substitution" may involve a substitution of a native amino acid residue with a non native residue such that there is little or no effect on the polarity or charge of the amino acid residue at that position. Desired amino acid substitutions (whether conservative or non-conservative) can be determined by those skilled in the art at the time such substitutions are desired. Exemplary amino acid substitutions are presented in Table 1 below. The term "variant" also includes a peptide or polypeptide substantially homologous to the referenced peptide sequence, but which has an amino acid sequence different from that of the referenced sequence because one or more amino acids have been chemically modified or substituted by amino acids analogs. For instance, 1, 2, 3, 4, 5, or 6 amino acids have been chemically modified. The chemical modification of one or more amino acid residues includes modifications for establishing a hydrocarbon staple such as chemically modifying any residue of the sequence into (S)-2-(4'-pentenyl)-alanine or (R)-2-(7'-octenyl)-alanine Thus, a variant as defined herewith also includes the referenced peptide sequence where one or more amino acid residues of the sequence have been substituted with (S)-2-(4'-pentenyl)-alanine or (R)-2-(7'-octenyl)-alanine for establishing a hydrocarbon staple.

TABLE 1

| Original residues | Examples of substitutions |
| --- | --- |
| Ala (A) | Val, Leu, Ile |
| Arg (R) | Lys, Gln, Asn |
| Asn (N) | Gln |
| Asp (D) | Glu |
| Cys (C) | Ser, Ala |
| Gln (Q) | Asn |
| Glu (E) | Asp |
| Gly (G) | Pro, Ala |
| His (H) | Asn, Gln, Lys, Arg |
| Ile (I) | Leu, Val, Met, Ala, Phe, Norleucine |
| Leu (L) | Ile, Val, Met, Ala, Phe, Norleucine |
| Lys (K) | Arg, Gln, Asn |
| Met (M) | Leu, Ile, Phe |
| Phe (F) | Leu, Val, Ile, Ala, Tyr |
| Pro (P) | Ala, Gly |
| Ser (S) | Thr, Ala, Cys |
| Trp (W) | Phe, Tyr |
| Thr (T) | Ser |
| Tyr (Y) | Trp, Phe, Thr, Ser |
| Val (V) | Ile Met, Leu, Phe, Ala, Norleucine |

Variants also cover mimetic peptides according to the invention containing α,α-dialkylated residues such as 2-aminoisobutyric acid for stabilizing alpha-helical structures. Preferred positions for adding α,α-dialkylated residues concern positions of residues which do not have intrinsic and distinct propensity for helix formation, such as Proline, Glycine or Valine, this latter one having intrinsic propensity to stabilize sheet structure. (R)-2-(7'-octenyl)-Alanine and (S)-2-(4'-pentenyl)-Alanine which can be used for generating the hydrocarbon staple described herewith belong also to this family of compounds. Such residues can also be incorporated in positions that are prone to proteolytic cleavage of the peptide if there is any therapeutic application for said peptide. Examples of positions where α,α-dialkylated residues can be added on the ApoA-I amino acid sequence include those in the F helix region such as Proline at position 229, Valine at position 220, Phenylalanine at position 221, Lysine at position 225, Valine at position 226 or Phenylalanine at position 228, the positions referring to the mature ApoA-I amino acid sequence SEQ ID NO: 1.

The term "solid matrix" includes any solid phase support suitable for carrying out an immunoassay or a method according to the invention. It includes beads, microparticles, nanoparticles, tubes, fabrics or plates, films, slides, wells, formed from or coated with glass, polystyrene, polypropylene, nitrocellulose, quartz, ceramic, dextran or other materials. For example, the solid matrix is in a form of microtiter wells, such as a 96-well microtiter plate.

The term "kit" comprises at least one mimetic peptide according to the invention, or a variant thereof, or a combination thereof, as described herein to be coupled or already coupled to a solid matrix and optionally instructional material.

The term "efficacy" of a treatment or method according to the invention can be measured based on changes in the course of disease or condition in response to a use or a method according to the invention. For example, the efficacy of a treatment or method according to the invention can be measured by its impact on i) different relevant clinical endpoints (for example: overall mortality, cardiovascular related mortality, acute coronary syndrome or stroke relapse, hospitalisation . . . ), and/or on ii) surrogate markers such as the impact of the therapeutic compounds in different animal or in vitro systems. The term "effective amount" as used herein refers to an amount of at least one mimetic peptide according to the invention, or a pharmaceutical formulation thereof, that elicits a detectable reduction of the symptoms of the cardiovascular disease in a subject that is being administered said mimetic peptide, these symptoms can include, for instance, overall mortality, cardiovascular related mortality, acute coronary syndrome or stroke relapse, CV-related hospitalisation.

Mimetic Peptides of Epitopes of ApoA-I

One aspect of the invention relates to peptides which mimic epitope(s) of the lipid-free Apolipoprotein A-1 conformation and are able to specifically bind to anti-ApoA-I auto-antibodies from patients suffering from cardiovascular diseases or disorders.

In a first aspect, the mimetic peptide has an internal cross-linking.

In one embodiment, the invention relates to a mimetic peptide of an epitope of ApoA-I, wherein said peptide has:
(a) an amino acid sequence of 15 to 80 amino acids in length;
(b) an amino acid sequence comprising any one of:
 (i) SEQ ID NO: 2, SEQ ID NO: 3, SEQ ID NO: 4, SEQ ID NO: 5, SEQ ID NO: 21, SEQ ID NO: 23, SEQ ID NO: 6, SEQ ID NO: 7, SEQ ID NO: 8, SEQ ID NO: 9, SEQ ID NO: 25, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 22, SEQ ID NO: 24; or a variant thereof;
 (ii) an amino acid sequence identical to any one of the sequences under (i) except that 1, 2, 3, 4, 5, or 6 amino acids of said sequence under (i) are substituted, deleted, inserted, and/or chemically modified, without aborting the capacity of said mimetic peptide to specifically bind to an anti-ApoA-I antibody,
 (iii) any combination of two of the amino acid sequences under (i), and/or under (ii); and
(c) an internal cross-linking between at least two non-contiguous amino acids of the amino acid sequence under b);
wherein said mimetic peptide is capable of specifically binding to an anti-ApoA-I antibody.

In one embodiment, the mimetic peptides mentioned above have between 20 and 55, particularly between 25 and 55, more particularly between 25 and 40 amino acids in length.

In another embodiment, the mimetic peptides mentioned above have between 20 and 40; 21 and 40; 22 and 40; 23 and 40; 24 and 40; 25 and 40; 26 and 40; 27 and 40; 28 and 40; or 30 and 40 amino acids in length.

In another embodiment, the mimetic peptides mentioned above have 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, or 80 amino acids in length. In particular, the mimetic peptides according to the invention have 17, 18, 22, 26, 28, 32, 37, 38, 39, 40, 42, 44, or 55 amino acids.

In one embodiment, the amino acid sequence of the mimetic peptide according to the invention comprises (i) any one of SEQ ID NO: 2, SEQ ID NO: 3, SEQ ID NO: 4, SEQ ID NO: 5, SEQ ID NO: 21, SEQ ID NO: 23, SEQ ID NO: 6, SEQ ID NO: 7, SEQ ID NO: 8 and SEQ ID NO: 9, or a variant thereof, or (ii) a combination of two sequences selected from SEQ ID NO: 2, SEQ ID NO: 3, SEQ ID NO: 4, SEQ ID NO: 5, SEQ ID NO: 21, SEQ ID NO: 23, SEQ ID NO: 6, SEQ ID NO: 7, SEQ ID NO: 8 and SEQ ID NO: 9, or a variant thereof.

In another embodiment, the amino acid sequence of the mimetic peptide according to the invention comprises (i) any one of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 22, SEQ ID NO: 24, and SEQ ID NO: 18, or a variant thereof, or (ii) a combination of two sequences selected from SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 22, SEQ ID NO: 24; or a variant thereof.

In one embodiment, the amino acid sequence of the mimetic peptide according to the invention consists of (i) any one of SEQ ID NO: 2, SEQ ID NO: 3, SEQ ID NO: 4, SEQ ID NO: 5, SEQ ID NO: 21, SEQ ID NO: 23, SEQ ID NO: 6, SEQ ID NO: 7, SEQ ID NO: 8 and SEQ ID NO: 9, or a variant thereof, or (ii) a combination of two sequences selected from SEQ ID NO: 2, SEQ ID NO: 3, SEQ ID NO: 4, SEQ ID NO: 5, SEQ ID NO: 21, SEQ ID NO: 23, SEQ ID NO: 6, SEQ ID NO: 7, SEQ ID NO: 8 and SEQ ID NO: 9, or a variant thereof.

In another embodiment, the amino acid sequence of the mimetic peptide according to the invention consists of (i) any one of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 22, SEQ ID NO: 24, and SEQ ID NO: 18, or a variant thereof, or (ii) a combination of two sequences selected from SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 22, and SEQ ID NO: 24; or a variant thereof.

In another embodiment, the amino acid sequence of the mimetic peptide according to the invention comprises any one of SEQ ID NO: 8 or SEQ ID NO: 9; or a variant thereof.

In another embodiment, the amino acid sequence of the mimetic peptide according to the invention comprises SEQ ID NO: 25; or a variant thereof.

In another particular embodiment, the amino acid sequence of the mimetic peptide according to the invention consists of any one of SEQ ID NO: 8 or SEQ ID NO: 9; or a variant thereof.

In another embodiment, the amino acid sequence of the mimetic peptide according to the invention consists of SEQ ID NO: 25; or a variant thereof.

In another embodiment, the amino acid sequence of the mimetic peptide according to the invention comprises SEQ ID NO: 5; or a variant thereof.

In another embodiment, the amino acid sequence of the mimetic peptide according to the invention comprises SEQ ID NO: 5 with the deletion of the last two amino acids E and N at the C-terminal part of SEQ ID NO: 5.

In another embodiment, the amino acid sequence of the mimetic peptide according to the invention comprises SEQ ID NO: 21; or a variant thereof.

In another particular embodiment, the amino acid sequence of the mimetic peptide according to the invention consists of SEQ ID NO: 5; or a variant thereof.

In another embodiment, the amino acid sequence of the mimetic peptide according to the invention consists of SEQ ID NO: 5 with the deletion of the last two amino acids E and N at the C-terminal part of SEQ ID NO: 5.

In another particular embodiment, the amino acid sequence of the mimetic peptide according to the invention consists of SEQ ID NO: 21; or a variant thereof.

In another embodiment, the amino acid sequence of the mimetic peptide according to the invention comprises or consists of SEQ ID NO: 23, or consists of SEQ ID NO: 23 with the addition of 1, 2, 3, 4, 5, or 6 amino acids, in particular 5 amino acids.

In a still other embodiment, the amino acid sequence of the mimetic peptide according to the invention comprises any one of SEQ ID NO: 15, SEQ ID NO 16, SEQ ID NO: 17, SEQ ID NO: 19, SEQ ID NO: 20; or a variant thereof.

In a still other embodiment, the amino acid sequence of the mimetic peptide according to the invention comprises SEQ ID NO: 19; or a variant thereof.

In another particular embodiment, the amino acid sequence of the mimetic peptide according to the invention consists of any one of SEQ ID NO: 15, SEQ ID NO 16, SEQ ID NO: 17, SEQ ID NO: 19, SEQ ID NO: 20; or a variant thereof.

In another particular embodiment, the amino acid sequence of the mimetic peptide according to the invention consists of SEQ ID NO: 19; or a variant thereof.

In a still other embodiment, the amino acid sequence of the mimetic peptide according to the invention comprises SEQ ID NO: 13, SEQ ID NO: 22 or SEQ ID NO: 24, or a variant thereof.

In another particular embodiment, the amino acid sequence of the mimetic peptide according to the invention consists of any one of SEQ ID NO: 13, SEQ ID NO: 22 or SEQ ID NO: 24, or a variant thereof.

In a still other embodiment, the amino acid sequence of the mimetic peptide according to the invention comprises or consists of SEQ ID NO: 13.

In a particular embodiment, the amino acid sequence of the mimetic peptide according to the invention comprises SEQ ID NO: 18, or a variant thereof.

In another particular embodiment, the amino acid sequence of the mimetic peptide according to the invention consists of SEQ ID NO: 18, or a variant thereof.

In another embodiment, the peptide according to the invention has an amino acid sequence as mentioned above except that 1, 2, 3, 4, 5 or 6 amino acids of said sequence are substituted, deleted, and/or inserted without aborting the capacity of said mimetic peptide to specifically bind to an anti-ApoA-I antibody.

In a particular embodiment of the invention, 1, 2, 3, 4, 5 or 6 amino acids of said sequence are substituted by amino acids residues suitable for establishing the internal cross-linking, such as Glutamic acid (E) residue and/or a Lysine (K) residue for establishing a lactam-bridge or such as Cysteine (C) residue(s) for establishing a disulfide bridge.

Optionally, 2, 4, or 6 amino acids contained in the amino acid sequence of the mimetic peptide of the invention are chemically modified for establishing the internal cross-linking, without aborting the capacity of said mimetic peptide to specifically bind to an anti-ApoA-I antibody. For instance, in a particular embodiment, at least two, for instance 2 or 4, amino acid residues such as Phenylalanine (F), Leucine (L), Methionine (M), Valine (V), Lysine (K), and Tyrosine (Y), contained within the amino acid sequence of the peptide according to the invention are substituted in alanine residues and said alanine residues are chemically modified into (S)-2-(4'-pentenyl)-Alanine or (R)-2-(7'-octenyl)-Alanine so as to establish a hydrocarbon staple between two of the chemically modified Alanine residues.

In another embodiment, the N-terminal and/or C-terminal ends of the mimetic peptide of the invention are further modified to remove the possible electric charge of the free amino and/or carboxy termini, respectively. In a particular embodiment, the free amino group at the N-terminal end of said peptide is covalently attached to an acyl group (such as acetyl, propionyl, palmitoyl, etc). In another embodiment, the free carboxy group at the C-terminal end of said peptide is amidated. In a further embodiment, both N-terminal and C-terminal ends of the mimetic peptide are modified, in particular the free amino group at the N-terminal end of said peptide is covalently attached to an acyl group (such as acetyl, propionyl, palmitoyl, etc) and the free carboxy group at the C-terminal end of said peptide is amidated.

Figure 1:
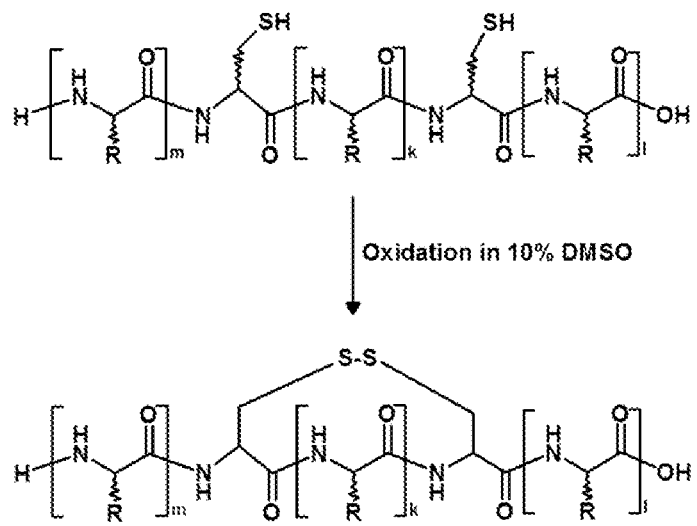
FIG. 1. Chemical reaction for making a disulfide bridge within a peptide according to the invention in solution (A), a hydrocarbon staple within a peptide according to the invention using Fmoc-based solid-phase peptide synthesis (B), or a lactam bridge within a peptide according to the invention on solid phase (C). "DMSO" is dimethyl sulfoxide, "PyBOP" is benzotriazol-1-yl-oxytripyrrolidinophosphonium hexafluorophosphate, "DIEA" is N,N-Diisopropylethylamine, "alloc group" is allyloxycarbonyl group, "allyl group" has the structural formula $H_2C=CH—CH_2—$. Next to the brackets, m, k, and l refer to the positions of the amino acids on the peptide sequence.
Figure 1:
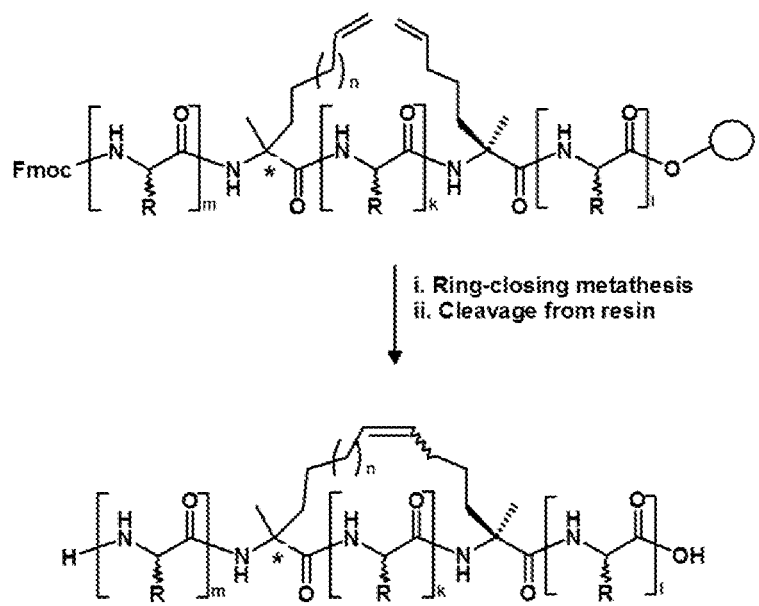
Figure 1:
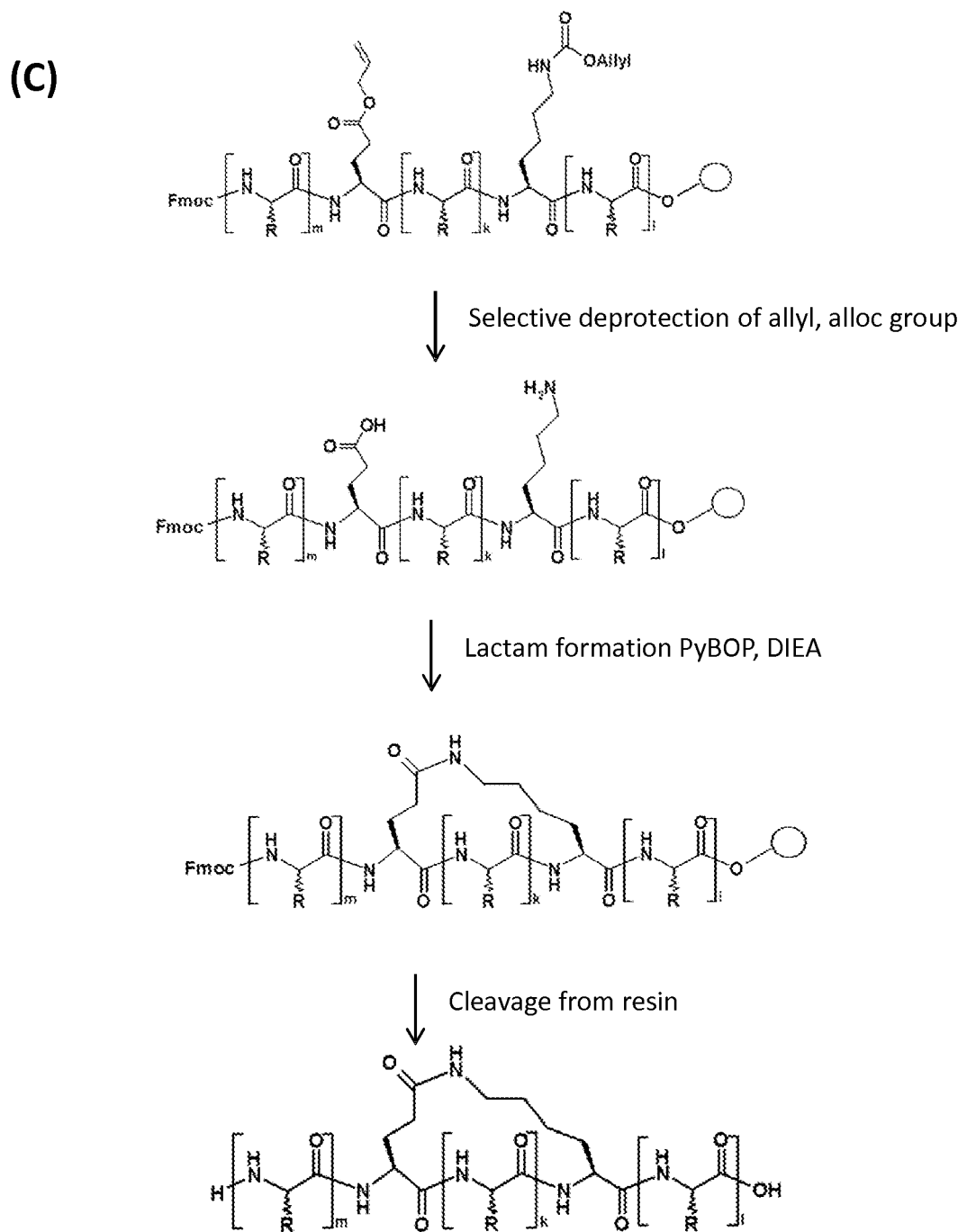
Figure 2:
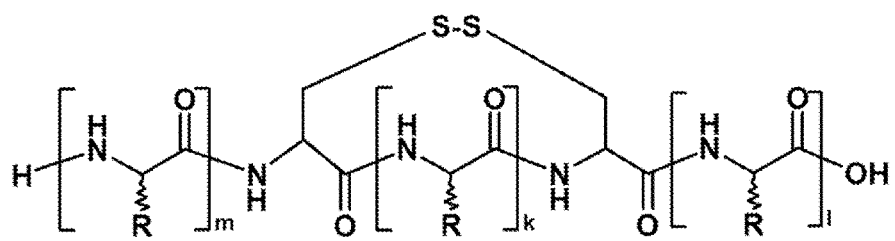
FIG. 2: Developed chemical formula of examples of internal cross-linking within a peptide according to the invention: disulfide bridge (A), hydrocarbon staple (B), lactam bridge (C). In (A): k is 3 or 6, R is any amino acid side chain; in (B): for a cross-linking between residues at n and n+4 positions, k is 3, n is 1, * is (S)-2-(4'-pentenyl)-
Figure 2:
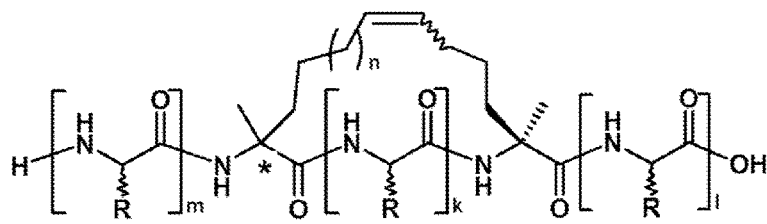
Figure 2:
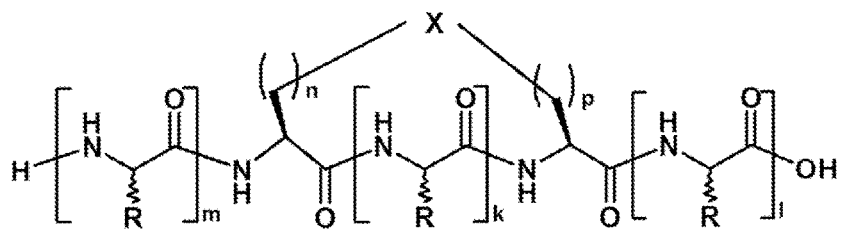

In a further embodiment of the invention, the internal cross-linking between 2 non-contiguous amino acids contained in the amino acid sequence of the mimetic peptide mentioned above is carried out via covalent linkage such as lactam-bridge, hydrocarbon staple, disulfide bridge, or any other rigid linker between said 2 non-contiguous amino acid residues such as those produced by the main-chain hydrogen-bond surrogate stabilization (Chapman et al, *J Am Chem Soc*, 2004, 126: 12252-12253) or those depicted in FIGS. 1 and 2.

In one embodiment of the invention, the amino acid residues of the peptide which are cross-linked are located at position n and n+3, n+4, n+5, n+6, n+7, n+8, n+9, n+10, n+11, respectively. It is understood that the positions refer to the primary amino acid sequence of the peptide, i.e. the respective positions of the amino acid residues in the primary structure of the peptide, and that "n" indicates the position of one of the amino acid residue, "n+3" indicates that the other amino acid residue is located 3 amino acids further to the n position on the amino acid sequence of the peptide, "n+4" indicates that the other amino acid residue is located 4 amino acids further to the n position on the amino acid sequence of the peptide, "n+5" indicates that the other amino acid residue is located 5 amino acids further to the n position on the amino acid sequence of the peptide, etc.

In a particular embodiment of the invention, a disulfide bridge is established between a Cystein (C) residue at position n within the peptide sequence and another Cystein (C) residue at position n+3 of said peptide sequence. The chemical reaction for making a disulfide bridge within a peptide in solution is represented in FIG. 1A. The disulfide bridge within a peptide is represented in FIG. 2A.

In another particular embodiment of the invention, a hydrocarbon staple is established between chemically modified Alanine (A) at position n within the peptide sequence and another chemically modified Alanine (A) at position n+4, or n+7, of said peptide sequence. In particular, the hydrocarbon staple is established between modified Alanine residues which include α-disubstituted aminoacids such as 2-aminoisobutyric acid, (S)-2-(4'-pentenyl)-Alanine and (R)-2-(7'-octenyl)-Alanine. In a further embodiment, the internal cross-linking is a hydrocarbon staple between one (S)-2-(4'-pentenyl)-Alanine and one (R)-2-(7'-octenyl)-Alanine. In another embodiment, the internal cross-linking is a hydrocarbon staple between two (S)-2-(4'-pentenyl)-Alanines. In an alternative embodiment, a hydrocarbon staple is established between chemically modified Alanine (A) at position n within the peptide sequence and another chemically modified Alanine (A) at position n+3, of said peptide sequence.

The chemical reaction for making a hydrocarbon staple within a peptide using Fmoc-based solid-phase peptide synthesis is represented in FIG. 1B. The hydrocarbon staple within a peptide is represented in FIG. 2B.

Examples of hydrocarbon staples useful in the invention include those depicted in FIG. 2B. For instance, a hydrocarbon staple can link two amino acids Xaa at positions n and n+7, wherein Xaa at position n is a modified alanine of formula (I): —NH—C(CH$_3$)(R)—C(O)— wherein R is a hydrocarbon staple —(CH$_2$)$_6$—CH═CH—(CH$_2$)$_3$— linked to a subsequent Xaa at position n+7, and wherein Xaa at position n+7 is a modified alanine of formula (I): —NH—C(CH$_3$)(R')—C(O)— wherein R' is a single bond linked to the hydrocarbon staple from Xaa at position n as defined above. As other example, a hydrocarbon staple can link two amino acids Xaa at positions n and n+4, wherein Xaa at position n is a modified alanine of formula (I): —NH—C(CH$_3$)(R)—C(O)— wherein R is a hydrocarbon staple —(CH$_2$)$_3$—CH═CH—(CH$_2$)$_3$— linked to a subsequent Xaa at position n+4, and wherein Xaa at position n+4 is a modified alanine of formula (I): —NH—C(CH$_3$)(R')—C(O)— wherein R' is a single bond linked to the hydrocarbon staple from Xaa at position n as defined above.

In a particular embodiment of the invention, a lactam bridge is established between a Glutamic acid (E) residue at position n within the peptide sequence and a Lysine (K) residue at position n+4 or n+7, preferably at position n+4, of said peptide sequence.

In another embodiment, a lactam bridge is established between a Lysine (K) residue at position n within the peptide sequence and a Glutamic acid (E) residue at position n+4 or n+7, preferably at position n+4, of said peptide sequence.

The chemical reaction for making a lactam bridge within a peptide on solid phase is represented in FIG. 1C. The lactam bridge within a peptide is represented in FIG. 2C.

Examples of lactam bridges useful in the invention include those depicted in FIG. 2C. For instance, a Lactam bridge formed between two amino acids Xaa at positions n and n+4 on the peptide sequence, wherein Xaa at position n is a modified amino acid of formula (I): —NH—C(H)(R)—C(O)— wherein R is a lactam bridge —(CH$_2$)$_2$—CO—NH—(CH$_2$)$_4$-linked to a subsequent residue at position n+4, and wherein Xaa at position n+4 is a modified amino acid of formula (I): —NH—C(H)(R')—C(O)— wherein R' is a single bond linked to the lactam bridge from Xaa at position n as defined above. Another example is a lactam bridge formed between two amino acids Xaa at n and n+4 on the peptide sequence, wherein Xaa at position n is a modified amino acid of formula (I): —NH—C(H)(R)—C(O)— wherein R is a lactam bridge —(CH$_2$)$_4$—NH—CO—(CH$_2$)$_2$— linked to a subsequent Xaa at position n+4, and wherein Xaa at position n+4 is a modified amino acid of formula (I): —NH—C(H)(R')—C(O)— wherein R' is a single bond linked to the lactam bridge from Xaa at position n as defined above.

In a further embodiment, the mimetic peptide according to the invention is selected among the peptides represented in Table 2 below, wherein internal cross-linking is performed either via a lactam bridge between the underlined Glutamic acid (E) and Lysine (K) residues or via an hydrocarbon staple between R8 and S5 wherein R$_8$ corresponds to (R)-2-(7'-octenyl)-Alanine and S$_5$ corresponds to (S)-2-(4'-pentenyl)-Alanine

TABLE 2

Examples of mimetic peptides according to the invention and their amino acid sequence. $R_8$ corresponds to (R)-2-(7'-octenyl)-Alanine and $S_5$ corresponds to (S)-2-(4'-pentenyl)-Alanine which are engaged in a hydrocarbon staple according to FIG. 2B. Underlined E and K are amino acids engaged in a lactam bridge according to FIG. 2C. Optionally, the peptides according to the invention have the free amino group at the N-terminal end acetylated and the free carboxy group at the C-terminal end amidated.

VKDLR$_8$TVYVDVS$_5$KDSGRDYVSQFEGSAL
with a hydrocarbon staple of FIG. 2B linking R8 at position 5 and S5 at position 12
which is represented by SEQ ID NO: 10

DSVTSTR$_8$SKLREQS$_5$GPVTQEFWDNLEKETEGL
with a hydrocarbon staple of FIG. 2B linking R8 at position 7 and S5 at position 14
which is represented by SEQ ID NO: 11

YLDDFQKKWQEER$_8$ELYRQKS$_5$EPLRAELQEGARQKLHEL
with a hydrocarbon staple of FIG. 2B linking R8 at position 13 and S5 at position 20
which is represented by SEQ ID NO: 12

EEMRDRARAHR$_8$DALRTHS$_5$APYSDELRQRLAARLEALKEN
with a hydrocarbon staple of FIG. 2B linking R8 at position 11 and S5 at position 18
which is represented by SEQ ID NO: 13

ATEHR$_8$STLSEKS$_5$KPALED
with a hydrocarbon staple of FIG. 2B linking R8 at position 5 and S5 at position 12
which is represented by SEQ ID NO: 14

GLLPVLESFKVSFLSALE<u>E</u>YTK<u>K</u>LNT
with a lactam bridge of FIG. 2C linking the E at position 19 and K at position 23
which is represented by SEQ ID NO: 19

GLLPVLESFKVSFLSR$_8$LEEYTKS$_5$LNT
with a hydrocarbon staple of FIG. 2B linking R8 at position 16 and S5 at position 23
which is represented by SEQ ID NO: 15

GLLPVLESFKVSS$_5$LSAS$_5$EEYTKKLNT
with a hydrocarbon staple of FIG. 2B linking S5 at position 13 and S5 at position 17
which is represented by SEQ ID NO: 16

VLESFKVSR$_8$LSALEES$_5$TKKLNT
with a hydrocarbon staple of FIG. 2B linking R8 at position 9 and S5 at position 16
which is represented by SEQ ID NO: 17

VLESFKVSFLSALE<u>E</u>YTK<u>K</u>LNT
with a lactam bridge of FIG. 2C linking the E at position 15 and K at position 19 on said sequence
which is represented by SEQ ID NO: 20

CAEYHAKATEHLSTLSEKAKPALEDLR§GLLPVLESFKVSFLSALE<u>E</u>YTK<u>K</u>LN
TC with § = Gln analogue at position 28 (side chain $CH_2$-S-$CH_2$-$CONH_2$ instead of $CH_2$-$CH_2$-$CONH_2$) and a lactam bridge of FIG. 2C linking the E at position 47 and K at position 51
which is represented by SEQ ID NO: 18

VKDL<u>Xaa</u>TVYVDV<u>Xaa</u>KDSGRDYVSQFEGSAL (SEQ ID NO: 10 wherein Xaa at
position 5 is substituted into a modified alanine of formula (I): —NH—C($CH_3$)(R)—C(O)—
wherein R is a hydrocarbon staple -($CH_2$)$_6$-CH=CH-($CH_2$)$_3$- linked to a subsequent
Xaa at position 12, and wherein Xaa at position 12 is a modified alanine of formula
(I): —NH—C($CH_3$)(R')—C(O)— wherein R' is a single bond linked to the hydrocarbon
staple from Xaa at position 5 as defined above)

DSVTST<u>Xaa</u>SKLREQ<u>Xaa</u>GPVTQEFWDNLEKETEGL (SEQ ID NO: 11 wherein
Xaa at position 7 is a modified alanine of formula (I): —NH—C($CH_3$)(R)—C(O)— wherein
R is a hydrocarbon staple —($CH_2$)$_6$—CH=CH—($CH_2$)$_3$— linked to a subsequent Xaa at
position 14, and wherein Xaa at position 14 is a modified alanine of formula (I): —NH—
C($CH_3$)(R')—C(O)— wherein R' is a single bond linked to the hydrocarbon staple from
Xaa at position 7 as defined above)

YLDDFQKKWQEE<u>Xaa</u>ELYRQK<u>Xaa</u>EPLRAELQEGARQKLHEL (SEQ ID NO: 12
wherein Xaa at position 13 is a modified alanine of formula (I): —NH—C($CH_3$)(R)—
C(O)— wherein R is a hydrocarbon staple —($CH_2$)$_6$—CH=CH—($CH_2$)$_3$— linked to a
subsequent Xaa at position 20, and wherein Xaa at position 20 is a modified alanine
of formula (I): —NH—C($CH_3$)(R')—C(O)— wherein R' is a single bond linked to the
hydrocarbon staple from Xaa at position 13 as defined above)

TABLE 2-continued

Examples of mimetic peptides according to the invention and their amino acid sequence. $R_8$ corresponds to (R)-2-(7'-octenyl)-Alanine and $S_5$ corresponds to (S)-2-(4'-pentenyl)-Alanine which are engaged in a hydrocarbon staple according to FIG. 2B. Underlined E and K are amino acids engaged in a lactam bridge according to FIG. 2C. Optionally, the peptides according to the invention have the free amino group at the N-terminal end acetylated and the free carboxy group at the C-terminal end amidated.

EEMRDRARAHXaaDALRTHXaaAPYSDELRQRLAARLEALKEN (SEQ ID NO: 13 wherein Xaa at position 11 is a modified alanine of formula (I): —NH—C(CH₃)(R)—C(O)— wherein R is a hydrocarbon staple —(CH₂)₆—CH=CH-(CH₂)₃— linked to a subsequent Xaa at position 18, and wherein Xaa at position 18 is a modified alanine of formula (I): —NH—C(CH₃)(R')—C(O)— wherein R' is a single bond linked to the hydrocarbon staple from Xaa at position 11 as defined above)

LSPLGEEMRDRARAHXaaDALRTHXaaAPYSDELRQRLAARLEALK (SEQ ID NO: 22, wherein Xaa at position 16 is a modified alanine of formula (I): —NH—C(CH₃)(R)—C(O)— wherein R is a hydrocarbon staple —(CH₂)₆—CH=CH-(CH₂)₃— linked to a subsequent Xaa at position 23, and wherein Xaa at position 23 is a modified alanine of formula (I): —-NH—C(CH₃)(R')—C(O)— wherein R' is a single bond linked to the hydrocarbon staple from Xaa at position 16 as defined above)

EEMRDRARAHXaaDALRTHXaaAPYSDELRQRLAARLEALK (SEQ ID NO: 24 wherein Xaa at position 11 is a modified alanine of formula (I): —NH—C(CH₃)(R)—C(O)— wherein R is a hydrocarbon staple —(CH₂)₆—CH=CH-(CH₂)₃— linked to a subsequent Xaa at position 18, and wherein Xaa at position 18 is a modified alanine of formula (I): —NH—C(CH₃)(R')—C(O)— wherein R' is a single bond linked to the hydrocarbon staple from Xaa at position 11 as defined above)

ATEHXaaSTLSEKXaaKPALED (SEQ ID NO: 14 wherein Xaa at position 5 is a modified alanine of formula (I): —NH-C(CH₃)(R)—C(O)— wherein R is a hydrocarbon staple —(CH₂)₆—CH=CH-(CH₂)₃— linked to a subsequent Xaa at position 12, and wherein Xaa at position 12 is a modified alanine of formula (I): —NH—C(CH₃)(R')—C(O)— wherein R' is a single bond linked to the hydrocarbon staple from Xaa at position 5 as defined above)

GLLPVLESFKVSFLSALEXaaYTKXaaLNT (SEQ ID NO: 19 wherein Xaa at position 19 is a modified amino acid of formula (I): —NH—C(H)(R)—C(O)— wherein R is a lactam bridge —(CH₂)₂—CO—NH—(CH₂)₄— linked to a subsequent Xaa at position 23, and wherein Xaa at position 23 is a modified amino acid of formula (I): —NH—C(H)(R')—C(O)— wherein R' is a single bond linked to the lactam bridge from Xaa at position 19 as defined above)

GLLPVLESFKVSFLSXaaLEEYTKXaaLNT (SEQ ID NO: 15 wherein Xaa at position 16 is a modified alanine of formula (I): —NH—C(CH₃)(R)—C(O)— wherein R is a hydrocarbon staple -(CH₂)₆-CH=CH-(CH₂)₃- linked to a subsequent Xaa at position 23, and wherein Xaa at position 23 is a modified alanine of formula (I): —NH—C(CH₃)(R')—C(O)— wherein R' is a single bond linked to the hydrocarbon staple from Xaa at position 16 as defined above)

GLLPVLESFKVSXaaLSAXaaEEYTKKLNT (SEQ ID NO: 16 wherein Xaa at position 13 is a modified alanine of formula (I): —NH—C(CH₃)(R)—C(O)— wherein R is a hydrocarbon staple -(CH₂)₃-CH=CH-(CH₂)₃- linked to a subsequent Xaa at position 17, and wherein Xaa at position 17 is a modified alanine of formula (I): —NH—C(CH₃)(R')—C(O)— wherein R' is a single bond linked to the hydrocarbon staple from Xaa at position 13n as defined above)

VLESFKVSXaaLSALEEXaaTKKLNT (SEQ ID NO: 17 wherein Xaa at position 9 is a modified alanine of formula (I): —NH—C(CH₃)(R)—C(O)— wherein R is a hydrocarbon staple —(CH₂)₆—CH=CH-(CH₂)₃— linked to a subsequent Xaa at position 16, and wherein Xaa at position 16 is a modified alanine of formula (I): —NH—C(CH₃)(R')—C(O)— wherein R' is a single bond linked to the hydrocarbon staple from Xaa at position 9 as defined above)

VLESFKVSFLSALEXaaYTKXaaLNT (SEQ ID NO: 20 wherein Xaa at position 15 is a modified amino acid of formula (I): —NH—C(H)(R)—C(O)— wherein R is a lactam bridge —(CH₂)₂—CO—NH—(CH₂)₄— linked to a subsequent Xaa at position 19, and wherein Xaa at position 19 is a modified amino acid of formula (I): —NH—C(H)(R')—C(O)— wherein R' is a single bond linked to the lactam bridge from Xaa at position 15 as defined above)

CAEYHAKATEHLSTLSEKAKPALEDLRXaaGLLPVLESFKVSFLSALEXaaYTKXaaLNTC (SEQ ID NO: 18 wherein Xaa at position 28 is a Gln analogue having $CH_2$-S-$CH_2$-$CONH_2$ as side chain, wherein Xaa at position 47 is a modified amino acid of formula (I): —NH—C(H)(R)—C(O)— wherein R is a lactam bridge —(CH₂)₂—CO—NH—(CH₂)₄— linked to a subsequent Xaa at position 51, and wherein Xaa at position 51 is a modified amino acid of formula (I): —NH—C(H)(R')—C(O)— wherein R' is a single bond linked to the lactam bridge from Xaa at position 47 as defined above)

In a particular embodiment, the amino acid sequence of the mimetic peptide according to the invention comprises SEQ ID NO: 8 or SEQ ID NO: 9; or a variant thereof.

In a particular embodiment, the amino acid sequence of the mimetic peptide according to the invention comprises SEQ ID NO: 25; or a variant thereof.

In another particular embodiment, the amino acid sequence of the mimetic peptide according to the invention comprises SEQ ID NO: 5, or a variant thereof.

In another embodiment, the amino acid sequence of the mimetic peptide according to the invention comprises SEQ ID NO: 5 with the deletion of the last two amino acids E and N at the C-terminal part of SEQ ID NO: 5.

In another particular embodiment, the amino acid sequence of the mimetic peptide according to the invention comprises SEQ ID NO: 21 or SEQ ID NO: 23; or a variant thereof.

In another particular embodiment, the amino acid sequence of the mimetic peptide according to the invention comprises SEQ ID NO: 15, SEQ ID NO: 16, SEQ ID NO: 17, SEQ ID NO: 19, or SEQ ID NO: 20; or a variant thereof.

In another embodiment, the mimetic peptide according to the invention comprises SEQ ID NO: 15 with the free amino group at the N-terminal end acetylated and/or free carboxy group at the C-terminal end amidated, more particularly with the free amino group at the N-terminal end acetylated and the free carboxy group at the C-terminal end amidated.

In another embodiment, the mimetic peptide according to the invention comprises SEQ ID NO: 16 with the free amino group at the N-terminal end acetylated and/or free carboxy group at the C-terminal end amidated, more particularly with the free amino group at the N-terminal end acetylated and the free carboxy group at the C-terminal end amidated.

In another embodiment, the mimetic peptide according to the invention comprises SEQ ID NO: 17 with the free amino group at the N-terminal end acetylated and/or free carboxy group at the C-terminal end amidated, more particularly with the free amino group at the N-terminal end acetylated and the free carboxy group at the C-terminal end amidated.

In another embodiment, the mimetic peptide according to the invention comprises SEQ ID NO: 19 with the free amino group at the N-terminal end acetylated and/or the free carboxy group at the C-terminal end amidated, more particularly with the free amino group at the N-terminal end acetylated and free carboxy group at the C-terminal end amidated.

In another embodiment, the mimetic peptide according to the invention comprises SEQ ID NO: 20 with the free amino group at the N-terminal end acetylated and/or the free carboxy group at the C-terminal end amidated, more particularly with the free amino group at the N-terminal end acetylated and the free carboxy group at the C-terminal end amidated.

In another particular embodiment, the amino acid sequence of the mimetic peptide according to the invention comprises SEQ ID NO: 13, SEQ ID NO: 22 or SEQ ID NO: 24.

In a particular embodiment, the mimetic peptide according to the invention comprises SEQ ID NO: 13 with the free amino group at the N-terminal end acetylated and/or the free carboxy group at the C-terminal end amidated, more particularly with the free amino group at the N-terminal end acetylated and free carboxy group at the C-terminal end amidated.

In another particular embodiment, the mimetic peptide according to the invention comprises SEQ ID NO: 22 with the free amino group at the N-terminal end acetylated and/or the free carboxy group at the C-terminal end amidated, more particularly with the free amino group at the N-terminal end acetylated and free carboxy group at the C-terminal end amidated.

In a particular embodiment, the mimetic peptide according to the invention comprises SEQ ID NO: 24 with the free amino group at the N-terminal end acetylated and/or the free carboxy group at the C-terminal end amidated, more particularly with the free amino group at the N-terminal end acetylated and free carboxy group at the C-terminal end amidated.

In a further particular embodiment, the amino acid sequence of the mimetic peptide according to the invention comprises any one of:
  (i) SEQ ID NO: 19 with a lactam bridge of FIG. 2C linking the E at position 19 and K at position 23;
  (ii) SEQ ID NO: 15 with a hydrocarbon staple of FIG. 2B linking (R)-2-(7'-octenyl)-Alanine at position 16 and (S)-2-(4'-pentenyl)-Alanine at position 23;
  (iii) SEQ ID NO: 16 with a hydrocarbon staple of FIG. 2B linking (S)-2-(4'-pentenyl)-Alanine at position 13 and (S)-2-(4'-pentenyl)-Alanine at position 17;
  (iv) SEQ ID NO: 17 with a hydrocarbon staple of FIG. 2B linking (R)-2-(7'-octenyl)-Alanine at position 9 and (S)-2-(4'-pentenyl)-Alanine at position 16.

In a further particular embodiment, the amino acid sequence of the mimetic peptide according to the invention comprises any one of SEQ ID NO: 15, SEQ ID NO: 16, SEQ ID NO: 17, SEQ ID NO: 19 or SEQ ID NO: 20; or a variant thereof.

In a further particular embodiment, the amino acid sequence of the mimetic peptide according to the invention comprises any one of SEQ ID NO: 13, SEQ ID NO: 22, or SEQ ID NO: 24; or a variant thereof.

In a still further particular embodiment, the amino acid sequence of the mimetic peptide according to the invention consists of any one of:
  (i) SEQ ID NO: 19 with a lactam bridge of FIG. 2C linking the E at position 19 and K at position 23;
  (ii) SEQ ID NO: 15 with a hydrocarbon staple of FIG. 2B linking (R)-2-(7'-octenyl)-Alanine at position 16 and (S)-2-(4'-pentenyl)-Alanine at position 23;
  (iii) SEQ ID NO: 16 with a hydrocarbon staple of FIG. 2B linking (S)-2-(4'-pentenyl)-Alanine at position 13 and (S)-2-(4'-pentenyl)-Alanine at position 17;
  (iv) SEQ ID NO: 17 with a hydrocarbon staple of FIG. 2B linking (R)-2-(7'-octenyl)-Alanine at position 9 and (S)-2-(4'-pentenyl)-Alanine at position 16;

In a further particular embodiment, the amino acid sequence of the mimetic peptide according to the invention consists of any one of SEQ ID NO: 15, SEQ ID NO: 16, SEQ ID NO: 17, SEQ ID NO: 19 or SEQ ID NO: 20; or a variant thereof.

In a further particular embodiment, the amino acid sequence of the mimetic peptide according to the invention consists of any one of SEQ ID NO: 13, SEQ ID NO: 22 or SEQ ID NO: 24; or a variant thereof.

In another aspect, the mimetic peptide of the invention has no internal cross-linking.

In one embodiment, the invention relates to a mimetic peptide of an epitope of Apolipoprotein A-I (ApoA-I), wherein said mimetic peptide has:
  (a) an amino acid sequence of 15 to 80 amino acids in length,
  (b) an amino acid sequence comprising any one of:
    (i) SEQ ID NO: 5, SEQ ID NO: 21, SEQ ID NO: 23; or a variant thereof, or (ii) SEQ ID NO: 8, SEQ ID NO: 9, SEQ ID NO: 25; or a variant thereof, or (iii) an amino acid sequence identical to any one of the sequences under (i) or (ii) except that 1, 2, 3, 4, 5, or 6 amino acids of said sequence under (i) or (ii) are substituted, deleted, inserted, and/or chemically modified, without aborting the capacity of said mimetic peptide to specifically bind to an anti-ApoA-I antibody, or (iv) any combination of two of the amino acid sequences under (i), (ii), and/or under (iii);

wherein said mimetic peptide is capable of specifically binding to an anti-ApoA-I antibody.

In one embodiment, the mimetic peptides mentioned above have between 20 and 55, particularly between 25 and 55, more particularly between 25 and 40 amino acids in length.

In another embodiment, the mimetic peptides mentioned above have between 20 and 40; 21 and 40; 22 and 40; 23 and 40; 24 and 40; 25 and 40; 26 and 40; 27 and 40; 28 and 40; or 30 and 40 amino acids in length.

In another embodiment, the mimetic peptides mentioned above have 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, or 80 amino acids in length. In particular, the mimetic peptides according to the invention have 17, 18, 22, 26, 28, 32, 37, 38, 39, 40, 42, 44, or 55 amino acids.

In another embodiment, the N-terminal and/or C-terminal ends of the mimetic peptide of the invention are further modified to remove the possible electric charge of the free amino and/or carboxy termini, respectively. In a particular embodiment, the free amino group at the N-terminal end of said peptide is covalently attached to an acyl group (such as acetyl, propionyl, palmitoyl, etc). In another embodiment, the free carboxy group at the C-terminal end of said peptide is amidated. In a further embodiment, both N-terminal and C-terminal ends of the mimetic peptide are modified, in particular the free amino group at the N-terminal end of said peptide is covalently attached to an acyl group (such as acetyl, propionyl, palmitoyl, etc) and the free carboxy group at the C-terminal end of said peptide is amidated.

In a particular embodiment, said mimetic peptide according to the invention comprises SEQ ID NO: 5, SEQ ID NO: 21, or SEQ ID NO: 23.

In another embodiment, said mimetic peptide comprises SEQ ID NO: 5 with the deletion of the last two amino acids E and N at the C-terminal part of SEQ ID NO: 5.

In a particular embodiment, the mimetic peptide according to the invention comprises SEQ ID NO: 5, or variant thereof, with the free amino group at the N-terminal end acetylated and/or the free carboxy group at the C-terminal end amidated, more particularly, with the free amino group at the N-terminal end acetylated and the free carboxy group at the C-terminal end amidated.

In a particular embodiment, the mimetic peptide according to the invention comprises SEQ ID NO: 21, or variant thereof, with the free amino group at the N-terminal end acetylated and/or the free carboxy group at the C-terminal end amidated, more particularly, with the free amino group at the N-terminal end acetylated and the free carboxy group at the C-terminal end amidated.

In a particular embodiment, the mimetic peptide according to the invention comprises SEQ ID NO: 23, or variant thereof, with the free amino group at the N-terminal end acetylated and/or the free carboxy group at the C-terminal end amidated, more particularly, with the free amino group at the N-terminal end acetylated and the free carboxy group at the C-terminal end amidated.

In a particular embodiment, said mimetic peptide comprises SEQ ID NO: 8, SEQ ID NO: 9 or SEQ ID NO: 25.

In another particular embodiment, the mimetic peptide according to the invention comprises SEQ ID NO: 8, or variant thereof, with the free amino group at the N-terminal end acetylated and/or free carboxy group at the C-terminal end amidated, more particularly with the free amino group at the N-terminal end acetylated and the free carboxy group at the C-terminal end amidated.

In another particular embodiment, the mimetic peptide according to the invention comprises SEQ ID NO: 9, or variant thereof, with the free amino group at the N-terminal end acetylated and/or free carboxy group at the C-terminal end amidated, more particularly with the free amino group at the N-terminal end acetylated and the free carboxy group at the C-terminal end amidated.

In another particular embodiment, the mimetic peptide according to the invention comprises SEQ ID NO: 25, or variant thereof, with the free amino group at the N-terminal end acetylated and/or free carboxy group at the C-terminal end amidated, more particularly with the free amino group at the N-terminal end acetylated and the free carboxy group at the C-terminal end amidated.

According to another aspect, the present invention provides mimetic peptides according to the invention for use as a diagnostic composition.

In particular, the present invention provides mimetic peptides according to the invention for use in the diagnosis and/or prognosis of a cardiovascular disease.

In another embodiment, the present invention provides mimetic peptides according to the invention for use as a medicament.

In another embodiment, the present invention provides mimetic peptides according to the invention for use in the treatment of a cardiovascular disease.

According to another embodiment, is provided an immunoassay preparation useful for the detection of anti-ApoA-I antibodies as biomarkers for a cardiovascular disease in a biological fluid sample, comprising at least one mimetic peptide according to the invention, or variant thereof.

According to a further embodiment, is provided an immunoassay preparation useful for the detection of anti-ApoA-I antibodies as biomarkers for a cardiovascular disease in a biological fluid sample comprising at least one mimetic peptide according to the invention or a variant thereof.

According to another embodiment, is provided a use of an immunoassay preparation according to the invention for the coating of a solid matrix for performing an immunoassay.

According to a further embodiment, is provided an immunoassay plate useful for the detection of anti-ApoA-I antibodies as biomarkers for a cardiovascular disease in a biological fluid sample comprising at least one mimetic peptide according to the invention, or variant thereof, coupled to and/or coated on a solid matrix.

Polynucleotides Encoding the Mimetic Peptides According to the Invention

Another aspect of the invention relates to isolated polynucleotides encoding the mimetic peptides according to the invention.

In a particular embodiment, the invention relates to isolated polynucleotides encoding the mimetic peptides according to the invention wherein the internal cross-linking is a disulfide bridge between two non-contiguous Cysteine residues of the amino acid sequence of said mimetic peptides.

Production and Purification of the Peptides According to the Invention

Another aspect of the invention provides a recombinant vector comprising a polynucleotide according to the invention.

Numerous expression systems can be used, including without limitation chromosomes, episomes, and derived viruses. More particularly, the recombinant vectors used can be derived from bacterial plasmids, transposons, yeast episomes, insertion elements, yeast chromosome elements, viruses such as baculovirus, papilloma viruses such as SV40, vaccinia viruses, adenoviruses, fox pox viruses, pseudorabies viruses, retroviruses.

These recombinant vectors can equally be cosmid or phagemid derivatives. The nucleotide sequence can be inserted in the recombinant expression vector by methods well known to a person skilled in the art such as, for example, those that are described in MOLECULAR CLONING: A LABORATORY MANUAL, Sambrook et al., 4th Ed., Cold Spring Harbor Laboratory Press, Cold Spring Harbor, N.Y., 2001.

The recombinant vector can include nucleotide sequences that control the regulation of the polynucleotide expression as well as nucleotide sequences permitting the expression and the transcription of a polynucleotide of the invention and the translation of a polypeptide of the invention, these sequences being selected according to the host cells that are used.

Thus, for example, an appropriate secretion signal can be integrated in the recombinant vector so that the polypeptide, encoded by the polynucleotide of the invention, will be directed towards the lumen of the endoplasmic reticulum, towards the periplasmic space, on the membrane or towards the extracellular environment. The choice of an appropriate secretion signal may facilitate subsequent protein purification.

In a further embodiment, it is provided a host cell comprising a recombinant vector according to the invention.

The introduction of the recombinant vector in a host cell can be carried out according to methods that are well known to a person skilled in the art, such as those described in BASIC METHODS IN MOLECULAR BIOLOGY, Davis et al., 2nd ed., McGraw-Hill Professional Publishing, 1995, and MOLECULAR CLONING: A LABORATORY MANUAL, supra, such as transfection by calcium phosphate, transfection by DEAE dextran, transfection, microinjection, transfection by cationic lipids, electroporation, transduction or infection.

The host cell can be, for example, bacterial cells such as *E. coli*, cells of fungi such as yeast cells and cells of *Aspergillus, Streptomyces*, insect cells, Chinese Hamster Ovary cells (CHO), C127 mouse cell line, BHK cell line of Syrian hamster cells, Human Embryonic Kidney 293 (HEK 293) cells.

The host cells can be used, for example, to express a mimetic peptide of the invention. After purification by standard methods, the peptide of the invention can be used in a method described hereinafter.

It is a further embodiment of the invention to provide a method for preparing a peptide according to the invention comprising cultivating a host cell as mentioned above in a culture medium and separating said peptide from the culture medium or from the host cell lysate after host cell lysis. When the internal cross-linking of two non-contiguous amino acid residues of the peptide obtained in the above method is carried out via disulfide bridge formation between two Cystein residues, said cross-linking can take place either during the steps of synthesis and purification of the peptide or in a further independent step.

When the internal cross-linking of two non-contiguous amino acid residues of the peptide according to the invention is carried out via lactam bridge incorporation or via hydrocarbon staple formation, and the peptide is produced via recombinant technology as in the method described above, the preparation of the mimetic peptide according to the invention can require a further step whereby said internal cross-linking of the peptide is carried out as described herewith.

Alternatively, the mimetic peptide according to the invention can be prepared by synthetic chemistry methods, such as solid-phase peptide synthesis. Purification of those peptides may be carried out by means of any technique known in the art for protein/peptide purification. Exemplary techniques include ion-exchange chromatography, hydrophobic interaction chromatography, and immunoaffinity methods.

Internal cross-linking of the peptide according to the invention can be carried out via lactam bridge formation between Glutamic acid and Lysine residues of the peptide using orthogonal protections (O-Fm and Fmoc) when working in Boc-chemistry and forming the lactam bridge on the resin after 20% piperidine base-mediated cleavage of the fluorenylmethyl-ester/carbamate protecting groups for 1 h. When working in Fmoc chemistry, orthogonal protections are for example O-allyl and Aloc and are cleaved on the resin with a 3-fold excess of tetrakis(triphenylphosphine)palladium(O) in CHCl3/AcOH/NMM for 2 h. The peptide lactam cyclization can be carried out with 3 eq. Pyclock and 9 eq. DIEA over 2 days and monitored by Kaiser ninhydrin test (Kaiser et al., 1970, *Anal Biochem* 34:595-598).

In another embodiment, internal cross-linking of the peptide according to the invention is carried out via hydrocarbon staple formation using ring closing metathesis (RCM) of the peptides, in which two α-methyl, α-alkenyl aminoacids have been incorporated during chain extension in solid-phase peptide synthesis. RCM is performed on Fmoc-protected peptides on MBHA-Rink amide resin with Dichloro (o-isopropoxyphenylmethylene) (tricyclohexylphosphine) ruthenium(II) as the catalyst, as described in Kim et al., 2011 (*Nat Protoc* 6: 761-771). Final deprotection (and acetylation) and subsequent cleavage of the mimetic peptide according to the invention from the resin can be performed using the protocol described in the example section.

Compositions and Kits According to the Invention

The invention provides compositions comprising the mimetic peptides according to the invention.

According to one embodiment, the present invention provides compositions comprising the mimetic peptides according to the invention for use as a diagnostic composition or as an immunoassay preparation.

In particular, the present invention provides compositions comprising the mimetic peptides according to the invention for use in the diagnosis and/or prognosis of a cardiovascular disease.

In another embodiment, the present invention provides compositions, in particular pharmaceutical compositions, comprising the mimetic peptides according to the invention for use as a medicament.

The present invention also provides compositions comprising the mimetic peptides according to the invention for use in the treatment of a cardiovascular disease.

According to another aspect of the invention, is provided a kit for detecting anti-ApoA-I antibodies as biomarkers for a cardiovascular disease in a biological fluid sample, the kit comprising at least one mimetic peptide according to the invention, or a variant thereof, or a combination thereof.

In a particular embodiment, the kit according to the invention comprises at least one mimetic peptide which amino acid sequence comprises any one of SEQ ID NO: 2, SEQ ID NO: 3, SEQ ID NO: 4, SEQ ID NO: 5, SEQ ID NO: 21, SEQ ID NO: 23, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 22, SEQ ID NO: 24, and SEQ ID NO: 18, or a variant thereof.

In another particular embodiment, the kit according to the invention comprises at least one mimetic peptide which amino acid sequence comprises any one of SEQ ID NO: 8 SEQ ID NO: 9, or a variant thereof.

In another particular embodiment, the kit according to the invention comprises at least one mimetic peptide which amino acid sequence comprises SEQ ID NO: 25.

In another particular embodiment, the kit according to the invention comprises at least one mimetic peptide which amino acid sequence comprises SEQ ID NO: 5, or a variant thereof.

In particular, the amino acid sequence of said at least one mimetic peptide comprises SEQ ID NO: 5 with the deletion of the last two amino acids E and N at the C-terminal part of SEQ ID NO: 5.

In another particular embodiment, the kit according to the invention comprises at least one mimetic peptide which amino acid sequence comprises SEQ ID NO: 21.

In another particular embodiment, the kit according to the invention comprises at least one mimetic peptide which amino acid sequence comprises SEQ ID NO: 23.

In a still further embodiment, the kit according to the invention comprises at least one mimetic peptide selected among:
 (i) a mimetic peptide having an amino acid sequence comprising SEQ ID NO: 19 and an internal cross-linking that is a lactam bridge of FIG. 2C linking a Glutamic acid (E) at position 19 and a Lysine (K) at position 23;
 (ii) a mimetic peptide having an amino acid sequence comprising SEQ ID NO: 15 and an internal cross-linking that is a hydrocarbon staple of FIG. 2B linking (R)-2-(7'-octenyl)-Alanine at position 16 and (S)-2-(4'-pentenyl)-Alanine at position 23;
 (iii) a mimetic peptide having an amino acid sequence comprising SEQ ID NO: 16 and an internal cross-linking that is a hydrocarbon staple of FIG. 2B linking (S)-2-(4'-pentenyl)-Alanine at position 13 and (S)-2-(4'-pentenyl)-Alanine at position 17;
 (iv) a mimetic peptide having an amino acid sequence comprising SEQ ID NO: 17 and an internal cross-linking that is a hydrocarbon staple of FIG. 2B linking (R)-2-(7'-octenyl)-Alanine at position 9 and (S)-2-(4'-pentenyl)-Alanine at position 16.

In a still further embodiment, the kit according to the invention comprises at least one mimetic peptide selected among:
 (i) a mimetic peptide having an amino acid sequence comprising SEQ ID NO: 15, SEQ ID NO: 16, SEQ ID NO: 17, SEQ ID NO: 19, or SEQ ID NO: 20;
 (ii) a mimetic peptide having an amino acid sequence comprising SEQ ID NO: 13, SEQ ID NO: 22, or SEQ ID NO: 24.

According to a further aspect, the invention relates to a kit for carrying out a method according to the invention.

The kit according to the invention comprises at least one mimetic peptide according to the invention, a variant thereof, or a combination thereof for coupling, or already coupled to a solid matrix as solid phase support as referred herein.

Various solid matrices can be used, including but not limited to glass, polystyrene, polypropylene, nitrocellulose, quartz, ceramic, dextran or other materials. Suitable forms of the solid matrix include beads, microparticles, nanoparticles, tubes, fabrics or plates, films, slides, wells, formed from or coated with these materials. Typically, the solid matrix comprises microtiter wells, such as a 96-well microtiter plate.

The coupling, or fixation, of the mimetic peptides according to the invention to the solid matrix in a kit according to the invention may be carried out by adsorption or chemical coupling to a solid phase support. Any means known in the art for immobilizing a protein or peptide to a solid support can be used. The peptides according to the invention can be either covalently or non-covalently bound to the solid matrix by techniques such as covalent bonding via an amide or ester linkage or adsorption. Peptides can be bound using binding pairs such as biotin and avidin or antibody and antigen. After the peptides are affixed to the solid matrix, the solid matrix can be incubated with a blocking solution (containing a blocking protein such as bovine serum albumin) to reduce non-specific adsorption of antibodies in a test sample to the support surface. According to one aspect, the mimetic peptides according to the invention can be synthesized directly on the solid matrix of the kit of the invention.

According to one embodiment, when the kit comprises at least one mimetic peptide according to the invention, a variant thereof, or a combination thereof, for coupling to a solid matrix as solid phase support, the kit further optionally comprises coupling reagents and/or a solid matrix for performing an immunoassay.

According to another further embodiment, the kit according to the invention further comprises at least one rinsing reagent for washing unbound material before detection in order to avoid background noise detection. Typically rinsing reagents comprise standard buffers known in the art.

According to another further embodiment, the kit according to the invention further comprises at least one control sample optionally together with calibration information for quantification of detected anti-ApoA-I antibodies.

According to another embodiment, the invention provides an immunoassay plate comprising at least one mimetic peptide according to the invention, a variant thereof, or a combination thereof, which are coupled to a solid matrix as solid phase support.

Uses and Methods According to the Invention

According to one aspect, the invention provides a method for detecting endogenous anti-ApoA-I antibodies in a biological fluid sample of a mammalian subject comprising the steps of:
 (a) providing a biological fluid sample from a mammalian subject;
 (b) bringing said biological fluid sample into contact with a solid matrix where at least one mimetic peptide according to the invention is coupled to, wherein the contacting is under conditions sufficient for binding an anti-ApoA-I antibody present in said biological fluid sample to said at least one mimetic peptide through antigen-antibody interactions;
 (c) Removing any unbound antibody from the surface of said solid matrix;

(d) Detecting the presence of an antigen-antibody complex bound to said solid matrix;

wherein the presence of said complex is indicative that the biological fluid sample contains endogenous anti-ApoA-I antibodies.

According to another aspect, the invention provides a method for detecting a cardiovascular disease from a biological fluid sample of a mammalian subject comprising the steps of:
(a) providing a biological fluid sample from a mammalian subject;
(b) bringing said biological fluid sample into contact with a solid matrix where at least one mimetic peptide according to the invention is coupled to, wherein the contacting is under conditions sufficient for binding an anti-ApoA-I antibody present in said biological fluid sample to said at least one mimetic peptide through antigen-antibody interactions;
(c) Removing any unbound antibody from the surface of said solid matrix;
(d) Detecting the presence of an antigen-antibody complex bound to said solid matrix;

wherein the presence of said complex is indicative that the biological fluid sample contains one or more cardiovascular disease associated anti-ApoA-I auto-antibodies.

According to a further embodiment, is provided a method according to the invention, wherein the amino acid sequence of said at least one mimetic peptide comprises the amino acid sequence selected from SEQ ID NO: 2, SEQ ID NO: 3, SEQ ID NO: 4, SEQ ID NO: 5, SEQ ID NO: 21, SEQ ID NO: 23, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 22, SEQ ID NO: 24, and SEQ ID NO: 18, and any variant thereof.

According to a particular embodiment, is provided a method according to the invention, wherein the amino acid sequence of said at least one mimetic peptide comprises the amino acid sequence selected from SEQ ID NO: 2, SEQ ID NO: 3, SEQ ID NO: 4, SEQ ID NO: 5, SEQ ID NO: 21, SEQ ID NO: 23, SEQ ID NO: 6, SEQ ID NO: 7, SEQ ID NO: 8, SEQ ID NO: 9, and any variant thereof.

In a particular embodiment, is provided a method according to the invention, wherein the amino acid sequence of said at least one mimetic peptide comprises the amino acid sequence selected from SEQ ID NO: 8, SEQ ID NO: 9, and any variant thereof.

In a particular embodiment, is provided a method according to the invention, wherein the amino acid sequence of said at least one mimetic peptide comprises the amino acid sequence SEQ ID NO: 25.

In another particular embodiment, is provided a method according to the invention, wherein the amino acid sequence of said at least one mimetic peptide comprises the amino acid sequence SEQ ID NO: 5, and any variant thereof, in particular a variant comprising SEQ ID NO: 5 with the deletion of the last two amino acids E and N at the C-terminal part of SEQ ID NO: 5.

In a particular embodiment, is provided a method according to the invention, wherein the amino acid sequence of said at least one mimetic peptide comprises the amino acid sequence SEQ ID NO: 21.

In a particular embodiment, is provided a method according to the invention, wherein the amino acid sequence of said at least one mimetic peptide comprises the amino acid sequence SEQ ID NO: 23.

According to another particular embodiment, is provided a method according to the invention, wherein the amino acid sequence of said at least one mimetic peptide comprises an amino acid sequence selected from SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 22, SEQ ID NO: 24, and SEQ ID NO: 18, and any variant thereof.

According to a further embodiment, is provided a method according to the invention, wherein the amino acid sequence of said at least one mimetic peptide comprises an amino acid sequence selected from SEQ ID NO: 15, SEQ ID NO: 16, SEQ ID NO: 17, SEQ ID NO: 19, SEQ ID NO: 20, and any variant thereof.

According to a further embodiment, is provided a method according to the invention, wherein the amino acid sequence of said at least one mimetic peptide comprises an amino acid sequence selected from SEQ ID NO: 13, SEQ ID NO: 22 or SEQ ID NO: 24, and any variant thereof.

According to a still further embodiment is provided a method according to the invention, wherein said at least one mimetic peptide comprises any one of:
(i) the amino acid sequence SEQ ID NO: 19 with a lactam bridge of FIG. 2C linking the E at position 19 and K at position 23 on said sequence;
(ii) the amino acid sequence SEQ ID NO: 15 with a hydrocarbon staple of FIG. 2B linking (R)-2-(7'-octenyl)-Alanine at position 16 and (S)-2-(4'-pentenyl)-Alanine at position 23 on said sequence;
(iii) the amino acid sequence SEQ ID NO: 16 and the internal cross-linking under c) is a hydrocarbon staple of FIG. 2B linking (S)-2-(4'-pentenyl)-Alanine at position 13 and (S)-2-(4'-pentenyl)-Alanine at position 17 on said sequence;
(iv) the amino acid sequence SEQ ID NO: 17 and the internal cross-linking under c) is a hydrocarbon staple of FIG. 2B linking (R)-2-(7'-octenyl)-Alanine at position 9 and (S)-2-(4'-pentenyl)-Alanine at position 16 on said sequence.

According to a still further embodiment is provided a method according to the invention, wherein said at least one mimetic peptide comprises any one of:
(i) the amino acid sequence SEQ ID NO: 13, SEQ ID NO: 22 or SEQ ID NO: 24;
(ii) the amino acid sequence SEQ ID NO: 15, SEQ ID NO: 16, SEQ ID NO: 17, SEQ ID NO: 19 or SEQ ID NO: 20.

According to another embodiment is provided a method according to the invention, wherein said at least one mimetic peptide consists of any one of:
(i) the amino acid sequence SEQ ID NO: 19 with a lactam bridge of FIG. 2C linking the E at position 19 and K at position 23 on said sequence;
(ii) the amino acid sequence SEQ ID NO: 15 with a hydrocarbon staple of FIG. 2B linking (R)-2-(7'-octenyl)-Alanine at position 16 and (S)-2-(4'-pentenyl)-Alanine at position 23 on said sequence;
(iii) the amino acid sequence under b) comprises SEQ ID NO: 16 and the internal cross-linking under c) is a hydrocarbon staple of FIG. 2B linking (S)-2-(4'-pentenyl)-Alanine at position 13 and (S)-2-(4'-pentenyl)-Alanine at position 17 on said sequence;

(iv) the amino acid sequence under b) comprises SEQ ID NO: 17 and the internal cross-linking under c) is a hydrocarbon staple of FIG. 2B linking (R)-2-(7'-octenyl)-Alanine at position 9 and (S)-2-(4'-pentenyl)-Alanine at position 16 on said sequence.

According to a still further embodiment is provided a method according to the invention, wherein said at least one mimetic peptide consists of any one of:
(i) the amino acid sequence SEQ ID NO: 13, SEQ ID NO: 22, SEQ ID NO: 24; or a variant thereof;
(ii) the amino acid sequence SEQ ID NO: 15, SEQ ID NO: 16, SEQ ID NO: 17, SEQ ID NO: 19, SEQ ID NO: 20; or a variant thereof.

According to another further embodiment, is provided a method according to the invention, wherein said biological fluid sample is brought into contact with said solid matrix under step (b), where at least one mimetic peptide, or variant thereof, is coupled to said solid matrix.

According to another further embodiment, is provided a method according to the invention, wherein the method further comprises a step of comparing the signal obtained under the detection step (d) with the same signal obtained for at least one control sample, wherein the signal obtained for said at least one control sample is collected previously, simultaneously or posteriorly to the detection step (d) for said biological fluid sample.

Detection of the captured/bound antibodies under step (d) can be carried out by any suitable method known in the art for detecting captured antibodies or proteins on surfaces such as optical detection (e.g. ELISA), mass variation detection (e.g. surface Plasmon resonance, mass spectrometry), electrical detection (e.g. impedance spectroscopy, electrochemical) techniques.

Results of the assay may be qualitative or quantitative. The amount of captured/bound antibodies associated with the solid matrix can be compared with positive and negative controls. The controls are typically run concomitantly with the sample to be tested. A positive control can be a serum or a solution containing antibodies that are immunoreactive with ApoA-I. A negative control can be a serum or solution which does not contain antibodies that are immunoreactive with ApoA-I. For quantization, a calibration curve using known quantities of anti-ApoA-I antibodies can be generated and/or used. Antibodies for use as positive controls may be produced using all, or fragments of, the amino acid sequence of ApoA-I.

The comparison with normal healthy biological fluid samples may be achieved with different methods. According to one embodiment, it may be carried out by including a control reaction with a non-diseased blood sample. According to another embodiment, it may be carried out by employing a value for the concentration of the endogenous anti-ApoA-I antibody for a typical biological fluid sample from a healthy subject. Typically, the comparison of the level of endogenous anti-ApoA-I antibody present in a sample under investigation may be performed with respect to a value determined in each single testing procedure or to a predetermined value. The predetermined value may be determined for the testing procedure in general, or alternatively, the value may be valid only for a certain batch of testing reagents. For example, the reference value may be valid for a defined calibration period only and may be redefined upon calibration of the testing process.

The methods, the kits and uses according to the invention may be suited for screening purposes as well as for diagnostic purposes and may be applied in primary diagnosis as well as in monitoring of disease course during or after treatment.

In particular, the methods, the kits and uses according to the invention may be suited for:
i) diagnosis purposes in patients with acute chest pain to rule out or rule-in a myocardial ischemia and, thus, for the diagnosis of acute coronary syndrome,
ii) prognosis and, possibly, therapeutic purposes in patients with acute chest pain, acute coronary syndrome, rheumatoid arthritis, systemic lupus erythematosus, severe carotid stenosis, end-stage renal disease or periodontitis, since the invention allows identification of the sub-sets of patients having a high cardiovascular risk, and, thus, allows identification of the sub-sets of patients who could benefit from a specific therapy (as described herewith) aiming at reversing the deleterious effects of anti-ApoA-I antibodies.

The aforementioned diagnostic, prognostic and therapeutic purposes may be applied in primary as well as in secondary prevention.

The methods, the kits and uses according to the invention may, in particular, also be suited for determining whether a patient suffering from acute chest pain, acute coronary syndrome, rheumatoid arthritis, systemic lupus erythematosus, severe carotid stenosis, end-stage renal disease or periodontitis, for whom the usual cardiovascular risk factors (including tobacco use, alcohol use, high blood pressure, high cholesterol, obesity, physical inactivity, unhealthy diets) are not observed, could nevertheless benefit from a therapy for preventing or treating a cardiovascular disease such as a method comprising administering at least one mimetic peptide according to the invention.

The prognostic and/or diagnostic assays described herein can be used to determine whether a subject could benefit from the administration of an agent (e.g., a drug) for preventing and/or treating a cardiovascular disease. For example, such assays can be used to determine whether the administration of a therapeutic agent suitable for treating a cardiovascular disease such as ApoA-I, a mimetic peptide according to the invention, intravenous immunoglobulins (IVIG) or eplerenone, could be beneficial to a subject.

Intravenous immunoglobulin (IVIG) is a blood product administered intravenously. It contains the pooled, polyvalent, IgG immunoglobulin extracted from the plasma of over one thousand blood donors. Typically, the dosage of IVIG is dependent on indication. For primary immune dysfunction 100 to 400 mg/kg of body weight every 3 to 4 weeks is implemented. For neurological and autoimmune diseases 2 grams per kilogram of body weight is implemented for three to six months over a five day course once a month. Then, maintenance therapy of 100 to 400 mg/kg of body weight every 3 to 4 weeks follows.

Eplerenone (systematic IUPAC name: pregn-4-ene-7,21-dicarboxylic acid, 9,11-epoxy-17-hydroxy-3-oxo, γ-lactone, methyl ester (7α, 11α, 17α) is an aldosterone antagonist used as an adjunct in the management of chronic heart failure. It is specifically marketed for reducing cardiovascular risk in patients following myocardial infarction.

Therefore, another aspect of the invention is a method of determining whether a subject, in particular a subject suffering from acute chest pain, acute coronary syndrome, rheumatoid arthritis, systemic lupus erythematosus, severe carotid stenosis, end-stage renal disease or periodontitis could benefit from the administration of a therapeutic agent for preventing and/or treating a cardiovascular disease.

Another aspect of the invention is a method of monitoring the course of a cardiovascular disease in a subject during or after treatment. For this purpose, the detection of anti-ApoA-I antibodies in a subject's biological sample can be determined on biological samples from a subject before, during, or after undergoing a treatment. A decrease in the amount of anti-ApoA-I antibodies detected after the treatment indicates that the subject can be further treated by the same treatment. The absence of anti-ApoA-I antibodies after the treatment indicates that the treatment can be interrupted or continued at a lower frequency and/or lower dosage.

Information obtained from practice of the above assays is useful in prognostication, identifying progression of, and clinical management of diseases and other deleterious conditions affecting an individual's health status. The information more specifically assists the clinician in designing therapy or other treatment regimes to treat cardiovascular disease, in particular in sub-populations of patients suffering from acute chest pain, acute coronary syndrome, rheumatoid arthritis, systemic lupus erythematosus, severe carotid stenosis, end-stage renal disease or periodontitis.

In another aspect of the invention, is provided a method for preventing and/or treating a cardiovascular disease or disorder in a subject in need thereof comprising administering a mimetic peptide according to the invention, or a pharmaceutical formulation thereof, to said subject.

In another aspect of the invention, is provided a method for preventing and/or treating a cardiovascular disease or disorder in a subject in need thereof comprising administering a 3-dimensional structural analogue of a mimetic peptide according to the invention.

In the context of the invention, a 3-dimensional structural analogue of a mimetic peptide can be any chemical molecule, in particular any small molecule which has been either found in a chemical library or designed to exhibit a similar 3-dimensional structure as that of said mimetic peptide.

In a particular embodiment, the invention provides a method for preventing and/or treating a cardiovascular disease in a subject, comprising administering at least one of: (i) a mimetic peptide according to the invention, or a pharmaceutical formulation thereof, (ii) a 3-dimensional structural analogue of a mimetic peptide according to the invention, (iii) a pharmaceutical composition comprising ApoA-I, and (iv) an agent suitable for preventing and/or treating a cardiovascular disease such as intravenous immunoglobulins or eplerenone, to a subject who has been diagnosed by the method according to the invention as having endogenous anti-ApoA-I antibodies.

In a particular embodiment, the method above is applied to a subject suffering from acute chest pain, acute coronary syndrome, rheumatoid arthritis, systemic lupus erythematosus, severe carotid stenosis, end-stage renal disease or periodontitis.

In a further embodiment, the method for preventing and/or treating a cardiovascular disease according to the invention is carried out in a subject suffering from acute chest pain, acute coronary syndrome, rheumatoid arthritis, systemic lupus erythematosus, severe carotid stenosis, end-stage renal disease or periodontitis, who has been diagnosed, following a method of detection according to the invention, as having endogenous anti-ApoA-I antibodies.

In a still further embodiment, the subject does not present the usually observed cardiovascular risk factors such as tobacco use, alcohol use, high blood pressure, high cholesterol, obesity, physical inactivity, unhealthy diets.

In another aspect, the invention provides the use of a mimetic peptide according to the invention for the preparation of a medicament, in particular for the preparation of a medicament for preventing and/or treating a cardiovascular disease. In a further aspect, the invention provides the use of a mimetic peptide according to the invention for the preparation of a diagnostic composition or an immunoassay preparation, in particular for diagnosing a cardiovascular disease.

Mode of Administration

Compounds, compositions, in particular pharmaceutical compositions, and formulations thereof according to this invention may be administered in any manner including orally, parenterally, intravenously, subcutaneously, rectally, or combinations thereof. Parenteral administration includes, but is not limited to, intravenous, intra-arterial, intra-peritoneal, subcutaneous, intradermal and intramuscular. The compositions of this invention may also be administered in the form of an implant, which allows slow release of the compositions as well as a slow controlled i.v. infusion.

In particular, the compounds, compositions, in particular pharmaceutical compositions, and formulations thereof according to the invention are administered subcutaneously.

In one embodiment of the invention, the administration of compositions of the invention requires multiple successive injections.

In a particular embodiment of the invention, the pharmaceutical composition may be administered repeatedly or continuously. The pharmaceutical composition can be administered repeatedly or continuously for a period of at least 1, 2, 3, or 4 weeks; 2, 3, 4, 5, 6, 8, 10, or 12 months; or 2, 3, 4, or 5 years.

Combination

According to the invention, a mimetic peptide according to the invention, or the pharmaceutical composition thereof, can be administered alone or in combination with a co-agent useful in the prevention and/or treatment of cardiovascular disease.

In another embodiment, the pharmaceutical composition may be administered with another therapeutic agent that is useful for preventing or treating a cardiovascular disease, such as aspirin, beta-blockers, angiotensin converter enzyme inhibitor, and statins.

The invention encompasses the administration of a mimetic peptide according to the invention wherein the mimetic peptide is administered to an individual prior to, simultaneously or sequentially with other therapeutic regimens or co-agents useful in the prevention and/or treatment of cardiovascular disease (e.g. multiple drug regimens), in a therapeutically effective amount. The mimetic peptides according to the invention that are administered simultaneously with said co-agents can be administered in the same or different compositions and in the same or different routes of administration.

Patients

In one embodiment, patients according to the invention are patients suffering from a cardiovascular disease or suspected of suffering from such a disease.

In a particular embodiment, patients according to the invention have been admitted to the emergency department with acute chest pain.

In another embodiment, patients according to the invention are patients who have been admitted to the emergency department with acute chest pain and who have been diagnosed as suffering from a cardiovascular disease following the prognostic and/or diagnostic assays according to the invention.

In a still other embodiment, patients according to the invention are patients suffering from acute chest pain, acute coronary syndrome, rheumatoid arthritis, systemic lupus erythematosus, severe carotid stenosis, end-stage renal disease or periodontitis.

In a still further embodiment, the patients according to the invention do not present the usually observed cardiovascular risk factors such as tobacco use, alcohol use, high blood pressure, high cholesterol, obesity, physical inactivity, unhealthy diets.

In a further embodiment, patients according to the invention are patients suffering from acute chest pain, acute coronary syndrome, rheumatoid arthritis, systemic lupus erythematosus, severe carotid stenosis, end-stage renal disease or periodontitis, who have been diagnosed as suffering from a cardiovascular disease following the prognostic and/or diagnostic assays according to the invention.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention having been described, the following examples are presented by way of illustration, and not limitation.

EXAMPLES

The following abbreviations refer respectively to the definitions below:

aa (amino acid); AUC (area under curve), h (hour), µl (microliter), µM (micromolar), mM (millimolar), mg (milligram), min (minute), nm (nanometer), BSA (bovine serum albumin), CI (confidence interval), $CH_2Cl_2$ (dichloromethane), DIPEA (diisopropylethylamine), DMF (Dimethylformamide), EDTA (ethylene diamine tetraacetic acid), HCTU (2-(6-Chloro-1-H-benzotriazole-1-yl)-1,1,3,3-tetramethyl-aminiumhexafluoro-phosphate), HoBt (N-hydroxy-benzotriazole), OR (odds ratio), PBS (phosphate-buffered saline), PyBOP (Benzotriazol-1-yl-oxy-tris-pyrrolidino-phosphonium hexafluoro-phosphate), PyClock (6-Chloro-benzotriazole1-yl-oxy-tris-pyrrolidino-phosphonium hexafluoro-phosphate), TFA (Trifluoroacetic acid), TIS (triisopropylsilane).

Materials and Methods

Peptide Synthesis

Linear peptides, C-terminal-thioester derivatives for native chemical ligation (Dawson et al, 1994, *Science* 266: 776-779) and certain lactam-bridged analogues (F3L1) were synthesized by using Boc-based Merrifield solid phase peptide synthesis on a ABI 433A peptide synthesizer adapted to Boc chemistry (Wilken and Kent, 1998, *Curr Opin Biotechnol* 9:412-426). Cleavage from the resin was performed with hydrogen fluoride. For lactam bridge incorporation, orthogonal protections (O-Fm and Fmoc) were respectively used for Glu and Lys, and the lactam bridge was formed on the resin after 20% piperidine base-mediated cleavage of the fluorenylmethyl-ester/carbamate protecting groups for 1 h. The peptide lactam cyclization was carried out with 3 eq. Pyclock and 9 eq. DIEA over 2 days and was monitored by Kaiser ninhydrin test (Kaiser et al, 1970, *Anal Biochem* 34:595-598).

The length of peptides EF ($Ala^{190}$-$Thr^{242}$ ApoA-I i.e. 53 residues) necessitated synthesis via two fragments ($Ala^{190}$-$Arg^{215}$ and $Gln^{216}$-$Thr^{242}$), which were assembled by native chemical ligation (Dawson et al, 1994, *Science* 266:776-779). Because this approach requires N-terminal Cys on the C-terminal fragment, it was necessary to replace $Gln^{216}$ in the ApoA-I sequence by a Cys residue. This residue was alkylated with iodoacetamide after the ligation step to yield a Gln analog (side chain $CH_2$—S—$CH_2$—$CONH_2$ rather than $CH_2$—$CH_2$—$CONH_2$). Furthermore, since termini of the peptide were cyclized through a disulfide bridge, Cys (Acm) residues were added to the N-terminus of $Ala^{190}$-$Arg^{215}$ and C-terminus of $Gln^{216}$-$Thr^{242}$. These were deprotected with HgOAc after alkylation of the ligation product and oxidized with $H_2O_2$. The best results for cyclization were obtained when using 20 eq. $H_2O_2$ over 30 min at pH 7.0, followed immediately by purification by RP-HPLC.

Fmoc-based solid phase synthesis was also used to generate some of the linear peptides with a lactam bridge. In this case a pair of orthogonal protecting groups (allyl/alloc) was used for glutamic acid and lysine residues. These protecting groups were removed with 3 eq. $Pd(PPh_3)_4$ in $CHCl_3$—AcOH—N-methylmorpholine (37:2:1) over 2 h, according to the procedure of Kates et al. (30), prior to the peptide cyclization.

All hydrocarbon-stapled peptides were synthesized using standard Fmoc chemistry on MBHA-Rink amide resin (0.56 mmol/g loading) at 100 µmol scale with a Prelude synthesizer (Protein Technologies Inc., Tucson, U.S.A). One cycle of peptide elongation consisted of the following steps: (i) loaded resin was first washed with DMF (3×30 sec) and the terminal Fmoc protecting group was removed with 20% piperidine/DMF (2×10 min); (ii) deprotected resin was then washed with DMF (6×30 s) and treated for 30 min with a solution containing 5 eq. of the appropriate Fmoc-amino acid, 5 eq. HCTU, and 10 eq. DIPEA; (iii) resin was then washed three times with NMP (3×30 s), with unreacted amino groups acetylated upon treatment with 10% v/v acetic anhydride in DMF (1×10 min), and the capped resin washed with DMF (6×30 s). These steps were repeated until the peptide sequence was complete.

Coupling of α-methyl, α-alkenyl glycine was performed manually as described previously (Kim et al, 2011, *Nat Protoc* 6:761-771) with slight modifications. The deprotected resin was treated over 2 h with a solution containing 2 eq. of the amino acid, 2 eq. Pyclock and 4 eq. DIPEA. This step was repeated if double coupling was necessary. The following amino acid in the sequence was also incorporated manually in a double coupling step over 1 h with a solution containing 5 eq. amino acid, 5 eq. PyClock and 15 eq. DIEA.

Once the final Fmoc-protecting group was removed, the resin was treated with 10% (v/v) acetic anhydride and 1% (v/v) DIPEA in DMF (1×10 min) to yield an acetyl-capped N-terminus. The resin was subsequently washed with DMF (5×30 s) and $CH_2Cl_2$ (5×30 s), dried for 20 min under vacuum, and then treated for 90 min with a cleavage solution containing 2.5% (v/v) water, 2.5% (v/v) triisopropylsilane and 5% phenol in TFA.

Ring-Closing Metathesis

Ring closing metathesis (RCM) of all peptides containing olefinic amino acid derivatives was performed on Fmoc-protected peptides on MBHA-Rink amide resin with Dichloro (o-isopropoxyphenylmethylene) (tricyclohexylphosphine) ruthenium (II) as the catalyst, as described (Kim et al, 2011, *Nat Protoc* 6:761-771). The resin was washed successively with DCM and DCE and treated with a 6 mM solution of Grubbs' first-generation catalyst in DCE (4.9 mg/ml, 0.2 eq. with regard to the resin substitution) over 2 h, accompanied by a low but continuous $N_2$ bubbling through the solution. RCM was repeated twice. Progress of the metathesis reaction was monitored by HPLC and ESI-MS upon cleaving a small sample off resin. Final deprotection (and acetylation) and subsequent cleavage of the peptide from the resin was performed using the protocol described above.

Peptide Purification and Analysis

Mass spectra were acquired on a Micromass-Platform LCZ mass spectrometer. Analytical reverse phase high pressure liquid chromatography (HPLC) was performed on a Waters 2795 HPLC module coupled with 214 nm UV detection, using a Phenomenex-Aeris widepore, 3.6 μm XB C8, 4.6 mm×150 mm column. Preparative HPLC was performed on a Delta 600 module coupled with a 2487 UV detector using a Vydac C8 column (250×22 mm i.d., 10 μm particle size). The eluents were 0.1% aqueous TFA and 0.1% TFA in acetonitrile:water (9:1, v:v).

The yield of each synthesis was assessed first by HPLC and ESI-MS analysis of the crude reaction mixture. Peptides were then purified to homogeneity by reverse-phase HPLC. The identities and purities of purified peptides were assessed by analytical HPLC and mass spectrometry.

Screening Sera from Acute Chest Pain Patients with or without Anti-ApoA-I Auto-Antibodies Serum samples used as the same as those described in a previously published study involving 138 patients admitted to the emergency department (ED) with acute chest pain (Keller et al, 2012, *J Intern Med* 271:451-462). The aim of this study was to determine the diagnostic accuracy of IgG immunoreactivity against ApoA-I in the very first plasma sample collected at the ED for (i) non-ST segment elevation myocardial infarction (NSTEMI) and (ii) subsequent troponin I elevation. Details of sample collection and processing, endpoint definitions and inclusion/exclusion criteria are described in Keller et al (2012, *J Intern Med* 271:451-462). Due to material shortage for six of the patients, the analyses on the peptides were performed on samples from the remaining 132 patients.

Patient Serum Enzyme-Linked Immunosorbant Assay (ELISA)

Immunoreactivity with patient sera was measured by ELISA as previously described (Vuilleumier et al, 2010, *Eur Heart J* 31:815-823). Briefly, Maxisorp plates (Nunc™, Roskilde, Denmark) were coated with either purified, human-derived delipidated ApoA-I (20 μg/mL; 50 μL well) or synthetic ApoA-I-derived peptides (20 μg/mL; 50 μL well) for 1 h at 37° C. After washing, wells were blocked for 1 h with PBS with 2% BSA at 37° C. Then, duplicate serum samples diluted 1/50 were added to the wells and incubated for 1 h. Serum samples were also added to a non-coated well to assess the individual nonspecific binding. After washing six times, (50 μL well) alkaline phosphatase-conjugated anti-human IgG (Sigma-Aldrich, St Louis, Mo., USA) diluted 1/1000 in PBS/BSA solution was added to wells and incubated for 1 h at 37° C. After washing again six times, wells were developed by adding alkaline phosphatase substrate disodium p-nitrophenylphosphate (Sigma-Aldrich), dissolved in diethanolamine buffer (pH 9.8). After 20 min incubation at 37° C., ELISA signals (absorbance $OD_{405\ nm}$) were determined using a plate reader (Molecular Devices Versa Max™; Molecular Device, Sunnyvale, Calif., USA). The corresponding nonspecific binding was subtracted from the mean absorbance for each sample.

Competition ELISA experiments using selected synthetic peptides were also carried out. Synthetic peptides (dissolved in PBS with 2% bovine serum albumin (BSA) at different concentrations were co-incubated with patient sera containing high levels of anti-ApoA-I IgG for 2 h at room temperature, before being added to the wells coated with purified, human-derived delipidated ApoA-I as described above, prior to development of the assay as described above.

Statistical Analyses

Analyses were performed using Statistica™ software (StatSoft, Tulsa, Okla., USA). Fisher's bilateral exact test and Mann Whitney U-test were used where appropriate. Associations between immunoreactivity to different peptides, and study endpoints are presented as the odds ratio (OR) and corresponding 95% confidence interval (95% CI). Multivariable analyses with logistic regression were used to assess associations between variables. In this model, endpoints were set as dependent variables, and NSTEMI-TIMI score (Antman et al, 2000, *JAMA* 284:835-842) (allowing for adjustment for major CV determinants of patient outcome at 14 days within a single continuous variable) was set as the unique confounder because of the limited sample size. ROC analyses were performed using Analyse-It™ software for Excel (Microsoft, Redmond, Wash., USA). Areas under the curve (AUC) comparisons were performed according to the nonparametric approach proposed by DeLong et al. (1988, Biometrics 44:837-845).

Cell-Based Experiments: Anti-ApoA-I IgG-Related Pro-Inflammatory Response

Human monocyte-derived macrophages (HMDMs) were obtained by treating human monocytes with interferon (IFN)-γ for 24 hours as previously described (Pagano et al, 2012, *J Intern Med*). HMDMs were then stimulated in 96-well trays for 24 h with increasing concentrations (5-40 μg/mL) of either polyclonal anti-human ApoA-I (Academy Bio-Medical Company, Houston, Tex., USA) or control antibody (Meridian Life Science, Saco, Me., USA), with IgG from pool+ or pool− (500 μg/mL). In this model, LPS-free anti-ApoA-I IgG has been show to promote the production of TNF-α and IL-6 in a dose dependent manner, with an optimal stimulation at 40 μg/ml (Pagano et al, 2012, *J Intern Med*).

For competition inhibition experiments, synthetic peptides were co-incubated with 40 μg/ml polyclonal anti-ApoA-I IgG for 2 h at room temperature prior to addition to HMDMs in 96-well plates, and followed by the assessment of IL-6 and TNF-α levels in cell supernatants using Luminex MAP™ Technology. Experiments were performed with blood from three different donors.

Cell-Based Experiments: Anti-ApoA-I IgG-Related Chronotropic Response

Neonatal rat ventricular cardiomyocytes (NRVC) were isolated from ventricles of 1-2 day-old Wistar rats by digestion with low trypsin-EDTA and type 2 collagenase. Animals were killed by decapitation without any anesthesia, analgesia, or administration of neuromuscular blocking agents, in conformity with the Guide for the Care and Use of Laboratory Animals published by the NIH (publication 85-23) and with the authorization (1012/3134/0-R) of the local county veterinary office. Freshly isolated cells were seeded in plastic flasks to allow selective adhesion of cardiac fibroblasts. Thereafter cardiomyocytes were decanted from the flasks and distributed into laminin-coated 90 mm petri dishes.

After 1-2 days' culture, cells were incubated at time intervals with the appropriate concentration of monoclonal anti-ApoA-I IgG (Abcam, Nottingham, UK) or vehicle in serum-free DMEM. The beating frequency of spontaneously contracting small cell monolayers was determined immediately at the end of the pre-incubation period (t=0) and at different times after the addition of various substances. Frequency determinations were performed by a technician (unaware of the experimental conditions) using a light microscope to count the number of contractions per time unit in three different locations of the dish. The regularity of the cell contractions has been previously assessed by monitoring cytosolic-free calcium fluctuations with fluorescent calcium probes (Maturana et al, 2009, *Endocrinology* 150: 3726-3734). Because it was previously demonstrated that the maximal chronotropic effect of anti-ApoA-I IgG is reached at 10 µg/ml (Vuilleumier et al, 2010, *Eur Heart J* 31:815-823), this concentration of antibody was maintained in all experiments. Competition inhibition experiments with synthetic peptides were performed using the same experimental conditions. Synthetic peptides were co-incubated with 10 µg/ml monoclonal anti-ApoA-I (Abcam, Nottingham, UK) for 2 h at room temperature, before being added to NRVC in dishes, with beating frequency determined as described above.

CD Spectroscopy to Determine Helical Content

Circular dichroism (CD) spectra from 185 to 240 nm were collected on a Jasco J-815 spectropolarimeter at 20° C. A typical sample was prepared by dissolving lyophilized peptide in 25% trifluoroethanol in water to obtain a concentration of 2 mM, then diluting this solution 20-fold in water and loading in a quartz cuvette (0.2 cm path length). Baseline CD spectra for 1.25% TFE in water was subtracted from the experimental spectra. Data were normalized by calculating the mean residue ellipticity at wavelength 222 nm, $(\theta)_{mrw, \lambda}$.

Example 1: Examples of Mimetic Peptides According to the Invention

The mimetic peptides described in Table 3 below were synthesized as described in the above Materials and Methods section and further characterized by mass-spectrometry.

TABLE 3

Examples of mimetic peptides according to the invention and their amino acid sequence.

| Peptide | Label |
|---|---|
| Ac-VKDL<u>Xaa</u>TVYVDV<u>Xaa</u>KDSGRDYVSQFEGSAL-NH$_2$ (SEQ ID NO: 10 wherein Xaa at position 5 is substituted into a modified alanine of formula (I): —NH—C(CH$_3$)(R)—C(O)— wherein R is a hydrocarbon staple —(CH$_2$)$_6$—CH═CH—(CH$_2$)$_3$— linked to a subsequent Xaa at position 12, and wherein Xaa at position 12 is a modified alanine of formula (I): —NH—C(CH$_3$)(R')—C(O)— wherein R' is a single bond linked to the hydrocarbon staple from Xaa at position 5 as defined above) with the free amino group at the N-terminal end acetylated and free carboxy group at the C-terminal end amidated | A1S2 |
| Ac-DSVTST<u>Xaa</u>SKLREQ<u>Xaa</u>GPVTQEFWDNLEKETEGL-NH$_2$ (SEQ ID NO: 11 wherein Xaa at position 7 is a modified alanine of formula (I): —NH—C(CH$_3$)(R)—C(O)— wherein R is a hydrocarbon staple —(CH$_2$)$_6$—CH═CH—(CH$_2$)$_3$— linked to a subsequent Xaa at position 14, and wherein Xaa at position 14 is a modified alanine of formula (I): —NH—C(CH$_3$)(R')—C(O)— wherein R' is a single bond linked to the hydrocarbon staple from Xaa at position 7 as defined above) with the free amino group at the N-terminal end acetylated and free carboxy group at the C-terminal end amidated) | B1S2 |
| Ac-YLDDFQKKWQEE<u>Xaa</u>ELYRQK<u>Xaa</u>EPLRAELQEGARQKLHEL-NH$_2$ (SEQ ID NO: 12 wherein Xaa at position 13 is a modified alanine of formula (I): —NH—C(CH$_3$)(R)—C(O)— wherein R is a hydrocarbon staple —(CH$_2$)$_6$—CH═CH—(CH$_2$)$_3$— linked to a subsequent Xaa at position 20, and wherein Xaa at position 20 is a modified alanine of formula (I): —NH—C(CH$_3$)(R')—C(O)— wherein R' is a single bond linked to the hydrocarbon staple from Xaa at position 13 as defined above) with the free amino group at the N-terminal end acetylated and free carboxy group at the C-terminal end amidated | C1S2 |
| Ac-EEMRDRARAH<u>Xaa</u>DALRTH<u>Xaa</u>APYSDELRQRLAARLEALKEN-NH$_2$ (SEQ ID NO: 13 wherein Xaa at position 11 is a modified alanine of formula (I): —NH—C(CH3)(R)—C(O)— wherein R is a hydrocarbon staple —(CH$_2$)$_6$—CH═CH—(CH$_2$)$_3$— linked to a subsequent Xaa at position 18, and wherein Xaa at position 18 is a modified alanine of formula (I): —NH—C(CH$_3$)(R')—C(O)— wherein R' is a single bond linked to the hydrocarbon staple from Xaa at position 11 as defined above) with the free amino group at the N-terminal end acetylated and free carboxy group at the C-terminal end amidated | D1S2A |
| Ac-ATEH<u>Xaa</u>STLSEK<u>Xaa</u>KPALED-NH$_2$ (SEQ ID NO: 14 wherein Xaa at position 5 is a modified alanine of formula (I): —NH—C(CH$_3$)(R)—C(O)— wherein R is a hydrocarbon staple —(CH$_2$)$_6$—CH═CH—(CH$_2$)$_3$— linked to a subsequent Xaa at position 12, and wherein Xaa at position 12 is a modified alanine of formula (I): —NH—C(CH$_3$)(R')—C(O)— wherein R' is a single bond linked to the hydrocarbon staple from Xaa at position 5 as defined above) with the free amino group at the N-terminal end acetylated and free carboxy group at the C-terminal end amidated | E1S2 |

TABLE 3-continued

Examples of mimetic peptides according to the invention and their amino acid sequence.

| | |
|---|---|
| Ac-GLLPVLESFKVSFLSALE<u>Xaa</u>YTK<u>Xaa</u>LNT-NH$_2$ (SEQ ID NO: 19) wherein Xaa at position 19 is a modified amino acid of formula (I): —NH—C(H)(R)—C(O)— wherein R is a lactam bridge —(CH$_2$)$_2$—CO—NH—(CH$_2$)$_4$— linked to a subsequent Xaa at position 23, and wherein Xaa at position 23 is a modified amino acid of formula (I): —NH—C(H)(R')—C(O)— wherein R' is a single bond linked to the lactam bridge from Xaa at position 19 as defined above) with the free amino group at the N-terminal end acetylated and free carboxy group at the C-terminal end amidated | F3L1 |
| Ac-GLLPVLESFKVSFLS<u>Xaa</u>LEEYTK<u>Xaa</u>LNT-NH$_2$ (SEQ ID NO: 15) wherein Xaa at position 16 is a modified alanine of formula (I): —NH—C(CH$_3$)(R)—C(O)— wherein R is a hydrocarbon staple —(CH$_2$)$_6$—CH═CH—(CH$_2$)$_3$— linked to a subsequent Xaa at position 23, and wherein Xaa at position 23 is a modified alanine of formula (I): —NH—C(CH$_3$)(R')—C(O)— wherein R' is a single bond linked to the hydrocarbon staple from Xaa at position 16 as defined above) with the free amino group at the N-terminal end acetylated and free carboxy group at the C-terminal end amidated | F3S2A |
| Ac-GLLPVLESFKVS<u>Xaa</u>LSA<u>Xaa</u>EEYTKKLNT-NH$_2$ (SEQ ID NO: 16 wherein Xaa at position 13 is a modified alanine of formula (I): —NH—C(CH$_3$)(R)—C(O)— wherein R is a hydrocarbon staple —(CH$_2$)$_3$—CH═CH—(CH$_2$)$_3$— linked to a subsequent Xaa at position 17, and wherein Xaa at position 17 is a modified alanine of formula (I): —NH—C(CH$_3$)(R')—C(O)— wherein R' is a single bond linked to the hydrocarbon staple from Xaa at position 13n as defined above) with the free amino group at the N-terminal end acetylated and free carboxy group at the C-terminal end amidated | F3S1B |
| Ac-VLESFKVS<u>Xaa</u>LSALEE<u>Xaa</u>TKKLNT-NH$_2$ (SEQ ID NO: 17) wherein Xaa at position 9 is a modified alanine of formula (I): —NH—C(CH$_3$)(R)—C(O)— wherein R is a hydrocarbon staple —(CH$_2$)$_6$—CH═CH—(CH$_2$)$_3$— linked to a subsequent Xaa at position 16, and wherein Xaa at position 16 is a modified alanine of formula (I): —NH—C(CH$_3$)(R')—C(O)— wherein R' is a single bond linked to the hydrocarbon staple from Xaa at position 9 as defined above) with the free amino group at the N-terminal end acetylated and free carboxy group at the C-terminal end amidated | F4S2B |
| Ac-VLESFKVSFLSALE<u>Xaa</u>YTK<u>Xaa</u>LNT-NH$_2$ (SEQ ID NO: 20) wherein Xaa at position 15 is a modified amino acid of formula (I): —NH—C(H)(R)—C(O)— wherein R is a lactam bridge —(CH$_2$)$_2$—CO—NH—(CH$_2$)$_4$— linked to a subsequent Xaa at position 19, and wherein Xaa at position 19 is a modified amino acid of formula (I): —NH—C(H)(R')—C(O)— wherein R' is a single bond linked to the lactam bridge from Xaa at position 15 as defined above) with the free amino group at the N-terminal end acetylated and free carboxy group at the C-terminal end amidated | F4L1 |
| *CAEYHAKATEHLSTLSEKAKPALEDLR<u>Xaa</u>GLLPVLESFKVSFLSALE<u>Xaa</u>YTK<u>Xaa</u>LNTC-NH$_2$ (SEQ ID NO: 18) wherein Xaa at position 28 is a Gln analogue having CH$_2$—S—CH$_2$—CONH$_2$ as side chain, wherein Xaa at position 47 is a modified amino acid of formula (I): —NH—C(H)(R)—C(O)— wherein R is a lactam bridge —(CH$_2$)$_2$—CO—NH—(CH$_2$)$_4$— linked to a subsequent Xaa at position 51, and wherein Xaa at position 51 is a modified amino acid of formula (I): —NH—C(H)(R')—C(O)— wherein R' is a single bond linked to the lactam bridge from Xaa at position 47 as defined above) with the Cys residues oxidized to form a disulfide bridge and the free carboxy group at the C terminal end amidated | EFL1 |

In addition to a lactam bridge as disclosed above, the mimetic peptide EFL1 also contained a disulfide bridge for bringing the two regions derived from Apo-AI helices E and F in a close proximity. Peptide cyclization through a disulfide bridge in case of EFL1 was confirmed by a loss of 2 Da as well as by a peak shift on analytical HPLC. This was also the case for lactam bridge formation and ring closing metathesis, with mass losses of 18 Da (elimination of $H_2O$) and 28 Da (ethylene removal), respectively. During ring-closing metathesis of fragment C1S2, two isomers with the expected mass but with different RP-HPLC mobilities were obtained. These were purified separately and tested independently.

Peptide F3, derived from helix F of ApoA-I, was chosen as control in the experimental section. Peptide F3 has an amino acid sequence of SEQ ID NO: 9, with the free amino group at the N-terminal end acetylated and free carboxy group at the C-terminal end amidated, and does not contain any internal cross-linking.

SEQ ID NO: 9: GLLPVLESFKVSFLSALEEYTKKLNT

Example 2: Alpha-Helical Content of the Mimetic Peptides of the Invention

Alpha-helical content of mimetic peptides F3L1, F3S2A, F3S1B, F4S2B and F4L1 (see Table 3) was assessed by CD spectroscopy as described in the above Material and Methods section. Results presented in FIG. 3 show that stapled F3S2A and bridged F3L1 and F4L1 as well as stapled F3S1B and F4S2B exhibit an increased alpha-helical content (characteristic troughs at 208 and 222 nm) in comparison to the non-stapled control peptide F3.

Example 3: Antigenicity and Diagnostic Potential of the Mimetic Peptides of the Invention Mimetic peptides F3L1, F3S2A, F3S1B, and F4S2B (see Table 3) were assessed for reactivity with serum from the cohort of 132 acute chest pain patients using the Patient serum ELISA assay, with results subjected to statistical analyses. The results, shown in Table 4, clearly indicate the increase in diagnostic precision afforded by the hydrocarbon stapled F3S2A, F3S1B, F4S2B, and lactam bridged F3L1 mimetic peptides with respect to the non-stapled control peptide (F3). Indeed, the statistical parameters for those mimetic peptides, in particular for F3L1, compare favorably with those of Copeptin, and approach those obtainable with intact Apo-A-1. Copeptin is an internal control validating the fact that the cohort of patients used is indeed representative of acute chest pain patients (Reichelin, et al, 2009, *J Am Coll Cardiol.* 54(1):60-8). Copeptin, also known as c-ter provasopressin, is the precursor of vasopressin which is a key hormone in water homeostasis, whose circulating levels have been shown to yield a strong prognostic value in acute coronary syndromes (Lippi et al, 2012, *Clin Chem Lab Med.* 50(2):243-5).

TABLE 4

Diagnostic properties of mimetic peptides for NSTEMI diagnosis and subsequent cTnI elevation on 132 ACP patients derived from patient serum ELISA assay. Results for intact ApoA-I and copeptin are included for comparison and were obtained from experiments carried out at the same period. Statistically significant results ($p < 0.05$) are indicated in bold. *Adjusted for NSTEMI-TIMI score; For risk analyses: Copeptin cut-off: <9 pmol/L (*Reichlin et al, 2009, JACC*), **cut-off adapted and place at the $80^{th}$ percentile of the study population distribution.

| Capture reagent | NSTEMI prediction | | | Subsequent cTnI prediction | | |
|---|---|---|---|---|---|---|
| | AUC (95% CI) | Univariate OR | Adjusted* OR | AUC (95% CI) | Univariate OR | Adjusted* OR |
| F3 | 0.55 (0.41-0.68) p = 0.25 | 1.92 p = 0.41 | 2.53 p = 0.33 | 0.58 (0.40-0.76) p = 0.20 | 1.47 p = 0.53 | 1.57 p = 0.50 |
| F3L1 | 0.64 (0.52-0.76) p = 0.01 | 6.87 p = 0.001 | 7.02 p = 0.005 | 0.68 (0.51-0.85) p = 0.01 | 4.32 p = 0.05 | 3.68 p = 0.10 |
| F3S2A | 0.64 (0.51-0.77) p = 0.01 | **3.09 p = 0.01 | **3.6 p = 0.02 | 0.69 (0.51-0.87) p = 0.01 | 2.72 p = 0.14 | 2.69 p = 0.17 |
| F3S1B | 0.56 (0.42-0.69) p = 0.20 | 3.03 p = 0.03 | 4.12 p = 0.02 | 0.50 (0.29-0.72), p = 0.48 | 1.42 p = 0.66 | 1.43 p = 0.67 |
| F4S2B | 0.62 (0.51-0.74) p = 0.01 | **3.78* p = 0.004 | 3.46* p = 0.01 | 0.66 (0.52-0.80) p = 0.01** | 2.21 p = 0.23 | 1.70 p = 0.45 |
| ApoA-I | 0.75 (0.64-0.85) p < 0.0001 | 9.8 p < 0.0001 | 6.43 p = 0.005 | 0.80 (0.68-0.91) p < 0.0001 | 6.4 p = 0.009 | 3.82 p = 0.07 |
| Copeptin | 0.63 (0.51-0.75) p = 0.01 | 2.12 p = 0.11 | 3.40 p = 0.10 | 0.72 (0.54-0.90) p = 0.008 | 6.03 p = 0.01 | 3.41 p = 0.10 |

In competition ELISA assays, serum from a patient known to be positive for anti-ApoA-I antibodies was pre-incubated with peptide F3L1 at different concentrations as indicated in FIG. 3 and then added to ELISA plates coated with intact ApoA-I, with the subsequent assay steps carried out according to the standard protocol. The results demonstrate that mimetic peptide F3L1 was capable of competitively inhibiting the binding to intact ApoA-I of IgG from a patient serum known to be positive for anti-ApoA-I antibodies, in a dose-dependent manner (FIG. 4).

Results of competition ELISA assays, carried out with F3, scrambled F3, and F3L1 (FIG. 5) show the absence of dose-dependent inhibition of the scramble peptide, which reinforces the specificity of the effect observed with F3L1 and the corresponding peptide without the lactam bridge. More generally, it emphasizes the importance of a proper secondary structure of the corresponding region derived from Helix F.

Scrambled F3: Ac-KELYLLKFTVESKVGSTELPLNF-SLA-NH$_2$ corresponds to amino acid sequence SEQ ID NO: 26 with the free amino group at the N-terminal end acetylated and the free carboxy group at the C-terminal end amidated.

Example 4: Mimetic Peptide F3L1 of the Invention Inhibits Anti-ApoA-I IgG-Related Pro-Inflammatory Response Polyclonal anti-ApoA-I IgG (Academy Bio-Medical Company; Houston, Tex., USA) applied at the optimal concentration of 40 µg/ml elicited a significant increase in TNF-α production by monocytes-derived human macrophages (FIG. 6A). This production was abrogated when anti-ApoA-I IgG was pre-incubated with peptide F3L1 for 2 h at room temperature prior to addition to the cell culture medium. The same effect was observed in a second experiment using a pool of IgG obtained from patients known to be positive for anti-ApoA-I antibodies (FIG. 6B), although the level of TNF-α production elicited by the pooled IgG was significantly lower than that elicited by the polyclonal anti-ApoA-I IgG.

These results show that mimetic peptide F3L1 inhibits the anti-ApoA-I IgG related pro-inflammatory response.

Example 5: Mimetic Peptide F3L1 Inhibits the Anti-ApoA-I IgG Related Chronotropic Response Addition of anti-ApoA-I antibodies elicited a strong chronotropic response in cultured rat cardiomyocytes (first group of bars on the left of FIG. 7. This response was fully abrogated when the antibody was pre-incubated with mimetic peptide F3L1 (75 µg/ml) for 2 h at room temperature prior to addition to the cultured cells (second group of bars from the left in FIG. 7. Finally, when added alone, peptide F3L1 did not alter either the basal frequency contraction rate or the contraction rate in the presence of 10 nM aldosterone (last group of bars on the right of FIG. 7, suggesting that its capacity to abrogate the anti-apoA-I IgG-related chronotropic response is directly related to its capacity to interact with anti-ApoA-I antibodies.

These results show that mimetic peptide F3L1 inhibits the anti-ApoA-I IgG related chronotropic response.

The results described in Examples 3 and 4 indicate that F3L1 could have a beneficial effect for the treatment of a cardiovascular disease.

Example 6: Identification by Mass Spectrometry of Epitopes of ApoA-I which are Immunoreactive to Anti-ApoA-I Antibodies To identify specific endogenous epitopes of ApoA-I, the purified ApoA-I was submitted to enzymatic digestion, hydrolyzing the protein specifically at the carboxyl side of lysine or at the carboxylic side of arginine, followed by peptide separation and purification by reversed phase-high performance liquid chromatography and peptide identification by mass spectrometry. The immunoreactivity to the digested protein and each fraction were tested by ELISA using serum samples from 3 patients with high titers and serum samples from 3 patients with low titers of autoantibodies.

For ApoA-I digested at lysine residues, the enzyme Endoproteinase Lys-C (Roche Applied Science) was used (amount of enzyme 1:50 was 1/50 of protein by weight, incubation for 18 h at 37° C., pH 8.5). ApoA-I digestion with Lys-C allowed identification of fractions 70 and 71 (FIG. 8) containing a previously unreported immunoreactive peptide epitope of amino acid sequence corresponding to amino acid residues 141-182 relative to mature amino acid sequence of ApoA-I of SEQ ID NO: 1, comprising the region derived from helix D of SEQ ID NO: 5 with a deletion of the last 2 amino acids of SEQ ID NO: 5. The amino acid sequence of this epitope is SEQ ID NO: 21.

In order to generate peptide fragments cleaved at arginine residues the conventional way would to use the enzyme ArgC. However, ArgC enzyme has a recognized lack of specificity, generating tryptic peptides, which abolished the immunoreactivity. To overcome this, ApoA1 was reversibly blocked at lysine residues with maleic anhydride prior to digestion and gain arginine-specific cleavage (Butler et al, 1967, *Biochemical Journal*, 103(3): 78P-79P; Butler et al, *Biochemical Journal*, 112(5): 679-689). This approach allowed identification of fractions 74 and 80 (FIG. 9) containing another immunoreactive peptide epitope of amino acid sequence corresponding to amino acid residues 216-243 relative to mature amino acid sequence of ApoA-I of SEQ ID NO: 1, comprising the region 1 derived from helix F of SEQ ID NO: 8. The amino acid sequence of this epitope is SEQ ID NO: 25.

The results described in Example 6 indicate that the specific epitopes identified in this example and, more generally, the region derived from Helix D of SEQ ID NO: 5 as well as region 1 and region 2 derived from Helix F of SEQ ID NO: 8 and SEQ ID NO: 9, respectively, are more immunoreactive to anti-ApoA-I antibodies than other fragments of ApoA-I containing other helices, in particular helix E contained in the peptide corresponding to amino acid residues 189-215 of mature ApoA-1 of SEQ ID NO: 1 that was less immunoreactive. Thus, peptides which amino acid sequence comprises at least one of these regions may advantageously be used to detect anti-ApoA-I autoantibodies.

Similar experiments as those described in Examples 4 and 5 have been repeated with a higher number of samples (n=9), which confirm the results presented in said examples.

SEQUENCE LISTING human ApoA-I: SEQ ID NO: 1
DEPPQSPWDRVKDLATVYVDVLKDSGRDYVSQFEGSALGKQLNLKLLDNWDS

VTSTFSKLREQLGPVTQEFWDNLEKETEGLRQEMSKDLEEVKAKVQPYLDDFQ

KKWQEEMELYRQKVEPLRAELQEGARQKLHELQEKLSPLGEEMRDRARAHVD

ALRTHLAPYSDELRQRLAARLEALKENGGARLAEYHAKATEHLSTLSEKAKPA

LEDLRQGLLPVLESFKVSFLSALEEYTKKLNTQ

Region derived from helix A: SEQ ID NO: 2:
VKDLATVYVDVLKDSGRDYVSQFEGSAL

Region derived from helix B: SEQ ID NO: 3:
DSVTSTFSKLREQLGPVTQEFWDNLEKETEGL

Region derived from helix C: SEQ ID NO: 4:
YLDDFQKKWQEEMELYRQKVEPLRAELQEGARQKLHE Region derived from helix D: SEQ ID NO: 5:
EEMRDRARAHVDALRTHLAPYSDELRQRLAARLEALKEN Region 1 derived from helix E: SEQ ID NO: 6:
ATEHLSTLSEKAKPALE Region 2 derived from helix E: SEQ ID NO: 7:
LAEYHAKATEHLSTLSEKAKPALEDLR Region 1 derived from helix F: SEQ ID NO: 8:
VLESFKVSFLSALEEYTKKLNT Region 2 derived from helix F: SEQ ID NO: 9:
GLLPVLESFKVSFLSALEEYTKKLNT A1S2 without acetylation and amidation:
VKDLR$_8$TVYVDVS$_5$KDSGRDYVSQFEGSAL
with a hydrocarbon staple linking R8 at position 5 and S5 at position 12 on said sequence, which is represented by:
VKDLXaaTVYVDVXaaKDSGRDYVSQFEGSAL (SEQ ID NO: 10 wherein Xaa at position 5 is substituted into a modified alanine of formula (I): —NH—C(CH$_3$)(R)—C(O)— wherein R is a hydrocarbon staple —(CH$_2$)$_6$—CH═CH—(CH$_2$)$_3$— linked to a subsequent Xaa at position 12, and wherein Xaa at position 12 is a modified alanine of formula (I): —NH—C(CH$_3$)(R')—C(O)— wherein R' is a single bond linked to the hydrocarbon staple from Xaa at position 5 as defined above)

B1S2 without acetylation and amidation:
DSVTSTR$_8$SKLREQS$_5$GPVTQEFWDNLEKETEGL
with a hydrocarbon staple linking R8 at position 7 and S5 at position 14 on said sequence, which is represented by:
DSVTSTXaaSKLREQXaaGPVTQEFWDNLEKETEGL (SEQ ID NO: 11 wherein Xaa at position 7 is a modified alanine of formula (I): —NH—C(CH$_3$)(R)—C(O)— wherein R is a hydrocarbon staple —(CH$_2$)$_6$—CH═CH—(CH$_2$)$_3$— linked to a subsequent Xaa at position 14, and wherein Xaa at position 14 is a modified alanine of formula (I): —NH—C(CH$_3$)(R')—C(O)— wherein R' is a single bond linked to the hydrocarbon staple from Xaa at position 7 as defined above)

C1S2 without acetylation and amidation:
YLDDFQKKWQEER$_8$ELYRQKS$_5$EPLRAELQEGARQKLHEL
with a hydrocarbon staple linking R8 at position 13 and S5 at position 20 on said sequence, which is represented by:
YLDDFQKKWQEEXaaELYRQKXaaEPLRAELQEGARQKLHEL (SEQ ID NO: 12 wherein Xaa at position 13 is a modified alanine of formula (I): —NH—C(CH$_3$)(R)—C(O)— wherein R is a hydrocarbon staple —(CH$_2$)$_6$—CH═CH—(CH$_2$)$_3$— linked to a subsequent Xaa at position 20, and wherein Xaa at position 20 is a modified alanine of formula (I): —NH—C(CH$_3$)(R')—C(O)— wherein R' is a single bond linked to the hydrocarbon staple from Xaa at position 13 as defined above)

D1S2A without acetylation and amidation:
EEMRDRARAHR$_8$DALRTHS$_5$APYSDELRQRLAARLEALKEN
with a hydrocarbon staple linking R8 at position 11 and S5 at position 18 on said sequence, which is represented by:
EEMRDRARAHXaaDALRTHXaaAPYSDELRQRLAARLEALKEN (SEQ ID NO: 13 wherein Xaa at position 11 is a modified alanine of formula (I): —NH—C(CH$_3$)(R)—C(O)— wherein R is a hydrocarbon staple —(CH$_2$)$_6$—CH═CH—(CH$_2$)$_3$— linked to a subsequent Xaa at position 18, and wherein Xaa at position 18 is a modified alanine of formula (I): —NH—C(CH$_3$)(R')—C(O)— wherein R' is a single bond linked to the hydrocarbon staple from Xaa at position 11 as defined above)

-continued

E1S2 without acetylation and amidation:
ATEHR₈STLSEKS₅KPALED
with a hydrocarbon staple linking R8 at position 5 and S5 at position 12 on said
sequence, which is represented by:
ATEHXaaSTLSEKXaaKPALED (SEQ ID NO: 14 wherein Xaa at position 5 is a
modified alanine of formula (I): —NH—C(CH₃)(R)—C(O)— wherein R is a hydrocarbon
staple —(CH₂)₆—CH=CH—(CH₂)₃— linked to a subsequent Xaa at position 12, and wherein
Xaa at position 12 is a modified alanine of formula (I): —NH—C(CH₃)(R')—C(O)— wherein
R' is a single bond linked to the hydrocarbon staple from Xaa at position 5 as defined
above)

F3L1 without acetylation and amidation:
GLLPVLESFKVSFLSALEEYTKKLNT
with a lactam bridge linking the E at position 19 and K at position 23 on said sequence,
which is represented by:
GLLPVLESFKVSFLSALEXaaYTKXaaLNT (SEQ ID NO: 19 wherein Xaa at position
19 is a modified amino acid of formula (I): —NH—C(H)(R)—C(O)— wherein R is a lactam
bridge —(CH₂)₂—CO—NH—(CH₂)₄— linked to a subsequent Xaa at position 23, and wherein
Xaa at position 23 is a modified amino acid of formula (I): —NH—C(H)(R')—C(O)—
wherein R' is a single bond linked to the lactam bridge from Xaa at position 19 as
defined above)

F3S2A without acetylation and amidation:
GLLPVLESFKVSFLSR₈LEEYTKS₅LNT
with a hydrocarbon staple linking R8 at position 16 and S5 at position 23 on said
sequence, which is represented by:
GLLPVLESFKVSFLSXaaLEEYTKXaaLNT (SEQ ID NO: 15 wherein Xaa at position
16 is a modified alanine of formula (I): —NH—C(CH₃)(R)—C(O)— wherein R is a
hydrocarbon staple —(CH₂)₆—CH=CH—(CH₂)₃— linked to a subsequent Xaa at position 23,
and wherein Xaa at position 23 is a modified alanine of formula (I): —NH—C(CH3)(R)—
C(O)— wherein R' is a single bond linked to the hydrocarbon staple from Xaa at position
16 as defined above)

F3S1B without acetylation and amidation:
GLLPVLESFKVSS₅LSAS₅EEYTKKLNT
with a hydrocarbon staple linking S5 at position 13 and S5 at position 17 on said
sequence, which is represented by:
GLLPVLESFKVSXaaLSAXaaEEYTKKLNT (SEQ ID NO: 16 wherein Xaa at position
13 is a modified alanine of formula (I): —NH—C(CH₃)(R)—C(O)— wherein R is a
hydrocarbon staple —(CH₂)₃—CH=CH—(CH₂)₃— linked to a subsequent Xaa at position 17,
and wherein Xaa at position 17 is a modified alanine of formula (I): —NH—C(CH₃)(R)—
C(O)— wherein R' is a single bond linked to the hydrocarbon staple from Xaa at position
13 as defined above)

F4S2B without acetylation and amidation:
VLESFKVSR₈LSALEES₅TKKLNT
with a hydrocarbon staple linking R8 at position 9 and S5 at position 16 on said
sequence, which is represented by:
VLESFKVSXaaLSALEEXaaTKKLNT (SEQ ID NO: 17 wherein Xaa at position 9 is a
modified alanine of formula (I): —NH—C(CH₃)(R)—C(O)— wherein R is a hydrocarbon
staple —(CH₂)₆—CH=CH—(CH₂)₃— linked to a subsequent Xaa at position 16, and wherein
Xaa at position 16 is a modified alanine of formula (I): —NH—C(CH₃)(R')—C(O)— wherein
R' is a single bond linked to the hydrocarbon staple from Xaa at position 9 as defined
above)

Linear EFL1 without amidation:
CAEYHAKATEHLSTLSEKAKPALEDLRXGLLPVLESFKVSFLSALEEYTKKLNT
C with X = Gln analogue at position 28 (side chain CH₂—S—CH₂—CONH₂ instead of CH₂—
CH₂—CONH₂) and a lactam bridge linking the E at position 47 and K at position 51 on
said sequence, which is represented by:
CAEYHAKATEHLSTLSEKAKPALEDLRXaaGLLPVLESFKVSFLSALEXaaYTKXaa
LNTC (SEQ ID NO: 18 wherein Xaa at position 28 is a Gln analogue having CH₂—S—
CH₂—CONH₂ as side chain, wherein Xaa at position 47 is a modified amino acid of
formula (I): —NH—C(H)(R)—C(O)— wherein R is a lactam bridge —(CH₂)₂—CO—NH—(CH₂)₄—
linked to a subsequent Xaa at position 51, and wherein Xaa at position 51 is a modified
amino acid of formula (I): —NH—C(H)(R')—C(O)— wherein R' is a single bond linked to
the lactam bridge from Xaa at position 47 as defined above)

F4L1 without acetylation and amidation: SEQ ID NO: 20:
VLESFKVSFLSALEXaaYTKXaaLNT
wherein Xaa at position 15 is a modified amino acid of formula (I): —NH—C(H)(R)—
C(O)— wherein R is a lactam bridge —(CH₂)₂—CO—NH—(CH₂)₄— linked to a subsequent Xaa
at position 19, and wherein Xaa at position 19 is a modified amino acid of formula (I):
—NH—C(H)(R')—C(O)— wherein R' is a single bond linked to the lactam bridge from Xaa
at position 15 as defined above)

-continued

D2 (aa 141-182): SEQ ID NO: 21:
LSPLGEEMRDRARAHVDALRTHLAPYSDELRQRLAARLEALK

D2S2A: SEQ ID NO: 22:
LSPLGEEMRDRARAHXaaDALRTHXaaAPYSDELRQRLAARLEALK
wherein Xaa at position 16 is a modified alanine of formula (I): —NH—C(CH$_3$)(R)—C(O)—
wherein R is a hydrocarbon staple —(CH$_2$)$_6$—CH=CH—(CH$_2$)$_3$— linked to a subsequent Xaa
at position 23, and wherein Xaa at position 23 is a modified alanine of formula (I):
—NH—C(CH$_3$)(R')—C(O)— wherein R' is a single bond linked to the hydrocarbon staple
from Xaa at position 16 as defined above)

D3: SEQ ID NO: 23:
EEMRDRARAHVDALRTHLAPYSDELRQRLAARLEALK

D3S2A: SEQ ID NO: 24:
EEMRDRARAHXaaDALRTHXaaAPYSDELRQRLAARLEALK
wherein Xaa at position 11 is a modified alanine of formula (I): —NH—C(CH$_3$)(R)—C(O)—
wherein R is a hydrocarbon staple —(CH$_2$)$_6$—CH=CH—(CH$_2$)$_3$— linked to a subsequent Xaa
at position 18, and wherein Xaa at position 18 is a modified alanine of formula (I):
—NH—C(CH$_3$)(R')—C(O)— wherein R' is a single bond linked to the hydrocarbon staple
from Xaa at position 11 as defined above

F5: SEQ ID NO: 25:
QGLLPVLESFKVSFLSALEEYTKKLNTQ

Scrambled F3 without acetylation and amidation: SEQ ID NO: 26:
KELYLLKFTVESKVGSTELPLNFSLA In the present sequence listing R$_8$ corresponds to (R)-2-(7'-octenyl)-Alanine and S$_5$
corresponds to (S)-2-(4'-pentenyl)-Alanine.

---

The invention claimed is:

1. A mimetic peptide of an epitope of Apolipoprotein A-I (ApoA-I), wherein said mimetic peptide is capable of specifically binding to an anti-ApoA-I antibody and is selected from the group consisting of:
   (i) SEQ ID NO: 8, SEQ ID NO: 9, SEQ ID NO: 15, SEQ ID NO: 16, SEQ ID NO: 17, SEQ ID NO: 19, or SEQ ID NO: 20;
   (ii) a variant of an amino acid sequence SEQ ID NO: 8, SEQ ID NO: 9, SEQ ID NO: 15, SEQ ID NO: 16, SEQ ID NO: 17, SEQ ID NO: 19, or SEQ ID NO: 20, wherein said variant consists in an amino acid sequence which is
      a. identical to any one of SEQ ID NO: 8, SEQ ID NO:9, SEQ ID NO: 15, SEQ ID NO: 16, SEQ ID NO: 17, SEQ ID NO: 19, and SEQ ID NO: 20, except that 1, 2, 3, 4, 5, or 6 amino acids of said sequences are substituted and/or chemically modified, without aborting the capacity of said mimetic peptide to specifically bind to an anti-ApoA-I antibody, or
      b. identical to any one of SEQ ID NO: 8, SEQ ID NO: 9, SEQ ID NO: 15, SEQ ID NO: 16, SEQ ID NO: 17, SEQ ID NO: 19, and SEQ ID NO: 20, except that 1, 2, or 3 amino acids are deleted without aborting the capacity of said mimetic peptide to specifically bind to an anti-ApoA-I antibody; and
   (iii) any combination of two of amino acid sequences under (i), and/or under (ii);
wherein the mimetic peptide has an internal cross-linking between at least two non-contiguous amino acids.

2. The mimetic peptide according to claim 1, wherein the peptide is selected from the group consisting of SEQ ID NO: 8 and SEQ ID NO: 9.

3. The mimetic peptide according to claim 1, wherein the internal cross-linking is a lactam bridge formed between two amino acids Xaa at positions n and n+4 on said peptide sequence.

4. The mimetic peptide according to claim 1, wherein the internal cross-linking is a hydrocarbon staple linking two amino acids Xaa at positions n and n+7 of said peptide sequence, wherein Xaa at position n is a modified alanine of formula (I): —NH—C(CH$_3$)(R)—C(O)— wherein R is a hydrocarbon staple —(CH$_2$)$_6$—CH=CH—(CH$_2$)$_3$— linked to a subsequent Xaa at position n+7, and wherein Xaa at position n+7 is a modified alanine of formula (I): —NH—C(CH$_3$)(R')—C(O)— wherein R' is a single bond linked to the hydrocarbon staple from said Xaa at position n.

5. The mimetic peptide according to claim 1, wherein the internal cross-linking is a hydrocarbon staple linking two amino acids Xaa at positions n and n+4 of said peptide sequence, wherein Xaa at position n is a modified alanine of formula (I): —NH—C(CH$_3$)(R)—C(O)— wherein R is a hydrocarbon staple —(CH$_2$)$_3$—CH=CH—(CH$_2$)$_3$— linked to a subsequent Xaa at position n+4, and wherein Xaa at position n+4 is a modified alanine of formula (I): —NH—C(CH$_3$)(R')—C(O)— wherein R' is a single bond linked to the hydrocarbon staple from said Xaa at position n.

6. The mimetic peptide according to claim 1, wherein:
   (i) the peptide consists of SEQ ID NO: 19 or a said variant thereof and the internal cross-linking is a lactam bridge linking a Glutamic acid (E) at position 19 and a Lysine (K) at position 23; or
   (ii) the peptide consists of SEQ ID NO: 15 or said variant thereof and the internal cross-linking is a hydrocarbon staple linking (R)-2-(7'-octenyl)-Alanine at position 16 and (S)-2-(4'-pentenyl)-Alanine at position 23; or
   (iii) the peptide consists of SEQ ID NO: 16 or said variant thereof and the internal cross-linking is a hydrocarbon staple linking (S)-2-(4'-pentenyl)-Alanine at position 13 and (S)-2-(4'-pentenyl)-Alanine at position 17; or
   (iv) the peptide consists of SEQ ID NO: 17 or said variant thereof and the internal cross-linking is a hydrocarbon staple linking (R)-2-(7'-octenyl)-Alanine at position 9 and (S)-2-(4'-pentenyl)-Alanine at position 16.

7. The mimetic peptide according to claim 1, consisting of SEQ ID NO: 15, SEQ ID NO: 16, SEQ ID NO: 17, SEQ ID NO: 19, SEQ ID NO: 20; or a said variant thereof.

8. The mimetic peptide of an epitope of ApoA-I according to claim 1, wherein said mimetic peptide is selected from the group consisting of:
   (i) SEQ ID NO: 8 or SEQ ID NO: 9;
   (ii) an amino acid sequence identical to any one of the sequences under (i) except that 1, 2, or 3 amino acids of said sequences are deleted without aborting the capacity of said mimetic peptide to specifically bind to an anti-ApoA-I antibody;
   (iii) an amino acid sequence identical to any one of the sequences under (i) except that 1, 2, 3, 4, 5, or 6 amino acids of said sequence are substituted and/or chemically modified, without aborting the capacity of said mimetic peptide to specifically bind to an anti-ApoA-I antibody; and
   (iv) any combination of amino acid sequences under (i), (ii), and/or (iii).

9. The mimetic peptide according to claim 8, wherein the peptide is SEQ ID NO: 8.

10. The mimetic peptide according to claim 6, having the free amino group at the N-terminal end acetylated and the free carboxy group at the C-terminal end amidated.

11. A pharmaceutical composition comprising at least one mimetic peptide according to claim 1 and at least one pharmaceutically acceptable carrier.

12. A kit for detecting anti-ApoA-I antibodies in a biological fluid sample, comprising at least one mimetic peptide according to claim 1 or a combination thereof for coupling, or already coupled to a solid matrix as solid phase support.

13. A method for detecting endogenous anti-ApoA-I antibodies in a biological fluid sample of a mammalian subject comprising:
   (a) contacting said biological fluid sample to a solid matrix having at least one mimetic peptide according to claim 1 coupled thereto, wherein the contacting is under conditions sufficient for binding an anti-ApoA-I antibody present in said biological fluid sample to said at least one mimetic peptide through antigen-antibody interactions;
   (c) removing any unbound antibody from the surface of said solid matrix; and
   (d) detecting the presence of an antigen-antibody complex bound to said solid matrix wherein the presence of said complex is indicative that the biological fluid sample contains endogenous anti-ApoA-I antibodies, wherein detection of bound antibodies under step (d) is carried out by a detection method selected from an optical detection, a mass variation detection and an electrical detection technique.

14. The method according to claim 13, wherein the presence of an antigen-antibody complex is indicative that a subject suffers from a cardiovascular disease.

15. The method according to claim 13, wherein the presence of an antigen-antibody complex is indicative that a subject suffers from at least one disorder selected from the group consisting of acute chest pain, acute coronary syndrome, rheumatoid arthritis, systemic lupus erythematosus, severe carotid stenosis, end-stage renal disease and periodontitis.

16. A method for treating an anti-ApoA-I antibody related cardiovascular disease in a subject in need thereof, the method comprising administering a mimetic peptide according to claim 1 to said subject.

17. The method according to claim 16, wherein an anti-ApoA-I antibody related cardiovascular disease is selected from the group consisting of acute chest pain and acute coronary syndrome.

18. The method according to claim 16, wherein said mimetic peptide has an amino acid sequence consisting of SEQ ID NO: 19; or a variant thereof wherein 1, 2, 3, 4, or 5 amino acids of said sequence are substituted and/or chemically modified without aborting the capacity of said mimetic peptide to bind specifically to an anti-ApoAI antibody; or a variant thereof wherein 1, 2, or 3 amino acids of said sequence are deleted without aborting the capacity of said mimetic peptide to bind specifically to an anti-ApoAI antibody.

19. A method for treating an anti-ApoA-I antibody related cardiovascular disease in a subject in need thereof, the method comprising administering a mimetic peptide according to claim 1 to said subject, wherein the cardiovascular disease has been detected by:
   (a) contacting a biological fluid sample from the subject in need thereof to a solid matrix having at least one mimetic peptide according to claim 1 coupled thereto, wherein the contacting is under conditions sufficient for binding an anti-ApoA-I antibody present in said biological fluid sample to said at least one mimetic peptide through antigen-antibody interactions;
   (c) removing any unbound antibody from the surface of said solid matrix; and
   (d) detecting the presence of an antigen-antibody complex bound to said solid matrix, wherein detection of bound antibodies under step (d) is carried out by a detection method selected from an optical detection, a mass variation detection and an electrical detection technique;
wherein the presence of said complex is indicative that the biological fluid sample contains endogenous anti-ApoA-I antibodies, and wherein the presence of an antigen-antibody complex is indicative that the subject suffers from a cardiovascular disease.

20. The mimetic peptide according to claim 1, which consists of genetically encoded amino acids.

21. The mimetic peptide according to claim 20, wherein the internal crosslinking exists between two non-contiguous amino acid residues.

22. The method according to claim 13, wherein the detection method is optical detection.

* * * * *

SEQUENCE LISTING

<160> NUMBER OF SEQ ID NOS: 26

<210> SEQ ID NO 1
<211> LENGTH: 243
<212> TYPE: PRT
<213> ORGANISM: Homo sapiens

<400> SEQUENCE: 1

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 2
<211> LENGTH: 28
<212> TYPE: PRT
<213> ORGANISM: Artificial Sequence
<220> FEATURE:
<223> OTHER INFORMATION: Region derived from Helix A of ApoA-I

<400> SEQUENCE: 2

Val Lys Asp Leu Ala Thr Val Tyr Val Asp Val Leu Lys Asp Ser Gly
1               5                   10                  15

Arg Asp Tyr Val Ser Gln Phe Glu Gly Ser Ala Leu
            20                  25

<210> SEQ ID NO 3
<211> LENGTH: 32
<212> TYPE: PRT
<213> ORGANISM: Artificial Sequence
<220> FEATURE:
<223> OTHER INFORMATION: Region derived from Helix B of ApoA-I

<400> SEQUENCE: 3

Asp Ser Val Thr Ser Thr Phe Ser Lys Leu Arg Glu Gln Leu Gly Pro
1               5                   10                  15

Val Thr Gln Glu Phe Trp Asp Asn Leu Glu Lys Glu Thr Glu Gly Leu
            20                  25                  30

<210> SEQ ID NO 4
<211> LENGTH: 37
<212> TYPE: PRT
<213> ORGANISM: Artificial Sequence
<220> FEATURE:
<223> OTHER INFORMATION: Region derived from Helix C of ApoA-I

<400> SEQUENCE: 4

Tyr Leu Asp Asp Phe Gln Lys Lys Trp Gln Glu Glu Met Glu Leu Tyr
1               5                   10                  15

Arg Gln Lys Val Glu Pro Leu Arg Ala Glu Leu Gln Glu Gly Ala Arg
            20                  25                  30

Gln Lys Leu His Glu
        35

<210> SEQ ID NO 5
<211> LENGTH: 39
<212> TYPE: PRT
<213> ORGANISM: Artificial Sequence
<220> FEATURE:
<223> OTHER INFORMATION: Region derived from Helix D of ApoA-I

<400> SEQUENCE: 5

Glu Glu Met Arg Asp Arg Ala Arg Ala His Val Asp Ala Leu Arg Thr
1               5                   10                  15

His Leu Ala Pro Tyr Ser Asp Glu Leu Arg Gln Arg Leu Ala Ala Arg
            20                  25                  30

```
Leu Glu Ala Leu Lys Glu Asn
        35

<210> SEQ ID NO 6
<211> LENGTH: 17
<212> TYPE: PRT
<213> ORGANISM: Artificial Sequence
<220> FEATURE:
<223> OTHER INFORMATION: Region 1 derived from Helix E of ApoA-I

<400> SEQUENCE: 6

Ala Thr Glu His Leu Ser Thr Leu Ser Glu Lys Ala Lys Pro Ala Leu
1               5                   10                  15

Glu

<210> SEQ ID NO 7
<211> LENGTH: 27
<212> TYPE: PRT
<213> ORGANISM: Artificial Sequence
<220> FEATURE:
<223> OTHER INFORMATION: Region 2 derived from Helix E of ApoA-I

<400> SEQUENCE: 7

Leu Ala Glu Tyr His Ala Lys Ala Thr Glu His Leu Ser Thr Leu Ser
1               5                   10                  15

Glu Lys Ala Lys Pro Ala Leu Glu Asp Leu Arg
            20                  25

<210> SEQ ID NO 8
<211> LENGTH: 22
<212> TYPE: PRT
<213> ORGANISM: Artificial Sequence
<220> FEATURE:
<223> OTHER INFORMATION: Region 1 derived from Helix F of ApoA-I

<400> SEQUENCE: 8

Val Leu Glu Ser Phe Lys Val Ser Phe Leu Ser Ala Leu Glu Glu Tyr
1               5                   10                  15

Thr Lys Lys Leu Asn Thr
            20

<210> SEQ ID NO 9
<211> LENGTH: 26
<212> TYPE: PRT
<213> ORGANISM: Artificial Sequence
<220> FEATURE:
<223> OTHER INFORMATION: Region 2 derived from Helix F of ApoA-I

<400> SEQUENCE: 9

Gly Leu Leu Pro Val Leu Glu Ser Phe Lys Val Ser Phe Leu Ser Ala
1               5                   10                  15

Leu Glu Glu Tyr Thr Lys Lys Leu Asn Thr
            20                  25

<210> SEQ ID NO 10
<211> LENGTH: 28
<212> TYPE: PRT
<213> ORGANISM: Artificial Sequence
<220> FEATURE:
<223> OTHER INFORMATION: A1S2 without acetylation and amidation
<220> FEATURE:
<221> NAME/KEY: MISC_FEATURE
<222> LOCATION: (5)..(5)
<223> OTHER INFORMATION: Xaa is substituted into a modified alanine of
      formula (I): -NH-C(CH3)(R)-C(O)- wherein R is a hydrocarbon staple
      -(CH2)6-CH=CH-(CH2)3- linked to a subsequent Xaa at position 12
```

```
<220> FEATURE:
<221> NAME/KEY: MISC_FEATURE
<222> LOCATION: (12)..(12)
<223> OTHER INFORMATION: Xaa is a modified alanine of formula (I):
      -NH-C(CH3)(R')-C(O)- wherein R' is a single bond linked to the
      hydrocarbon staple from Xaa at position 5

<400> SEQUENCE: 10

Val Lys Asp Leu Xaa Thr Val Tyr Val Asp Val Xaa Lys Asp Ser Gly
1               5                   10                  15

Arg Asp Tyr Val Ser Gln Phe Glu Gly Ser Ala Leu
            20                  25

<210> SEQ ID NO 11
<211> LENGTH: 32
<212> TYPE: PRT
<213> ORGANISM: Artificial Sequence
<220> FEATURE:
<223> OTHER INFORMATION: B1S2 without acetylation and amidation
<220> FEATURE:
<221> NAME/KEY: MISC_FEATURE
<222> LOCATION: (7)..(7)
<223> OTHER INFORMATION: Xaa is a modified alanine of formula (I):
      -NH-C(CH3)(R)-C(O)- wherein R is a hydrocarbon staple
      -(CH2)6-CH=CH-(CH2)3- linked to a subsequent Xaa at position 14
<220> FEATURE:
<221> NAME/KEY: MISC_FEATURE
<222> LOCATION: (14)..(14)
<223> OTHER INFORMATION: Xaa is a modified alanine of formula (I):
      -NH-C(CH3)(R')-C(O)- wherein R' is a single bond linked to the
      hydrocarbon staple from Xaa at position 7

<400> SEQUENCE: 11

Asp Ser Val Thr Ser Thr Xaa Ser Lys Leu Arg Glu Gln Xaa Gly Pro
1               5                   10                  15

Val Thr Gln Glu Phe Trp Asp Asn Leu Glu Lys Glu Thr Glu Gly Leu
            20                  25                  30

<210> SEQ ID NO 12
<211> LENGTH: 38
<212> TYPE: PRT
<213> ORGANISM: Artificial Sequence
<220> FEATURE:
<223> OTHER INFORMATION: C1S2 without acetylation and amidation
<220> FEATURE:
<221> NAME/KEY: MISC_FEATURE
<222> LOCATION: (13)..(13)
<223> OTHER INFORMATION: Xaa is a modified alanine of formula (I):
      -NH-C(CH3)(R)-C(O)- wherein R is a hydrocarbon staple
      -(CH2)6-CH=CH-(CH2)3- linked to a subsequent Xaa at position 20
<220> FEATURE:
<221> NAME/KEY: MISC_FEATURE
<222> LOCATION: (20)..(20)
<223> OTHER INFORMATION: Xaa is a modified alanine of formula (I):
      -NH-C(CH3)(R')-C(O)- wherein R' is a single bond linked to the
      hydrocarbon staple from Xaa at position 13

<400> SEQUENCE: 12

Tyr Leu Asp Asp Phe Gln Lys Lys Trp Gln Glu Glu Xaa Glu Leu Tyr
1               5                   10                  15

Arg Gln Lys Xaa Glu Pro Leu Arg Ala Glu Leu Gln Glu Gly Ala Arg
            20                  25                  30

Gln Lys Leu His Glu Leu
        35

<210> SEQ ID NO 13
<211> LENGTH: 39
<212> TYPE: PRT
<213> ORGANISM: Artificial Sequence
```

```
<220> FEATURE:
<223> OTHER INFORMATION: D1S2A without acetylation and amidation
<220> FEATURE:
<221> NAME/KEY: MISC_FEATURE
<222> LOCATION: (11)..(11)
<223> OTHER INFORMATION: Xaa is a modified alanine of formula (I):
      -NH-C(CH3)(R)-C(O)- wherein R is a hydrocarbon staple
      -(CH2)6-CH=CH-(CH2)3- linked to a subsequent Xaa at position 18
<220> FEATURE:
<221> NAME/KEY: MISC_FEATURE
<222> LOCATION: (18)..(18)
<223> OTHER INFORMATION: Xaa is a modified alanine of formula (I):
      -NH-C(CH3)(R')-C(O)- wherein R' is a single bond linked to the
      hydrocarbon staple from Xaa at position 11

<400> SEQUENCE: 13

Glu Glu Met Arg Asp Arg Ala Arg Ala His Xaa Asp Ala Leu Arg Thr
1               5                   10                  15

His Xaa Ala Pro Tyr Ser Asp Glu Leu Arg Gln Arg Leu Ala Ala Arg
            20                  25                  30

Leu Glu Ala Leu Lys Glu Asn
        35

<210> SEQ ID NO 14
<211> LENGTH: 18
<212> TYPE: PRT
<213> ORGANISM: Artificial Sequence
<220> FEATURE:
<223> OTHER INFORMATION: EIS2 without acetylation and amidation
<220> FEATURE:
<221> NAME/KEY: MISC_FEATURE
<222> LOCATION: (5)..(5)
<223> OTHER INFORMATION: Xaa is a modified alanine of formula (I):
      -NH-C(CH3)(R)-C(O)- wherein R is a hydrocarbon staple
      -(CH2)6-CH=CH-(CH2)3- linked to a subsequent Xaa at position 12
<220> FEATURE:
<221> NAME/KEY: MISC_FEATURE
<222> LOCATION: (12)..(12)
<223> OTHER INFORMATION: Xaa at position 12 is a modified alanine of
      formula (I): -NH-C(CH3)(R')-C(O)- wherein R' is a single bond
      linked to the hydrocarbon staple from Xaa at position 5

<400> SEQUENCE: 14

Ala Thr Glu His Xaa Ser Thr Leu Ser Glu Lys Xaa Lys Pro Ala Leu
1               5                   10                  15

Glu Asp

<210> SEQ ID NO 15
<211> LENGTH: 26
<212> TYPE: PRT
<213> ORGANISM: Artificial Sequence
<220> FEATURE:
<223> OTHER INFORMATION: F3S2A without acetylation and amidation
<220> FEATURE:
<221> NAME/KEY: MISC_FEATURE
<222> LOCATION: (16)..(16)
<223> OTHER INFORMATION: Xaa is a modified alanine of formula (I):
      -NH-C(CH3)(R)-C(O)- wherein R is a hydrocarbon staple
      -(CH2)6-CH=CH-(CH2)3- linked to a subsequent Xaa at position 23
<220> FEATURE:
<221> NAME/KEY: MISC_FEATURE
<222> LOCATION: (23)..(23)
<223> OTHER INFORMATION: Xaa is a modified alanine of formula (I):
      -NH-C(CH3)(R')-C(O)- wherein R' is a single bond linked to the
      hydrocarbon staple from Xaa at position 16

<400> SEQUENCE: 15

Gly Leu Leu Pro Val Leu Glu Ser Phe Lys Val Ser Phe Leu Ser Xaa
1               5                   10                  15

Leu Glu Glu Tyr Thr Lys Xaa Leu Asn Thr
```

<210> SEQ ID NO 16
<211> LENGTH: 26
<212> TYPE: PRT
<213> ORGANISM: Artificial Sequence
<220> FEATURE:
<223> OTHER INFORMATION: F3S1B without acetylation and amidation
<220> FEATURE:
<221> NAME/KEY: MISC_FEATURE
<222> LOCATION: (13)..(13)
<223> OTHER INFORMATION: Xaa is a modified alanine of formula (I):
      -NH-C(CH3)(R)-C(O)- wherein R is a hydrocarbon staple
      -(CH2)3-CH=CH-(CH2)3- linked to a subsequent Xaa at position 17
<220> FEATURE:
<221> NAME/KEY: MISC_FEATURE
<222> LOCATION: (17)..(17)
<223> OTHER INFORMATION: Xaa at position 17 is a modified alanine of
      formula (I): -NH-C(CH3)(R')-C(O)- wherein R' is a single bond
      linked to the hydrocarbon staple from Xaa at position 13

<400> SEQUENCE: 16

Gly Leu Leu Pro Val Leu Glu Ser Phe Lys Val Ser Xaa Leu Ser Ala
1               5                   10                  15

Xaa Glu Glu Tyr Thr Lys Lys Leu Asn Thr
            20                  25

<210> SEQ ID NO 17
<211> LENGTH: 22
<212> TYPE: PRT
<213> ORGANISM: Artificial Sequence
<220> FEATURE:
<223> OTHER INFORMATION: F4S2B without acetylation and amidation
<220> FEATURE:
<221> NAME/KEY: MISC_FEATURE
<222> LOCATION: (9)..(9)
<223> OTHER INFORMATION: wherein Xaa is a modified alanine of formula
      (I): -NH-C(CH3)(R)-C(O)- wherein R is a hydrocarbon staple
      -(CH2)6-CH=CH-(CH2)3- linked to a subsequent Xaa at position 16
<220> FEATURE:
<221> NAME/KEY: MISC_FEATURE
<222> LOCATION: (16)..(16)
<223> OTHER INFORMATION: Xaa is a modified alanine of formula (I):
      -NH-C(CH3)(R')-C(O)- wherein R' is a single bond linked to the
      hydrocarbon staple from Xaa at position 9

<400> SEQUENCE: 17

Val Leu Glu Ser Phe Lys Val Ser Xaa Leu Ser Ala Leu Glu Glu Xaa
1               5                   10                  15

Thr Lys Lys Leu Asn Thr
            20

<210> SEQ ID NO 18
<211> LENGTH: 55
<212> TYPE: PRT
<213> ORGANISM: Artificial Sequence
<220> FEATURE:
<223> OTHER INFORMATION: linear EFL1 without amidation
<220> FEATURE:
<221> NAME/KEY: MISC_FEATURE
<222> LOCATION: (28)..(28)
<223> OTHER INFORMATION: X is a Gln analogue having CH2-S-CH2-CONH2 as
      side chain
<220> FEATURE:
<221> NAME/KEY: MISC_FEATURE
<222> LOCATION: (47)..(47)
<223> OTHER INFORMATION: Xaa is a modified amino acid of formula (I):
      -NH-C(H)(R)-C(O)- wherein R is a lactam bridge
      -(CH2)2-CO-NH-(CH2)4- linked to a subsequent Xaa at position 51
<220> FEATURE:
<221> NAME/KEY: MISC_FEATURE
<222> LOCATION: (51)..(51)

```
<223> OTHER INFORMATION: Xaa is a modified amino acid of formula (I):
      -NH-C(H)(R')-C(O)- wherein R' is a single bond linked to the
      lactam bridge from Xaa at position 47

<400> SEQUENCE: 18

Cys Ala Glu Tyr His Ala Lys Ala Thr Glu His Leu Ser Thr Leu Ser
1               5                   10                  15

Glu Lys Ala Lys Pro Ala Leu Glu Asp Leu Arg Xaa Gly Leu Leu Pro
            20                  25                  30

Val Leu Glu Ser Phe Lys Val Ser Phe Leu Ser Ala Leu Glu Xaa Tyr
        35                  40                  45

Thr Lys Xaa Leu Asn Thr Cys
    50                  55

<210> SEQ ID NO 19
<211> LENGTH: 26
<212> TYPE: PRT
<213> ORGANISM: Artificial Sequence
<220> FEATURE:
<223> OTHER INFORMATION: F3L1 without acetylation and amidation
<220> FEATURE:
<221> NAME/KEY: MISC_FEATURE
<222> LOCATION: (19)..(19)
<223> OTHER INFORMATION: Xaa is a modified amino acid of formula (I):
      -NH-C(H)(R)-C(O)- wherein R is a lactam bridge
      -(CH2)2-CO-NH-(CH2)4- linked to a subsequent Xaa at position 23
<220> FEATURE:
<221> NAME/KEY: MISC_FEATURE
<222> LOCATION: (23)..(23)
<223> OTHER INFORMATION: Xaa is a modified amino acid of formula (I):
      -NH-C(H)(R')-C(O)- wherein R' is a single bond linked to the
      lactam bridge from Xaa at position 19

<400> SEQUENCE: 19

Gly Leu Leu Pro Val Leu Glu Ser Phe Lys Val Ser Phe Leu Ser Ala
1               5                   10                  15

Leu Glu Xaa Tyr Thr Lys Xaa Leu Asn Thr
            20                  25

<210> SEQ ID NO 20
<211> LENGTH: 22
<212> TYPE: PRT
<213> ORGANISM: Artificial Sequence
<220> FEATURE:
<223> OTHER INFORMATION: F4L1 without acetylation and amidation
<220> FEATURE:
<221> NAME/KEY: MISC_FEATURE
<222> LOCATION: (15)..(15)
<223> OTHER INFORMATION: Xaa is a modified amino acid of formula (I):
      -NH-C(H)(R)-C(O)- wherein R is a lactam bridge
      -(CH2)2-CO-NH-(CH2)4- linked to a subsequent Xaa at position 19
<220> FEATURE:
<221> NAME/KEY: MISC_FEATURE
<222> LOCATION: (19)..(19)
<223> OTHER INFORMATION: Xaa is a modified amino acid of formula (I):
      -NH-C(H)(R')-C(O)- wherein R' is a single bond linked to the
      lactam bridge from Xaa at position 15

<400> SEQUENCE: 20

Val Leu Glu Ser Phe Lys Val Ser Phe Leu Ser Ala Leu Glu Xaa Tyr
1               5                   10                  15

Thr Lys Xaa Leu Asn Thr
            20

<210> SEQ ID NO 21
<211> LENGTH: 42
<212> TYPE: PRT
<213> ORGANISM: Artificial Sequence
```

```
<220> FEATURE:
<223> OTHER INFORMATION: D2

<400> SEQUENCE: 21

Leu Ser Pro Leu Gly Glu Glu Met Arg Asp Arg Ala Arg Ala His Val
1               5                   10                  15

Asp Ala Leu Arg Thr His Leu Ala Pro Tyr Ser Asp Glu Leu Arg Gln
            20                  25                  30

Arg Leu Ala Ala Arg Leu Glu Ala Leu Lys
        35                  40

<210> SEQ ID NO 22
<211> LENGTH: 42
<212> TYPE: PRT
<213> ORGANISM: Artificial sequence
<220> FEATURE:
<223> OTHER INFORMATION: D2S2A
<220> FEATURE:
<221> NAME/KEY: MISC_FEATURE
<222> LOCATION: (16)..(16)
<223> OTHER INFORMATION: Xaa is a modified alanine of formula (I):
      -NH-C(CH3)(R)-C(O)- wherein R is a hydrocarbon staple
      -(CH2)6-CH=CH-(CH2)3- linked to a subsequent Xaa at position 23
<220> FEATURE:
<221> NAME/KEY: MISC_FEATURE
<222> LOCATION: (23)..(23)
<223> OTHER INFORMATION: Xaa is a modified alanine of formula (I):
      -NH-C(CH3)(R')-C(O)- wherein R' is a single bond linked to the
      hydrocarbon staple from Xaa at position 16

<400> SEQUENCE: 22

Leu Ser Pro Leu Gly Glu Glu Met Arg Asp Arg Ala Arg Ala His Xaa
1               5                   10                  15

Asp Ala Leu Arg Thr His Xaa Ala Pro Tyr Ser Asp Glu Leu Arg Gln
            20                  25                  30

Arg Leu Ala Ala Arg Leu Glu Ala Leu Lys
        35                  40

<210> SEQ ID NO 23
<211> LENGTH: 37
<212> TYPE: PRT
<213> ORGANISM: artificial sequence
<220> FEATURE:
<223> OTHER INFORMATION: D3

<400> SEQUENCE: 23

Glu Glu Met Arg Asp Arg Ala Arg Ala His Val Asp Ala Leu Arg Thr
1               5                   10                  15

His Leu Ala Pro Tyr Ser Asp Glu Leu Arg Gln Arg Leu Ala Ala Arg
            20                  25                  30

Leu Glu Ala Leu Lys
        35

<210> SEQ ID NO 24
<211> LENGTH: 37
<212> TYPE: PRT
<213> ORGANISM: artificial sequence
<220> FEATURE:
<223> OTHER INFORMATION: D3S2A
<220> FEATURE:
<221> NAME/KEY: MISC_FEATURE
<222> LOCATION: (11)..(11)
<223> OTHER INFORMATION: Xaa is a modified alanine of formula (I):
      -NH-C(CH3)(R)-C(O)- wherein R is a hydrocarbon staple
      -(CH2)6-CH=CH-(CH2)3- linked to a subsequent Xaa at position 18
<220> FEATURE:
<221> NAME/KEY: MISC_FEATURE
```

```
<222> LOCATION: (18)..(18)
<223> OTHER INFORMATION: Xaa is a modified alanine of formula (I):
      -NH-C(CH3)(R')-C(O)- wherein R' is a single bond linked to the
      hydrocarbon staple from Xaa at position 11

<400> SEQUENCE: 24

Glu Glu Met Arg Asp Arg Ala Arg Ala His Xaa Asp Ala Leu Arg Thr
1               5                   10                  15

His Xaa Ala Pro Tyr Ser Asp Glu Leu Arg Gln Arg Leu Ala Ala Arg
            20                  25                  30

Leu Glu Ala Leu Lys
        35

<210> SEQ ID NO 25
<211> LENGTH: 28
<212> TYPE: PRT
<213> ORGANISM: artificial sequence
<220> FEATURE:
<223> OTHER INFORMATION: F5

<400> SEQUENCE: 25

Gln Gly Leu Leu Pro Val Leu Glu Ser Phe Lys Val Ser Phe Leu Ser
1               5                   10                  15

Ala Leu Glu Glu Tyr Thr Lys Lys Leu Asn Thr Gln
            20                  25

<210> SEQ ID NO 26
<211> LENGTH: 26
<212> TYPE: PRT
<213> ORGANISM: artificial sequence
<220> FEATURE:
<223> OTHER INFORMATION: Scrambled F3 without acetylation and amidation

<400> SEQUENCE: 26

Lys Glu Leu Tyr Leu Leu Lys Phe Thr Val Glu Ser Lys Val Gly Ser
1               5                   10                  15

Thr Glu Leu Pro Leu Asn Phe Ser Leu Ala
            20                  25
```